US010898458B2

(12) United States Patent
Sancilio et al.

(10) Patent No.: US 10,898,458 B2
(45) Date of Patent: *Jan. 26, 2021

(54) SELF-MICELLIZING FATTY ACIDS AND FATTY ACID ESTER COMPOSITIONS AND THEIR USE IN THE TREATMENT OF DISEASE STATES

(71) Applicant: Micelle BioPharma, Inc., Riviera Beach, FL (US)

(72) Inventors: Frederick D. Sancilio, Palm Beach Gardens, FL (US); Thorsteinn Thorsteinsson, Boynton Beach, FL (US); Glynis Daniel-Archibald, Port St. Lucie, FL (US); Miguel Lopez-Toledano, Wellington, FL (US); Ahmed Abd Almalik Ahmed Mohammed Daak, West Palm Beach, FL (US)

(73) Assignee: Micelle BioPharma, Inc., Rivera Beach, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/605,972

(22) Filed: May 26, 2017

(65) Prior Publication Data

US 2017/0258752 A1  Sep. 14, 2017

Related U.S. Application Data

(63) Continuation of application No. 15/180,430, filed on Jun. 13, 2016, now abandoned, which is a
(Continued)

(51) Int. Cl.
| | |
|---|---|
| *A61K 31/232* | (2006.01) |
| *A61K 9/107* | (2006.01) |
| *A61K 9/48* | (2006.01) |
| *A61K 31/05* | (2006.01) |
| *A61K 31/201* | (2006.01) |
| *A61K 31/202* | (2006.01) |
| *A61K 31/353* | (2006.01) |
| *A61K 31/355* | (2006.01) |

(Continued)

(52) U.S. Cl.
CPC .......... *A61K 31/232* (2013.01); *A61K 9/1075* (2013.01); *A61K 9/4858* (2013.01); *A61K 31/05* (2013.01); *A61K 31/201* (2013.01); *A61K 31/202* (2013.01); *A61K 31/353* (2013.01); *A61K 31/355* (2013.01); *A61K 31/7024* (2013.01); *A61K 47/10* (2013.01); *A61K 47/26* (2013.01)

(58) Field of Classification Search
CPC .. A61K 31/232; A61K 47/10; A61K 31/7024; A61K 31/05; A61K 47/26; A61K 31/355; A61K 9/4858; A61K 9/1075; A61K 31/353; A61K 31/201; A61K 31/202
See application file for complete search history.

(56) References Cited

U.S. PATENT DOCUMENTS

| | | | |
|---|---|---|---|
| 4,513,008 | A | 4/1985 | Revici et al. |
| 4,992,476 | A | 2/1991 | Geria |

(Continued)

FOREIGN PATENT DOCUMENTS

| | | |
|---|---|---|
| CN | 101380358 A | 3/2009 |
| EP | 1782807 A1 | 5/2007 |

(Continued)

OTHER PUBLICATIONS

Kris-Etherton, et al. Omega-3 Fatty Acids and Cardiovascular Disease: New Recommendations From the American Heart Association. Arterioscler Thromb Vase Biol. 2003;23: 151-152 doi: 10.1161/01 .ATV .0000057393.97337 .AE.

(Continued)

*Primary Examiner* — Snigdha Maewall
(74) *Attorney, Agent, or Firm* — E. Eric Mills; Nexsen Pruet, PLLC

(57) ABSTRACT

Described herein are compositions including at least one omega-3 fatty acid (either in the triglyceride, ester or free fatty acid ester form) and at least one surface active agent; wherein the compositions form micelles when in contact with an aqueous medium. Also provided are methods of administering to a subject a composition including at least one omega-3 fatty acid (either in the triglyceride, ester or free fatty acid ester form) and at least one surface active agent, wherein the compositions form micelles when in contact with an aqueous medium, and the bioavailability of the omega-3 fatty acid is substantially independent of a food effect. The compositions are useful for treating certain disease states which may include (1) malabsorption syndromes, (2) primary sclerosing cholangitis (PSC), (3) non-alcoholic fatty liver disease (NAFLD), (4) sickle cell disease (SCD), (5) age-related macular degeneration (AMD), and (6) neurodegenerative disease, including, Parkinson's Disease (PD), Alzheimer's Disease (AD), Amyotrophic Lateral Sclerosis (ALS or Lou Gehrig's Disease), Epilepsy, Bi-polar Syndrome, traumatic brain injury, peripheral neuropathy, and Multiple Sclerosis (MS). Described are also various dosage forms for administering the compositions and use of the compositions in functional foods. Provided herein are also kits with instructions for their administration.

20 Claims, 12 Drawing Sheets

Related U.S. Application Data continuation of application No. PCT/US2015/054933, filed on Oct. 9, 2015, and a continuation-in-part of application No. 14/808,876, filed on Jul. 24, 2015, now Pat. No. 9,364,562, which is a continuation of application No. 14/456,750, filed on Aug. 11, 2014, now Pat. No. 9,302,017, which is a continuation of application No. PCT/US2013/030211, filed on Mar. 11, 2013, and a continuation-in-part of application No. 14/808,871, filed on Jul. 24, 2015, now Pat. No. 9,375,490, which is a continuation of application No. 14/456,750, filed on Aug. 11, 2014, now Pat. No. 9,302,017, and a continuation-in-part of application No. 14/808,866, filed on Jul. 24, 2015, now Pat. No. 9,364,561, which is a continuation of application No. 14/456,750, filed on Aug. 11, 2014, now Pat. No. 9,302,017, and a continuation-in-part of application No. 14/808,847, filed on Jul. 24, 2015, now Pat. No. 9,364,560, which is a continuation of application No. 14/456,750, filed on Aug. 11, 2014, now Pat. No. 9,302,017, and a continuation-in-part of application No. 14/808,835, filed on Jul. 24, 2015, now Pat. No. 9,364,559, which is a continuation of application No. 14/456,750, filed on Aug. 11, 2014, now Pat. No. 9,302,017, and a continuation-in-part of application No. 14/808,809, filed on Jul. 24, 2015, now Pat. No. 9,364,558, which is a continuation of application No. 14/456,750, filed on Aug. 11, 2014, now Pat. No. 9,302,017, and a continuation-in-part of application No. 14/808,777, filed on Jul. 24, 2015, now Pat. No. 9,370,585, which is a continuation of application No. 14/456,750, filed on Aug. 11, 2014, now Pat. No. 9,302,017, which is a continuation-in-part of application No. 15/134,419, filed on Apr. 21, 2016, now abandoned, which is a continuation-in-part of application No. 14/578,692, filed on Dec. 22, 2014, now abandoned, which is a continuation-in-part of application No. 14/456,731, filed on Aug. 11, 2014, now Pat. No. 9,302,016, which is a continuation of application No. PCT/US2013/030211, filed on Mar. 11, 2013, and a continuation-in-part of application No. 14/456,750, filed on Aug. 11, 2014, now Pat. No. 9,302,017, and a continuation-in-part of application No. 15/134,417, filed on Apr. 21, 2016, now abandoned, which is a continuation-in-part of application No. 14/578,697, filed on Dec. 22, 2014, now abandoned, which is a continuation-in-part of application No. 14/456,731, filed on Aug. 11, 2014, now Pat. No. 9,302,016, and a continuation-in-part of application No. 14/456,750, filed on Aug. 11, 2014, now Pat. No. 9,302,017, and a continuation-in-part of application No. 15/132,278, filed on Apr. 9, 2016, now abandoned, which is a continuation-in-part of application No. 14/578,709, filed on Dec. 22, 2014, now abandoned, which is a continuation-in-part of application No. 14/456,731, filed on Aug. 11, 2014, now Pat. No. 9,302,016, and a continuation-in-part of application No. 14/456,750, filed on Aug. 11, 2014, now Pat. No. 9,302,017, and a continuation-in-part of application No. 15/058,228, filed on Mar. 2, 2016, now Pat. No. 9,480,651, which is a continuation-in-part of application No. 14/456,731, filed on Aug. 11, 2014, now Pat. No. 9,302,016, and a continuation-in-part of application No. 14/456,750, filed on Aug. 11, 2014, now Pat. No. 9,302,017.

(60) Provisional application No. 62/062,638, filed on Oct. 10, 2014, provisional application No. 62/062,643, filed on Oct. 10, 2014, provisional application No. 62/062,646, filed on Oct. 10, 2014, provisional application No. 62/062,652, filed on Oct. 10, 2014, provisional application No. 62/062,634, filed on Oct. 10, 2014, provisional application No. 62/062,651, filed on Oct. 10, 2014, provisional application No. 61/618,161, filed on Mar. 30, 2012, provisional application No. 62/127,505, filed on Mar. 2, 2015.

(51) Int. Cl.
| | | |
|---|---|---|
| A61K 31/7024 | (2006.01) | |
| A61K 47/10 | (2017.01) | |
| A61K 47/26 | (2006.01) | |

(56) References Cited

U.S. PATENT DOCUMENTS

| | | |
|---|---|---|
| 5,502,077 A | 3/1996 | Breivik et al. |
| 6,121,210 A | 9/2000 | Taylor |
| 6,284,268 B1 | 9/2001 | Mishra et al. |
| 7,041,324 B2 | 5/2006 | Myhre |
| 7,642,287 B2 | 1/2010 | Guzman et al. |
| 7,919,526 B2 | 4/2011 | Rozen et al. |
| 8,071,646 B2 | 12/2011 | Feuerstein et al. |
| 8,324,276 B2 | 12/2012 | Bryhn |
| 8,609,726 B2 | 1/2013 | Bryhn |
| 8,377,494 B2 | 2/2013 | Behnam |
| 8,529,979 B2 | 9/2013 | Abril et al. |
| 8,563,608 B2 | 10/2013 | Manku et al. |
| 8,618,166 B2 | 12/2013 | Osterloh et al. |
| 8,618,168 B2 * | 12/2013 | Fujii ............... A61K 9/1075 426/541 |
| 8,691,871 B2 | 4/2014 | Osterloh et al. |
| 9,056,088 B2 | 6/2015 | Osterloh et al. |
| 2005/0074414 A1 | 4/2005 | Tamarkin et al. |
| 2005/0075407 A1 | 4/2005 | Tamarkin et al. |
| 2005/0118254 A1 | 6/2005 | Choi et al. |
| 2005/0171200 A1 | 8/2005 | Calder et al. |
| 2006/0009522 A1 | 1/2006 | Dana et al. |
| 2006/0165735 A1 | 7/2006 | Abril et al. |
| 2006/0210622 A1 | 9/2006 | Pace et al. |
| 2006/0211763 A1 | 9/2006 | Fawzy et al. |
| 2006/0223737 A1 | 10/2006 | Sebillotte-Arnaud et al. |
| 2007/0104779 A1 | 5/2007 | Rongen et al. |
| 2007/0112071 A1 | 5/2007 | Bryhn et al. |
| 2007/0259957 A1 | 11/2007 | Ueshima et al. |
| 2008/0058418 A1 | 3/2008 | D'Angelo et al. |
| 2008/0102131 A1 | 5/2008 | Nagira et al. |
| 2008/0138293 A1 | 6/2008 | Tamarkin et al. |
| 2008/0255247 A1 | 10/2008 | Sagalowicz et al. |
| 2008/0275119 A1 | 11/2008 | Puder et al. |
| 2008/0306154 A1 | 12/2008 | Svensson et al. |
| 2009/0011012 A1 | 1/2009 | Baum |
| 2009/0053306 A1 | 2/2009 | Agarwal et al. |
| 2009/0149533 A1 | 6/2009 | Almarsson et al. |
| 2009/0182049 A1 | 7/2009 | Opheim |
| 2010/0062057 A1 | 3/2010 | Berge et al. |
| 2010/0305045 A1 | 12/2010 | Yu |
| 2011/0045050 A1 | 2/2011 | Elbayoumi et al. |
| 2011/0118351 A1 | 5/2011 | Berl |
| 2011/0262534 A1 | 10/2011 | Berge et al. |
| 2012/0053242 A1 | 3/2012 | Cela Lopez |
| 2012/0093922 A1 | 4/2012 | Manku et al. |
| 2012/0207800 A1 | 8/2012 | Abu-Saker et al. |
| 2012/0225945 A1 * | 9/2012 | Hustvedt ............... A61K 9/4858 514/560 |
| 2013/0203701 A1 | 8/2013 | Leighton |
| 2014/0004186 A1 | 1/2014 | Hustvedt et al. |
| 2014/0050807 A1 | 2/2014 | Leighton |
| 2014/0154310 A1 | 6/2014 | Osterloh et al. |

(56) References Cited

U.S. PATENT DOCUMENTS

| | | |
|---|---|---|
| 2014/0155455 A1 | 6/2014 | Osterloh et al. |
| 2014/0186503 A1 | 7/2014 | Mattson et al. |

FOREIGN PATENT DOCUMENTS

| | | |
|---|---|---|
| EP | 1946755 A1 | 7/2008 |
| EP | 2433630 A1 | 3/2012 |
| WO | 9302665 A1 | 2/1993 |
| WO | 9929316 A1 | 6/1999 |
| WO | 0048592 A1 | 8/2000 |
| WO | 2004009054 A2 | 1/2004 |
| WO | 2011018480 A1 | 2/2011 |
| WO | 2011022396 A1 | 2/2011 |
| WO | 2011048493 A1 | 4/2011 |
| WO | 2012032414 A2 | 3/2012 |
| WO | 2012032415 A2 | 3/2012 |
| WO | 2012032417 A2 | 3/2012 |
| WO | 2013123466 A1 | 8/2013 |

OTHER PUBLICATIONS

Holub, Bruce J. Docosahexaenoic acid (DHA) and cardiovascular disease risk factors. Prostaglandins, Leukotrienes and Essential Fatty Acids 81 (2009) 199-204.

Raatz, S. K. Enhanced Absorption of n-3 Fatty Acids from Emulsified Compared with Encapsulated Fish Oil. J Am Diet Assoc. 2009; 109:1076-1081. doi: 10.1016/j.jada.2009.03.06.

Kris-Etherton, et al. Fish Consumption, Fish Oil, Omega-3 Fatty Acids, and Cardiovascular Disease. Circulation. 2002;106:2747-2757. doi: 10.1161/01.C1R.0000038493.65177.94.

Weitz, D. et al. Fish Oil for the Treatment of Cardiovascular Disease. Cardiol Rev. 2010; 18(5): 258-263. doi:10.1097/CRD.Ob013e3181ea0de0.

Breslow, J.L. n-3 Fatty acids and cardiovascular disease. Am J Clin Nutr 2006;83(suppi):1477S-82S.

Fatouros D.G. et al. Clinical studies with oral lipid based formulations of poorly soluble compounds Therapeutics and Clinical Risk Management 2007:3(4) 591-604.

Fomuso, L.D. et al. Effect of Emulsifier on Oxidation Properties of Fish Oil-Based Structured Lipid Emulsions. J. Agric. Food Chem. 2002,50, 2957-2961.

Garaiova, I. et al. A randomised cross-over trial in healthy adults indicating improved absorption of omega-3 fatty acids pre-emulsification. Nutrition Journal 2007, 6:4 doi:10.1186/1475-2891-6-4.

Bauer, I. et al. Omega-3 Fatty Acids Modify Human Cortical Visual Processing—A Double-Blind, Crossover Study. Omega-3 Fatty Acids Modify Human Cortical Visual Processing—A Double-Blind, Crossover Study. PLoS One. 2011. 6(12): e28214. doi:10.1371/journal.pone.0028214.

Stone, N.J. Fish Consumption, Fish Oil, Lipids, and Coronary Heart Disease. Retrieved from http://circ.ahajournals.org/conten/94/9/2337.full?ijkey=461a04097321c4af646235a3c4ca9a2dec26ecdc&keytype2=tf_ipsecsha on Sep. 17, 2014. Article originally published Jul. 1996.

Lee, K. Beware the 'other' Vitamin Supplement Ingredients. Retrieved from http://www.articlesbase.com/supplements-and-vitamins-articles/beware-the-other-vitamin-supplement-ingredients-551837.html on Sep. 17, 2014. Article originally published Sep. 8, 2007.

The Best Omega-3 brochure retrieved from http://thebestomega3.com/ on Sep. 17, 2014.

Vin Kutty, MS. Lovaza vs Fish Oil Supplements: A Side-by-Side Comparison. Retrieved from http://www.omegavia.com/lovaza-vs-fish-oil/ on Sep. 17, 2014. Article originally published Jun. 5, 2010.

"Microencapsulating fish oil" retrieved from http://www.biotechleam.org.nz/focus_stories/fish_oil_in_functional_food/microencapsulating_fish_oil on Sep. 17, 2014. Article originally published Jul. 17, 2009.

Product details for "PlusKenko" retrieved from http://www.miragedistribution.com/pluskenko.html on Sep. 17, 2014.

Product details for "ProOmega-D Xtra" retrieved from http://www.nordicnaturals.com/en/Products/Product_Details/515/?ProdiD=1618 on Sep. 17, 2014.

"The EPA/DHA Ratio in Fish Oil" retrieved from http://www.livestrong.com/article/495090-the-epa-dha-ratio-in-fish-oil/ on Sep. 17, 2014.

Product details for "WINOmeg3Complex" retrieved from http://winomega3.com/ on Sep. 17, 2014.

Product brochure for NovaSOL Omega retrieved from http://www.aquanova.de/media/public/pdf_produkte%20unkosher/NovaSOL_Omega_AAG_fin.pdf on Sep. 18, 2014.

Product Data Sheet for NovaSol Omega retrieved from http://www.aquanova.de/media/public/pds/PDS_EW0093_22_NovaSOL%20Omega.pdf on Sep. 18, 2014.

Product brochure for "Omega3 -6 -9 Emulsion" retrieved from http://web.archive.org/web/20131013023047/http:i/www.bio-genesis.com/productpages/omega-369-emulsion/omega-369-emulsion.html on Sep. 18, 2014.

Product brochure for NanoEPA DHA retrieved from http://web.archive.org/web/20121027093701/http://www.biopharmasci.com/content.cfm?n=products&id=8 on Sep. 18, 2014.

Product information for "Minami Nutrition Supercritical Omega 3 Fish Oils" retrieved from http://www.transformyourhealth.com/gardenoflife/minamiintroduction.html on Sep. 18, 2014.

Akyanda As. Bioavailability Study of Long Chain Omega-3 Fatty Acids From a Gastric Stable Emulsion. Retrieved from http://clinicaltrials.gov/show/NCT01061554 on Sep. 18, 2014.

Product Information for Sancilio & Company, Inc.'s Ocean Blue Pharmaceutical Grade Omega Power, Omega-3 Minicaps, Omega-3 +D3 Minicaps, and DHA Minicaps, May 30, 2013.

Product Information for Sancilio & Company, Inc.'s Ocean Blue Professional Omega-3 2100, Jul. 10, 2013.

Martin, CR et al., The safety and efficacy of oral docosahexaenoic acid supplementation for the treatment of primary sclerosing cholangitis—a pilot study; Aliment Pharmacol Ther. Author manuscript; PMC; Jan. 2012 Jul. 18; pp. 1-17.

SanGiovanni et al., ω-3 Long-chain polyunsaturated fatty acid intake and 12-y incidence of neovascular age-related macular degeneration and central geographic atrophy: AREDS report 30, a prospective cohort study from the Age-Related Eye Disease Study; The American Journal of Clinical Nutrition; Dec. 2009; pp. 1601-1607.

Lewis, Michael et al., Therapeutic use of omega-3 fatty acids in severe head trauma; Am J Emerg Med; Author manuscript; PMC, Jan. 2013; pp. 1-6.

Bougnoux, P. et al., Improving outcome of chemotherapy of metastic breast cancer by docosahexaenoic acid: a phase II trial; British Journal of Cancer (Nov. 2009), pp. 1978-1985.

Mills, James D. et al., Dietary Supplementation With the Omega-3 Fatty Acid Docosahexaenoic Acid in Traumatic Brain Injury; Neurosurgery, Issue: vol. 68(2), Feb. 2011, pp. 474-481.

Nobili, V. et al., Docsahexaenoic acid for the treatment of fatty liver: Randomised controlled trial in children; Nutrition, Metabolism & Cardiovascular Diseases (Dec. 2012) vol. 23, pp. 1066-1070.

Kelley, D.S. et al., DHA Supplementation Decreases Serum C-Reactive Protein and Other Markers of Imflammation in Hypertriglyceridemic Men; The Journal of Nutrition Nutrition and Disease; Jan. 2009; pp. 495-501.

Depner, C. M. et al.; Menhaden Oil Decreases High-Fat Diet-Induced Markers of Hepatic Damage, Steatosis, Inflammation, and Fibrosis in Obese Ldlr Mice; The Journal of Nutrition Nutrition and Disease; Jun. 2012; pp. 1495-1503.

Parker, Helen M. et al.; Omega-3 supplementation and non-alcoholic fatty liver disease: A systematic review and meta-analysis; Journal of Hepatology (2012) vol. 56; pp. 944-951.

Logan, Alan C.; Omega-3 fatty acids and major depression: A primer for the mental health professional; BioMed Central; Nov. 9, 2004; pp. 1-8.

Morishita, Mariko et al.; Pluronic® F-127 gels incorporating highly purified unsaturated fatty acids for buccal delivery of Insulin; International Journal of Pharmaceutics 212 (2001); pp. 289-293.

(56) References Cited

OTHER PUBLICATIONS

Product Information for Neptune Krill Oil's Unique Properties; Retrieved from http://www.nowfoods.com/Products/FAQs/081008.htm on Jul. 20, 2015.

Zanarini, Mary C. et al., Omega-3 Fatty Acid Treatment of Women With Borderline Personality Disorder: A Double-Blind, Placebo-Controlled Pilot Study; The American Journal of Psychiatry; Jan. 2003; 160,1: ProQuest Social Social Sciences Premium Collection; pp. 167-169.

Sallis, Hannah et al.; Perinatal depression and omega-3 fatty acids: A Mendelian randomisation study; Journal of Affective Disorders 166 (2014; pp. 124-131).

Richardson, Alexandra J. et al.; Docosahexaenoic Acid for Reading, Cognition and Behavior in Children Aged 7-9 Years: A Randomized, Controlled Trial (The DOLAB Study); PLoS One; Sep. 2012; vol. 7; Issue 9; pp. 1-14.

Lewis, Michael D. et al.; Suicide Deaths of Active Duty U.S. Military and Omega-3 Fatty Acid Status: A Case Control Companson; J Clin Psychiatry; Author manuscript; PMC Jan. 17, 2012; pp. 1-14.

Chew, Emily Y. et al.; The Age-related Eye Disease Study 2 (AREDS2); The American Academy of Ophthalmology (2012); pp. 2282-2289.

Nekkanti, V. et al.; Development of Novel Lipid Based Drug Delivery System for Raloxifene Hydrochloride; International Research Journal of Pharmacy; Sep. 6, 2012.

Davidson, Michael H. et al., A novel omega-3 free fatty acid formulation has dravatically improved bioavailability during a low-fat died compared with omega-3 acid ethyl esters: The Eclipse (Epanova.® Compared to Lovaza.RTM. in a pharmacokinetic single-dose evaluation) study; Journal of Clinical Lipidology, 2012, pp. 573-584, vol. 6.

Kajikawa, et al.; Highly Purified Eicosapentaenoic Acid Ethyl Ester Prevents Development of Steatosis and Hepatic Fibrosis in Rats; Dig Dis Sci 2010 55:631-641.

\* cited by examiner

* $p<0.05$

SELF-MICELLIZING FATTY ACIDS AND FATTY ACID ESTER COMPOSITIONS AND THEIR USE IN THE TREATMENT OF DISEASE STATES

CROSS REFERENCE TO RELATED APPLICATIONS

This application is a continuation of U.S. patent application Ser. No. 15/180,430 filed Jun. 13, 2016.

U.S. patent application Ser. No. 15/180,430 is a continuation of International Patent Application No. PCT/US15/54933, filed Oct. 9, 2015, which claims priority from U.S. Provisional Patent Application Nos. 62/062,638 filed Oct. 10, 2014; 62/062,643 filed Oct. 10, 2014; 62/062,646 filed Oct. 10, 2014; 62/062,652 filed Oct. 10, 2014; 62/062,634 filed Oct. 10, 2014; and 62/062,651 filed Oct. 10, 2014.

U.S. patent application Ser. No. 15/180,430 is also a continuation-in-part of U.S. patent application Ser. No. 14/808,876 filed on Jul. 24, 2015 (now U.S. Pat. No. 9,364,562 issued Jun. 14, 2016); Ser. No. 14/808,871 filed on Jul. 24, 2015 (now U.S. Pat. No. 9,375,490 issued Jun. 28, 2016); Ser. No. 14/808,866 filed on Jul. 24, 2015 (now U.S. Pat. No. 9,364,561 issued Jun. 14, 2016); Ser. No. 14/808,847 filed on Jul. 24, 2015 (now U.S. Pat. No. 9,364,560 issued Jun. 14, 2016); Ser. No. 14/808,835 filed on Jul. 24, 2015 (now U.S. Pat. No. 9,364,559 issued Jun. 14, 2016); Ser. No. 14/808,809 filed on Jul. 24, 2015 (now U.S. Pat. No. 9,364,558 issued Jun. 14, 2016); and Ser. No. 14/808,777 filed on Jul. 24, 2015 (now U.S. Pat. No. 9,370,585 issued Jun. 21, 2016); each of which is a continuation of U.S. patent application Ser. No. 14/456,750 filed on Aug. 11, 2014, now U.S. Pat. No. 9,302,017, which issued on Apr. 5, 2016; which is a continuation of International Patent Application No. PCT/US13/30211 filed on Mar. 11, 2013; which claims priority from U.S. Provisional Patent Application No. 61/618,161 filed on Mar. 30, 2012; the contents of each of which is herein incorporated by reference in its entirety.

U.S. patent application Ser. No. 15/180,430 is also a continuation-in-part of U.S. patent application Ser. No. 15/134,419 filed Apr. 21, 2016 (now abandoned); which is a continuation-in-part of U.S. patent application Ser. No. 14/578,692, filed Dec. 22, 2014, and now abandoned; which is a continuation-in-part of both U.S. patent application Ser. No. 14/456,731, filed Aug. 11, 2014, now U.S. Pat. No. 9,302,016, issued on Apr. 5, 2016 and Ser. No. 14/456,750, filed Aug. 11, 2014, now U.S. Pat. No. 9,302,017, issued on Apr. 5, 2016; which is a continuation of International Patent Application No. PCT/US13/30211 filed on Mar. 11, 2013; which claims priority from U.S. Provisional Application No. 61/618,161, filed on Mar. 30, 2012; the contents of each of which is herein incorporated by reference in its entirety.

U.S. patent application Ser. No. 15/180,430 is also a continuation-in-part of U.S. patent application Ser. No. 15/134,417 filed Apr. 21, 2016 (now abandoned); which is a continuation-in-part of U.S. patent application Ser. No. 14/578,697, filed Dec. 22, 2014, and now abandoned; which is a continuation-in-part of both U.S. patent application Ser. No. 14/456,731, filed Aug. 11, 2014, now U.S. Pat. No. 9,302,016, issued on Apr. 5, 2016 and Ser. No. 14/456,750, filed Aug. 11, 2014, now U.S. Pat. No. 9,302,017, issued on Apr. 5, 2016; which is a continuation of International Patent Application No. PCT/US13/30211 filed on Mar. 11, 2013; which claims priority from U.S. Provisional Patent Application No. 61/618,161, filed on Mar. 30, 2012; the contents of each of which is herein incorporated by reference in its entirety.

U.S. patent application Ser. No. 15/180,430 is also a continuation-in-part of U.S. patent application Ser. No. 15/132,278, filed Apr. 19, 2016 (now abandoned); which is a continuation-in-part of U.S. patent application Ser. No. 14/578,709, filed Dec. 22, 2014, and now abandoned; which is a continuation-in-part of both U.S. patent application Ser. No. 14/456,731, filed Aug. 11, 2014, now U.S. Pat. No. 9,302,016, issued on Apr. 5, 2016 and Ser. No. 14/456,750, filed Aug. 11, 2014, now U.S. Pat. No. 9,302,017, issued on Apr. 5, 2016; which is a continuation of International Patent Application No. PCT/US13/30211 filed on Mar. 11, 2013; which claims priority from U.S. Provisional Patent Application No. 61/618,161, filed on Mar. 30, 2012; the contents of each of which is herein incorporated by reference in its entirety.

U.S. patent application Ser. No. 15/180,430 is also a continuation-in-part of U.S. patent application Ser. No. 15/058,228, filed on Mar. 2, 2016 (now U.S. Pat. No. 9,480,651 issued Nov. 1, 2016); which claims priority from U.S. Provisional Patent Application No. 62/127,025, filed on Mar. 2, 2015, the contents of which is herein incorporated by reference in its entirety; and which is also a continuation-in-part of both U.S. patent application Ser. No. 14/456,731, filed Aug. 11, 2014, now U.S. Pat. No. 9,302,016, issued on Apr. 5, 2016 and Ser. No. 14/456,750, filed Aug. 11, 2014, now U.S. Pat. No. 9,302,017, issued on Apr. 5, 2016; which is a continuation of International Patent Application No. PCT/US13/30211 filed on Mar. 11, 2013; which claims priority from U.S. Provisional Patent Application No. 61/618,161, filed on Mar. 30, 2012; the contents of each of which is herein incorporated by reference in its entirety.

FIELD OF THE INVENTION

This invention relates to compositions including fatty acids, either in the triglyceride, ester, or free fatty acid forms, in combination with at least one surface active agent, and to the use of such compositions for the treatment of patients afflicted with various disease states. More particularly, this invention relates to self-micellizing compositions including at least one omega-3 fatty acid, which may be selected from the group consisting of hexadecatrienoic acid, α-linolenic acid, stearidonic acid, eicosatrienoic acid, eicosapentaenoic acid, heneicosapentaenoic acid, the omega-3 isomer of docosapentaenoic acid, also known as clupanodonic acid, docosahexaenoic acid, tetracosapentaenoic acid, and tetracosahexaenoic acid, in combination with a surface active agent composition effective to spontaneously form micelles with said fatty acids upon contact with an aqueous media. In certain embodiments, the self-micellizing compositions may further contain an omega-6 fatty acid (either in the triglyceride, ester, or free fatty acid form), for example arachidonic acid (ARA), linoleic acid (LA), gamma-linolenic acid (GLA) or the omega-6 isomer of DPA, also known as osbond acid. Most particularly, this invention relates to the treatment of various disease states by administering to a patient in need thereof the aforementioned compositions or pre-formed micelles produced therefrom.

In certain embodiments, the disease states may include (1) malabsorption syndromes, such as short bowel syndromes, which encompass a number of different clinical entities that may result in chronic diarrhea, abdominal distention, and failure to thrive; (2) primary sclerosing cholangitis (PSC), which is a chronic cholestatic liver disease characterized by progressive inflammatory and fibrotic destruction of the intrahepatic and/or extrahepatic bile ducts; (3) non-alcoholic fatty liver disease (NAFLD), which is characterized by increased hepatic fat accumulation in individuals not consuming excessive alcohol and represents a spectrum of disease ranging from 'simple' steatosis to non-alcoholic steatohepatitis; (4) sickle cell disease, which is a group of blood disorders that affects hemoglobin, the molecule that delivers oxygen throughout the body via red blood cells; (5) age-related macular degeneration (AMD), which is a condition that results in a loss of vision in the center of the visual field (the macula), and (6) neurodegenerative disease, which is an umbrella term for a range of conditions, which primarily affect the neurons in the human brain. Examples of neurodegenerative diseases contemplated for treatment by the present invention include, but are not limited to, Parkinson's Disease (PD), Alzheimer's Disease (AD), Amyotrophic Lateral Sclerosis (ALS or Lou Gehrig's Disease), Epilepsy, Bi-polar Syndrome, traumatic brain injury, peripheral neuropathy, and Multiple Sclerosis (MS).

BACKGROUND

Malabsorption Syndromes

Malabsorption syndromes encompass a number of different clinical entities that result in chronic diarrhea, abdominal distention, and failure to thrive. Clinical malabsorption can be broken down into several distinct conditions, both congenital and acquired, that affect one or more of the different steps in the intestinal hydrolysis and subsequent transport of nutrients.

Malabsorption is caused by a disorder in the intestinal processes of digestion and/or transport of nutrients across the intestinal mucosa into the systemic circulation. Either a congenital abnormality in the digestive or absorptive processes or, more commonly, a secondarily acquired disorder of such processes may result in malabsorption.

Neonates, young infants and adolescent humans with malabsorption syndromes, in particular fat malabsorption syndromes, are at particularly high risk for chronic diarrhea and malnutrition due to insufficient energy intake of high-energy value dietary lipids and essential lipids, which constitute building blocks for normal function of multiple body systems.

In some humans, exocrine pancreatic insufficiency is the principal condition that results in severe fat malabsorption. Pancreatitis, pancreatic cancer, pancreatic resection, cystic fibrosis, Shwachman-Diamond syndrome, Johnson-Blizzard syndrome, and Pearson syndrome can all result in pancreatic insufficiency. Significant obstructive biliary or cholestatic liver disease or extensive intestinal mucosal disease, such as occurs in celiac disease, may also result in severe steatorrhea.

One particular malabsorption syndrome is Short-Bowel Syndrome (SBS)—a disorder clinically defined by a failure to properly absorb nutrients (malabsorption), frequently accompanied by diarrhea, steatorrhea, fluid and electrolyte disturbances, edema, dehydration and malnutrition. Short-bowel syndrome has numerous causes, both congenital and acquired, but a common etiologic factor is the functional or anatomic loss of extensive segments of small intestine leading to a severe decrease in intestinal absorptive capacity. Adult human intestines have a normal length range of 260-88 cm. If disease, accident, or any other cause results in a loss of 50% of the small intestine or leaves less than 200 cm of viable length, a patient is at high risk of SBS.

The link between small intestine loss and short-bowel syndrome is simple, losing large amounts of the small intestine compromises the digestive and absorptive processes. Adequate digestion and absorption cannot take place and proper nutritional status cannot be maintained without supportive care, frequently including short term and long-term parenteral nutrition. In adults, SBS is commonly caused by radiation enteritis, mesenteric vascular accidents, trauma, and recurrent intestinal obstruction. In children, the most common causes are necrotizing enterocolitis, intestinal atresias, and intestinal volvulus. Other causes of SBS include congenital short small bowel, gastroschisis, and meconium peritonitis.

Whether or not a patient who has lost a significant amount of small intestine will develop SBS depends on a number of factors. Important cofactors that help to determine whether the syndrome will develop or not include the premorbid length of the small intestine, how much intestine is lost, the age of the patient, the remaining length of small intestine and colon, the functional quality of the residual bowel, and the presence or absence of the ileocecal valve.

Treatment of malabsorption syndromes, such as SBS, is mainly aimed at supplying the nutrients and vitamins that patients lack. It may include (a) a high-calorie diet that includes vitamins, minerals, carbohydrates, proteins, and fats; (b) injections of vitamins and minerals; (c) administration of drugs that slow down the normal movement of the small intestine; and (d) feeding through a vein (Total Parenteral Nutrition (TPN)).

Most SBS patients are initially fed with TPN. In many patients, intestinal adaptation, alone or in combination with dietary modifications, allows weaning from TPN. Unfortunately, many patients cannot be weaned from TPN.

Patients on long-term TPN frequently experience serious metabolic complications. The most common complications are hepatic and biliary disorders manifested by steatosis, fibrosis and cholestasis. These disorders can progress to fulminant liver failure. Prior to 2006, advanced liver disease was the most common cause of death in SBS patients. In infants with SBS, TPN-associated liver disease was estimated to occur in 40-60% of those receiving long-term TPN. This is largely due to the fact that infants are currently administered an intravenous solution of DHA, leading to liver injury, Mortality in infants who develop cholestasis is estimated to be as high as 80%. In accordance with the present invention, it is possible to significantly decrease this treatment-related morbidity by administering substantially pure DHA in combination with at least one surface active agent, as described herein, effective to spontaneously form a plurality of stable micelles having a particle size within a range of about 1 µm to about 10 µm upon contact with an aqueous medium, or alternatively, by administering preformed micelles produced therefrom, because the DHA avoids the first pass effect, the fatty acid is in the less toxic chylomicron form in blood, and there is no IV fistula issue.

Patients with malabsorption syndromes require products that safely and effectively deliver all essential nutrients. Many consider TPN-associated liver disease (PNALD) to be caused in part by the intravenous lipid emulsions used to provide fat calories in the PN formulation, although the etiology is unclear. It has been suggested that PNALD may be caused by inflammation that is related to the type of intravenous lipid emulsion used. These fat emulsions cannot be eliminated from PN because to do so would lead to the development of essential fatty acid deficiency and its concomitant complications. Recent data has shown that the replacement of omega-6 soybean oil lipid emulsions with those comprised primarily of omega-3 fatty acids may lead to reduction or avoidance of PNALD without predisposing the patient to essential fatty acid deficiency.

Given the limited treatment options currently available to patients with fat malabsorption syndromes and the associated side effects of these treatments, there is a need for alternative medications that can treat fat malabsorption syndromes. Ideally, such medications should provide the necessary and the essential fatty acids and fat calories for proper growth, development and maintenance of bodily functions in humans of all ages, but especially in neonates, and reduce or even avoid PNALD.

Primary Sclerosing Cholangitis

Primary sclerosing cholangitis (PSC) is a chronic cholestatic liver disease characterized by progressive inflammatory and fibrotic destruction of the intrahepatic and/or extrahepatic bile ducts. As the bile ducts become inflamed and narrow, bile backs into the liver causing liver cells to become inflamed. Over time this inflammation decreases blood flow within the liver, increasing pressure in the portal vein. As the disease progresses, liver cells die and are replaced with scar tissue.

The etiology of PSC is unknown, although, the association of PSC with inflammatory bowel disease, autoimmune diseases, and a host of other humoral and cellular immune abnormalities make an immunopathogenic mechanism likely.

Although the initial diagnosis of PSC is usually made within the fourth decade of life with a mean age of 40 years of age in men and 45 years in women, PSC is increasingly diagnosed in infants (in neonates, PSC is referred to as Neonatal Sclerosing Cholangitis (NSC)), children, and adolescents. PSC predominantly affects males. The diagnosis is based on characteristic findings in combination with clinical, biochemical and histological features. Many patients are asymptomatic at presentation, but symptoms develop over time. Symptoms include itch, lethargy, steatorrhea and vitamin deficiencies, metabolic bone disease, bleeding peristomal varices, bacterial cholangitis, dominant biliary strictures, and in advanced cases cholangiocarcinoma.

There is increasing evidence of a genetic predisposition to PSC, but the exact mechanism of susceptibility has not been well defined.

Immunosuppressants, chelators, and steroids are frequently used to help control the disease process, but have not shown any significant benefit. Ursodeoxycholic acid has been studied and may improve the liver function profile, but a high number of adverse events are associated with this treatment and there is debate about its effectiveness.

Genotype and phenotype analyses have shown that there is an increased prevalence of cystic fibrosis transmembrane conductance regulator protein (CFTR) abnormalities in adults with PSC. The CFTR protein functions as a channel for the movement of ions in and out of the epithelial cells lining exocrine glands. CFTR dysfunction is associated with (1) decreased chloride secretions into the bile canaliculi with subsequent decrease in osmotic extrusion of water into the lumen, resulting in hyperconcentration and acidification of bile leading to obstruction of intrahepatic bile ductules, secondary inflammation and eventual focal biliary cirrhosis; (2) innate immune defects and leads to an excessive host inflammatory response; (3) fatty acid alterations, specifically a decrease in docosahexaenoic acid (DHA) and an increase in arachidonic acid (AA). As CFTR dysfunction seems to be a contributing factor in the development of primary sclerosing cholangitis, targeting the correction of the fatty acid abnormalities and associated defects in immune defense and inflammatory responses seems to be a promising path in the treatment of PSC.

Omega-3 fatty acids are known to have anti-inflammatory effects. DHA in particular is known to be an important regulator of inflammation. It has been recently discovered that resolvins and protectins, two types of lipid mediators derived from DHA, modulate the inflammatory response by actively promoting the resolution of inflammation. DHA has been shown to correct fatty acid abnormalities and reverse the development of bile duct injury in $CFTR^{-/-}$ knockout mice. Recent data from a 12-month, open-label pilot study (n=23) to evaluate the safety and effectiveness of DHA for the treatment of PSC showed an increase in serum DHA levels and a significant decline in alkaline phosphatase in patients with PSC.

Currently there are no effective medical therapies for PSC that result in significant long-term improvement in outcome. Liver transplantation is the only life-extending therapy for patients with end-stage disease, with all of its associated risks, costs and complications. The median time from diagnosis to death or liver transplantation is 9-18 years. While different forms of medical treatment have been tried, there are no established, effective therapies that result in significant long-term improvements in outcome other than liver transplantation. Most treatments focus on monitoring liver function, managing symptoms and, when possible, temporarily opening blocked bile ducts. These therapies do not target the excessive inflammation and subsequent biliary tract fibrosis associated with the disease. Thus, there is clearly an unmet need for therapies, especially those that use omega-3 fatty acids, that can effectively target the inflammation and fibrosis associated with PSC and that therefore may prevent or limit disease progression.

Non-Alcoholic Fatty Liver Disease and Non-Alcoholic Steatohepatitis

Non-Alcoholic Fatty Liver Disease (NAFLD) is a common, often "silent" liver disease and resembles alcoholic liver disease, but occurs in people who drink little or no alcohol. The major feature of NAFLD is excess fat in the liver, along with inflammation and damage. Most people with this disease feel well and are not aware that they have a liver problem. Nevertheless, the condition can be severe and can lead to cirrhosis, in which the liver is permanently damaged and scarred and no longer able to function properly.

Non-alcoholic fatty liver disease (NAFLD) is characterized by increased hepatic fat accumulation in individuals not consuming excessive alcohol and represents a spectrum of disease ranging from 'simple' steatosis to non-alcoholic steatohepatitis. NAFLD is associated with the metabolic syndrome and is defined by the presence of ≥5% hepatic steatosis. Risk factors for the development of NAFLD include central obesity, type II diabetes, dyslipidemia, and hypertension. In Western populations, the prevalence of NAFLD may exceed 30%, and can be as high as 88% in the obese. NAFLD is the most common liver disease in children. Given the increasing prevalence and incidence of these conditions, the global burden of NAFLD is expected to increase.

Currently, NASH and NAFLD are under diagnosed due to poor disease awareness, the insufficiency of non-invasive diagnostic tools and the lack of effective approved therapies. As a confirmed diagnosis of NASH currently requires a liver biopsy, patients are often diagnosed after a blood test demonstrating elevated levels of liver enzymes, alanine aminotransferase (ALT), and aspartate aminotransferase (AST).

The primary treatment for NAFLD is weight loss by lifestyle therapy involving diet and exercise. Weight loss has been shown to improve liver enzymes, decrease plasma triglycerides and improve liver fatness. Bariatric surgery is an extreme option for reducing weight and the resulting improvements in liver pathology. However, bariatric surgery is not feasible for the large number of patients having this disease.

Treatments with insulin sensitizers, hypolipidemics and vitamin E have been shown to be ineffective due to poor patient compliance, associated weight gain, and side-effects. Although current evidence from available randomized control trials suggests that while thiazolidinediones and vitamin E are effective in reducing liver fat, there are serious safety concerns about long-term use of these agents.

Non-alcoholic steatohepatitis (NASH) is a fibrotic manifestation, which progresses from NAFLD. Like NAFLD, NASH is usually a silent disease with few or no symptoms and occurs in people who drink little or no alcohol. The major feature in NASH is fat in the liver, along with inflammation and damage. Most people with NASH feel well and are not aware that they have a liver problem. Nevertheless, NASH can be severe and can predispose the individual to hepatic fibrosis, cirrhosis, and subsequent end-stage liver disease and hepatocellular carcinoma. Not every person with NASH develops cirrhosis, but once serious scarring or cirrhosis is present, few treatments can halt the progression. A person with cirrhosis experiences fluid retention, muscle wasting, bleeding from the intestines, and liver failure. Liver transplantation is the only treatment for advanced cirrhosis with liver failure, and transplantation is increasingly performed in people with NASH. NASH ranks as one of the major causes of cirrhosis in the United States, behind hepatitis C and alcoholic liver disease.

Despite the rapidly increasing incidence of NASH, there are no therapies currently approved for the treatment of this common liver disorder. The NASH market has a significant unmet need for pharmacological options that are effective and well tolerated. Current options for managing patients with NASH are suboptimal and primarily rely on changes in lifestyle to reduce weight, off-label pharmacotherapy and bariatric surgery for weight loss. Weight loss is the first recommendation for NASH patients and is associated with a significant improvement in steatosis and overall severity of NASH. However, such improvement is only statistically significant when patients are able to reduce more than 7% of their body weight over a sustained period of 48 weeks, which occurs in less than 50% of NASH patients. Products utilized off label in the management of NASH comorbidities include vitamin E, insulin sensitizers such as metformin and pioglitazone, which are used for diabetic patients, and anti-hyperlipidemic agents, pentoxifylline, and ursodiol. High-dose vitamin E has been shown in a clinical study of non-diabetic patients to reduce inflammation but not fibrosis. Vitamin E is not recommended for NASH patients with type-2 diabetes due to lack of data, therefore the use of vitamin E is limited. While other off-label pharmacotherapies demonstrate inconsistent benefits or are associated with significant side effects. Bariatric surgery is believed to impact NASH through dramatic weight loss, but it has significant complications and drawbacks. These include a host of perioperative risk factors, the need to adhere to post-surgical diet and nutritional regimens and high costs. A relatively small number of these procedures are performed annually on NASH patients compared to the overall NASH population, which we believe is due to the complications and drawbacks of bariatric surgery relative to NASH patient numbers. We believe widespread increased adoption of bariatric surgery for NASH is impractical based on cost and the large number of patients who would require it. In addition, some retrospective and prospective studies have indicated that the procedure may worsen fibrosis. Liver transplant is a last resort for life-threatening complications progressing from NASH. NASH is currently the third most common reason for liver transplants in United States and is projected to surpass alcohol-based cirrhosis and viral hepatitis to become the leading indication for liver transplant by 2020. The availability of liver donors is extremely limited and the cost of a liver transplant is a significant economic burden, with an estimated cost per procedure of approximately $577,000. Studies have demonstrated that approximately 22% of patients do not survive the five-year period post-transplant. Therefore, a significant unmet need exists for alternative treatments for NAFLD and NASH.

While NAFLD occurs in people of all ages, NASH most often occurs in people who are middle aged and overweight or obese. Affected individuals may also have elevated levels of blood lipids (such as cholesterol and triglycerides) and many have diabetes. NASH affects 2 to 5 percent of Americans. Both NASH and NAFLD are becoming more common, possibly because of the greater number of Americans with obesity. In the past 10 years, the rate of obesity has doubled in adults and tripled in children. Obesity also contributes to diabetes and high blood cholesterol, which can further complicate the health of a patient with NASH.

There is no current approved treatment for NASH or NAFLD. Accordingly, medications for the treatment of NAFLD and/or NASH represent a substantial unmet need.

Sickle Cell Diseases

Sickle cell disease, also known as sickle-cell anaemia (SCA) and drepanocytosis, is a group of hereditary blood disorders that affects hemoglobin, the molecule that delivers oxygen throughout the body via red blood cells. Sickle cell disease is caused by mutations in the HbA gene and is inherited in an autosomal recessive pattern (a single point mutation in the sixth codon of the β-globin gene). There are four common genotypes associated with SCD-hemoglobin SS (HbSS), HbS beta0-thalassemia, hemoglobin SC (HbSC), and HbS beta+-thalassemia.

In individuals with two mutated genes, the resultant abnormal hemoglobin S polymerizes under low oxygen tension and causes abnormal red blood cells. Because of the polymerization, these cells frequently distort into a rigid sickle, or crescent, shape, in contrast to disc-shaped normal red blood cells. A person with a single abnormal copy does not experience symptoms and is said to have sickle-cell trait. A person with sickle cell trait inherits one normal allele and one abnormal allele encoding hemoglobin S (hemoglobin genotype AS). Sickle cell trait is generally regarded as a benign condition, although certain individuals with sickle cell trait may develop complications.

Sickle cell disease is a serious disease that significantly compromises the quality of patients' lives and reduces life expectancy significantly. Signs and symptoms of sickle cell disease usually begin in early childhood. The severity of symptoms varies from person to person and it has been postulated that clinical manifestations result from complex combinations of genetic, cellular and environmental factors. Some people have mild symptoms, while others are frequently hospitalized for more serious complications.

Sickle cells have a shorter lifespan than normal red blood cells. Sickle cells also deliver less oxygen to the body's tissues. As a result, patents with sickle cell disease frequently develop anemia. Sickle cell anemia is a common manifestation of sickle cell disease. Patients with anemia experience fatigue, weakness, shortness of breath, dizziness, headaches, and coldness in the hands and feet. Anemia can also cause delayed growth and development in children. The rapid breakdown of red blood cells may also cause jaundice.

Sickle cells are rigid and prone to adhesive interactions with each other, leukocytes, platelets, plasma and vessel walls. These adhesive interactions lead to vaso-occlusion in small blood vessels, with the sickle cells either intact or in pieces. Vaso-occlusion cuts down even more on the amount of oxygen flowing to body tissues. Acute vaso-occlusive events are known as crises. Crises can last from hours to days. Some patients have one episode every few years while others have many episodes each year. Crises can be severe enough to require hospitalization and can be fatal. Vaso-occlusive events in sickle cell disease are believed to be influenced by multiple factors, including leucocyte adhesion molecules, inflammatory factors, endothelial cell interactions, haemorheology and erythrocyte heterogeneity.

Three serious symptoms often accompany crises; pain, organ damage and infection. It is common in the relevant literature for researchers to also refer to "pain crisis" and "hemolytic (or "haemolytic") crisis" (rapidly evolving anemia, leukocytosis, jaundice and fever) and "fatty acid membrane abnormality" fatty as meaningful clinical endpoints.

Deprivation of oxygen-rich blood is especially deleterious to the lungs, kidneys, spleen, and brain. A particularly serious complication of sickle cell disease is pulmonary hypertension linked to blockages in the blood vessels that supply the lungs. Pulmonary hypertension occurs in about one-third of adults with sickle cell disease and can lead to heart failure.

Other serious consequences of the blocked blood vessels are strokes, ulcers of the lower extremities, impaired vision and priapism. Blockage of the blood vessels supplying the spleen may lead to failure of that organ, which results in serious infectious conditions such as osteomyelitis, cholecystitis, pneumonia and urinary tract infection.

As a result of the vaso-occlusion and organ damage, sickle cell patients are often in a near-continuous state of inflammation. They have elevated states of markers of inflammation such as C-reactive protein, fibrinogen and interleukin. Sickle cell patients also often have near continuous thrombotic activity, low level most of the time but spiking during crises.

There are numerous procedures performed to manage complications of sickle cell disease. These include blood transfusions, dialysis or kidney transplants, gallbladder removal, hip replacements for avascular necrosis, eye surgeries and wound care for leg ulcers. Bone marrow or stem cell transplants can cure sickle cell anemia, but are not an option for most patients because of a lack of well-matched stem cell donors. Ultimately, sickle cell disease causes multi-organ dysfunction and early death in affected individuals. Many succumb to complications of chronic organ dysfunction and eventual organ failure.

Unfortunately, for decades the root cause of sickle cell disease was misunderstood. Prior to very recently, the majority view was that sickle cell disease was merely the result of sickled red blood cells as a phenotypic manifestation of a single genetic point mutation. However, recent studies have shown that sickle cell disease is, in fact, a disease of systemic inflammation, inducing effects not only on the red blood cells, but also other blood cells and the vessels themselves. In fact, recent research has shown that red blood cells do not sickle in sickle cell disease patients until after a cascade of events occurs which leads to an increased stickiness of the blood cells and vessels.

Once the inflammation occurs, the red blood cells sickle, resulting in a feedback loop cascade, which increases the magnitude of the inflammation. This increased inflammation is manifested through the increased presence of arachidonic acid and a decrease in certain omega-3 acids, such as DHA. Thus, without being bound to any particular theory, it is believed that restoring the fatty acid compositions to nearer to normal levels will create a significant decrease in the inflammation and thus diminish the morbidity of sickle cell disease.

Unless a specific condition, disease state or malady associated with sickle cell disease is referenced herein, as used herein, a reference to "sickle cell disease" or "sickle cell condition" or "sickle cell disease condition" refers to each and all of the disease states and/or effects and/or conditions of sickle cell disease as described herein or as otherwise known by the ordinarily skilled artisan in the relevant art. A reference to "at least one sickle cell condition" refers to one or more of the conditions related to sickle cell disease as described herein or as otherwise known to such ordinarily skilled artisan.

Existing treatments for sickle cell disease are primarily aimed at relieving symptoms, limiting the number of crises and lessening complications. People with sickle cell disease need ongoing treatment, even when not having a crisis.

Frequently prescribed therapeutic compositions, thought to be of benefit for sickle cell patients, include pain medications, antibiotics, folic acid, hydroxyurea, and anti-inflammatory medications. Pain medicines of all types are heavily prescribed to address the pain episodes associated with sickle cell disease. Antibiotics are frequently prescribed to treat the bacterial infections that are common in sickle cell patients. Sickle cell patients are often advised to take folic acid supplements because folic acid aids in the production of new red blood cells.

Hydroxyurea (tradename DROXIA) is approved to reduce the number of pain episodes (including chest pain and breathing problems) and blood transfusions in patients with recurring moderate to severe crises but is a cytotoxic molecule with teratogenic and carcinogenic effects. The precise mechanism of action of hydroxyurea is uncertain. It has been found that besides the damage caused by sickle cells themselves, the inflammatory response that occurs in sickle cell disease patients could potentially play a significant role in the occurrence of painful episodes or pain crises. Sickle cell patients experience relief of symptoms when treated with a variety of anti-inflammatory agents.

As early as 1991, it was suggested that omega-3 fatty acids decrease the hemolysis of mammalian red blood cells. It also has been found that sickle cell patients have abnormal blood fatty acids. These findings have led to the hypothesis that omega-3 fatty acids may be useful in the treatment of sickle cell disease. As early as 2001, small human clinical trials showed that omega-3 fatty acids could reduce pain episodes in sickle cell patients, perhaps by reducing prothrombotic activity. Other studies have shown that omega-3 fatty acids can increase hemoglobin levels, and reduce pain episodes, vaso-occlusive episodes, anemia, organ damage and other disease complications in sickle cell patients.

Clupanodonic acid, also known as omega-3 DPA, is known to be useful as a platelet aggregation inhibitor and other omega-3 acids are known to possess anti-inflammatory properties. Vaso-occlusive events are the source of a number of problematic symptoms in patients with sickle disease and can occur through platelet aggregation as well as red blood cell aggregation and white blood cell aggregation. Some vaso-occlusive events are the result of thrombosis, which is initiated by thromboxane A2 (TXA2). Omega-3 DPA has been shown to be a potent inhibitor of COX-1 activity (the enzyme involved in synthesis of TXA2), thus omega-3 DPA can inhibit the pathways through which vaso-occlusive events occur. The studies above strongly suggest that omega-3 fatty acids can delay or even prevent some of the damaging effects of inflammation in sickle cell patients. Given the lack of effective drugs in treating sickle cell disease, there is a critical unmet need in developing new therapies for combatting this debilitating and life-shortening disease.

Accordingly, any new therapy that reduces the frequency or severity of inflammation, anemia and/or vaso-occlusive crises in patients is likely to play a useful role in the treatment of sickle cell disease. Given the observation that omega-3 fatty acids may be useful in the treatment of sickle cell disease and improving or protecting cell health, new formulations, particularly those with a demonstrable increase in absorption and blood levels of omega-3 and other fatty acids in the treatment of sickle cell disease are warranted.

Macular Degeneration

Age-related macular degeneration (AMD) is a condition that results in a loss of vision in the center of the visual field (the macula). It is a progressive disease and is the leading cause of severe vision loss in people over age 60. It occurs in "dry" and "wet" forms and causes damage to the macula, a small spot near the center of the retina and the part of the eye needed for sharp, central vision, which lets us see objects that are straight ahead.

The macula is the part of the retina that receives most of the direct light in the eye; is very sensitive to light, with higher concentrations of rods and cones, and is needed for accurate central vision. The retina is a network of visual receptors and nerves that lies on the choroid; a layer of blood vessels that provides blood to the macula, and the retinal pigment epithelium (RPE). The RPE is another layer of specialized cells, which transports the nutrients from the blood vessels and clears waste products from the macula.

Dry AMD is an early stage of the disease and may result from the aging and thinning of macular tissues due to the degeneration or atrophy that occurs from cell death. It is characterized by the presence of yellow spots, called drusen, which form in and around the macula. It is believed these spots are deposits or debris from deteriorating tissue, which accumulates between the retina and the choroid due to the inability of the RPE to get rid of the waste and leads to the eventual deterioration of the photoreceptors.

Wet AMD refers to the growth of abnormal growth of blood vessels (angiogenesis) beneath the retina, also referred to as choroidal neovascularization. These blood vessels leak blood and fluid into the retina, causing distortion of vision that makes straight lines look wavy, as well as blind spots and loss of central vision. These abnormal blood vessels eventually scar, leading to permanent loss of central vision.

Dry AMD occurs less often to people who exercise, avoid smoking and eat healthy food, including vegetables and fish. The National Eye Institute found in the Age-Related Eye Disease Studies (AREDS) that daily intake of a combination of vitamin C, vitamin E, beta-carotene, zinc, and copper can reduce the risk of late AMD by 25 percent and can slow progression of the disease. The AREDS2 trial found that adding lutein and zeaxanthin or omega-three fatty acids to the original AREDS formulation (with beta-carotene) had no overall effect on the risk of late AMD. However, the trial also found that replacing beta-carotene with a 5-to-1 mixture of lutein and zeaxanthin may help further reduce the risk of late AMD. While lutein and zeaxanthin appear to be safe regardless of smoking status of the individual suffering from AMD, high beta-carotene intake has been linked to an increased risk of lung cancer in current and former smokers. For wet AMD, angiogenesis inhibitors, such as for example, BEVACIZUMAB, RANIBIZUMAB, PEGAPTANIB, AND AFLIBERCEPT can be injected into one's eye to stop new blood vessels from growing.

Oxidative damage, resulting from excess production of reactive oxygen species (ROS) has been implicated in the progression AMD. Retinal pigmented epithelial (RPE) cells are highly metabolically active and there is strong evidence that the RPE cells are extremely sensitive to oxidative stress. It has been reported that the pathophysiology of AMD is due to cumulative oxidative damage to RPE cells resulting from an imbalance between the generation of ROS and the ability of these cells to destroy and/or protect against ROS damage. Strategies for protecting RPE cells against oxidative damage may be particularly important in maintaining retinal function and both preventing and treating AMD.

AREDS was designed to evaluate the prevention and treatment effects of high doses of antioxidants and zinc on individuals with AMD. AREDS2, was conducted to evaluate the effects on progression and treatment of AMD patients of a modified version of the AREDS formulation, including omega-3 fatty acids. The study showed no AMD-related benefit from the introduction of the omega-3 fatty acids into the treatment regimen. However, because the AREDS2 formulation did not include formulas with self-micellizing properties, the AREDS2 study was unable to evaluate an efficacious bioavailability of the omega-3 fatty acids on AMD. Furthermore, the AREDS2 study was unable to evaluate predictable, non-food dependent bioavailability of fat-soluble vitamins because said vitamins were not co-administered with self-micellizing formulations. Therefore, the benefits of administering omega-3 fatty acids with self-micellizing formulations would not have been recognized by previous studies.

The lack of any approved effective medications for AMD warrants the critical need for new therapies to treat AMD.

Neurodegenerative Diseases

Neurodegenerative disease is an umbrella term for a range of conditions, which primarily affect the neurons in the human brain. Examples of the more common neurodegenerative diseases include Parkinson's Disease (PD), Alzheimer's Disease (AD), Amyotrophic Lateral Sclerosis (ALS or Lou Gehrig's Disease), Epilepsy, and Multiple Sclerosis (MS).

PD is a neurodegenerative disorder primarily characterized by motor symptoms but which also includes several other pathological features such as autonomic system failures, mood disorders, and cognitive deficits. Conventional treatment may involve medication that is primarily aimed at increasing dopamine activity either by providing the precursor (raw material) in the form of levodopa (L-Dopa), or by stimulating dopamine receptors (essentially mimicking dopamine) through the use of a dopamine agonist drug. Also used are drugs called COMT inhibitors which can help the levodopa to be more effective and MAO-B inhibitors which prevent dopamine from breaking down so the limited supply is longer lasting. Other therapies may include physiotherapy, osteopathy, remedial movement, massage, speech therapy, psychological therapy and in some cases surgery (deep brain stimulation). Current pharmacological options for the disease are limited to symptom management and their long-term use leads to important side effects.

MS is a nervous system disease that affects your brain and spinal cord. It damages the myelin sheath, the material that surrounds and protects your nerve cells. This damage slows down or blocks messages between your brain and your body, leading to the symptoms of MS. They can include visual disturbances, muscle weakness, trouble with coordination and balance, sensations such as numbness, prickling, or "pins and needles", and thinking and memory problems. Although there is no known cure for multiple sclerosis, several therapies have proven helpful. The primary aims of therapy are returning function after an attack, preventing new attacks, and preventing disability. As with any medical treatment, medications used in the management of MS have several adverse effects. Available management and/or treatment of the disease is dependent on the stage of the disease. For example, in relapsing remitting multiple sclerosis (RRMS), eight disease-modifying treatments have been approved by regulatory agencies for RRMS including: interferon beta-la, interferon beta-1b, glatiramer acetate, mitoxantrone, natalizumab, fingolimod, teriflunomide and dimethyl fumarate. There is no treatment available, however, for primary progressive MS (PPMS).

ALS, is a rapidly progressive, neuromuscular disease. It attacks the motor neurons that transmit electrical impulses from the brain to the voluntary muscles in the body. When they fail to receive messages, the muscles lose strength, atrophy and die. RILUZOLE, which extends survival of ALS patients by several months, is currently the only treatment approved for improving survival, but does not reverse the damage already done to motor neurons. BACLOFEN and DIAZEPAM are often prescribed to control the spasticity caused by ALS, and trihexyphenidyl or amitriptyline may be prescribed when ALS patients begin having trouble swallowing their saliva.

AD is an irreversible, progressive brain disease that slowly destroys memory and thinking skills, and eventually even the ability to carry out the simplest tasks. AD is the most common cause of dementia among older people. Dementia is the loss of cognitive functioning—thinking, remembering, and reasoning—and behavioral abilities, to such an extent that it interferes with a person's daily life and activities. Dementia ranges in severity from the mildest stage, when it is just beginning to affect a person's functioning, to the most severe stage, when the person must depend completely on others for basic activities of daily living. Four medications are approved by the U.S. Food and Drug Administration to treat Alzheimer's. DONEPEZIL (ARICEPT®), RIVASTIGMINE (EXELON®), AND GALANTAMINE (RAZADYNE®) are used to treat mild to moderate Alzheimer's (donepezil can be used for severe Alzheimer's as well). MEMANTINE (NAMENDA®) is used to treat moderate to severe Alzheimer's. These drugs work by regulating neurotransmitters (the chemicals that transmit messages between neurons). They may help maintain thinking, memory, and speaking skills, and help with certain behavioral problems. However, these drugs don't change the underlying disease process, are effective for some but not all people, and may help only for a limited time.

Epilepsy is a group of neurological diseases characterized by epileptic seizures. Epileptic seizures are episodes that can vary from brief and nearly undetectable to long periods of vigorous shaking. In epilepsy, seizures tend to recur, and have no immediate underlying cause while seizures that occur due to a specific cause are not deemed to represent epilepsy. The cause of most cases of epilepsy is unknown, although some people develop epilepsy as the result of brain injury, stroke, brain tumor, and substance use disorders. Genetic mutations are linked to a small proportion of the disease. Epileptic seizures are believed to be the result of excessive and abnormal cortical nerve cell activity in the brain. Seizures are controllable with medication in about 70% of cases. In those whose seizures do not respond to medication, then surgery, neurostimulation, or dietary changes may be considered. The mainstay treatment of epilepsy is anticonvulsant medications, a number of which are available. Phenobarbital, phenytoin, carbamazepine and valproate appear to be equally effective in both partial and generalized seizures.

Current epidemiological, preclinical and clinical data suggest that omega-3 polyunsaturated fatty acids (n-3 PUFAs) may constitute therapeutic strategy for several disorders of the central nervous system, including PD, AD, ALS, Epilepsy, Bi-polar Syndrome, traumatic brain injury, peripheral neuropathy, and MS. These fatty acids, found most commonly in certain fish and some plants, are known to help reduce inflammation and oxidative stress on cells. Both of these processes are known to damage nerve tissue.

For example, the concentration of omega-3 fatty acids in nerve cell membranes has been shown to decrease with age, oxidant stress, and in neurodegenerative disorders such as Parkinson's disease. Researchers in Norway have presented evidence of a systematic omega-3 fatty acid deficit in PD and AD suggesting a fundamental neurological role for these vital fat molecules. Supplementation with the omega-3 DHA can favorably modify brain functions and has been proposed as a nutraceutical in PD and AD. More recently, the organization Overcoming Multiple Sclerosis (OMS) conducted a clinical trial looking for a link between omega-3 fatty acids and MS via the international HOLISM study. The findings strongly supported a link between consumption of fish and omega-3 supplements and better health for people with MS. Specifically, people with MS taking flaxseed oil regularly had over 60% fewer relapses than those who didn't in this large international sample. Association of fish consumption and omega-3 supplementation with quality of life, disability and disease activity has been studied in an international cohort of people with multiple sclerosis.

Similarly, recent studies show consumption of foods high in omega-3 fatty acids may help prevent or delay the onset of ALS.

The studies above strongly suggest that omega-3 fatty acids can delay or even prevent some neurodegenerative diseases. Given the lack of effective drugs in treating these diseases, there is a critical unmet need in developing new therapies for combatting at least certain neurodegenerative diseases.

Nutritional Deficiencies and their Effect on Disease State Manifestations

Studies have demonstrated that vitamin D may play a significant role in eye health, specifically in the prevention of AMD. A high correlation is known to exist between deficient vitamin D levels and AMD. Vitamin D is believed to act through the vitamin's anti-inflammatory or anti-angiogenic properties. For this reason, vitamin D may be useful in the treatment of multiple inflammation related diseases, including AMD, sickle cell disease, Alzheimer's, and other diseases.

Zinc is one of the most abundant trace metals in the human body. Over 300 enzymes are known to utilize zinc in normal mammalian function. Zinc deficiency affects many functions that are directly or indirectly related to declining cognitive performance in aging individuals, including the progression of Alzheimer's. Because zinc use is so prolific throughout the body, zinc deficiency can be causally related to Alzheimer's disease through multiple pathways. For instance, zinc deficiency can induce insulin resistance, a risk factor for Alzheimer's. Furthermore, zinc is believed to be very important in the transport of lipids across the intestinal lining and therefore affect many diseases related to lipid deficiencies, including Alzheimer's.

Alzheimer's disease represents a major health problem in the US, estimated to be the third leading cause of death, yet the causes of Alzheimer's disease remain largely unknown and misunderstood. However, recent research is beginning to demonstrate a clear link between the progression of the disease and certain changes in lipids, including fatty acids and fat soluble vitamins, as well as magnesium and zinc. Markers correlated with progression of Alzheimer's include changing fatty acid profiles of DHA, EPA, and arachidonic acid, as well as metabolic syndrome, chronic inflammation, hypovitaminosis D, and zinc deficiency. Furthermore, these markers themselves may be correlated.

Treatment of these correlated conditions can be made through the introduction of lipids in the correct ratios or amounts. However, because the absorption of lipids by the digestive system requires a co-consumption of the dietary fats necessary to form naturally occurring micelles, the ability to properly dose patients is often a significant challenge. Further complicating matters, the over-introduction of certain lipids, such as the fat-soluble vitamins, can be harmful. Therefore, a need exists to provide the necessary lipids in a manner which is diet-independent such that dosing can be more tightly controlled.

Magnesium contributes to more than three hundred chemical reactions in mammals, including every ATP-dependent reaction. Magnesium deficiency is most commonly associated with malabsorption diseases, including Crohn's disease, gluten-sensitive enteropathy (celiac disease), and regional enteritis. Resection or bypass of the small intestine, such as in short bowel disease, typically leads to malabsorption and magnesium loss. The interaction of magnesium and vitamin D is particularly important across a plethora of pathways and body systems. For example, magnesium is required for both steps in the activation of vitamin D to calcitriol, the form of the vitamin necessary for calcium absorption. Magnesium is also required for calcitriol's role in calcium absorption. Mammals with low magnesium are deficient in both vitamin D and calcitriol, but the introduction of calcitriol alone does not improve calcium absorption. Magnesium deficits are correlated to type 2 diabetes and insulin resistance as a result of higher excretion of magnesium that results from increased glucose concentrations in the kidneys. Thus, a need exists to co-administer magnesium with lipids in the treatment or prevention of certain disease states.

Vitamins A, D, and K cooperate synergistically not only with each other, but also with essential minerals like magnesium and zinc, with dietary fats. Vitamins A, D, and K2 interact synergistically to support immune health, support bone and teeth strengthening, and protect soft tissues from calcification. The interaction of these fat-soluble vitamins with magnesium and zinc is important. Zinc supports the formation of vesicles involved in transporting lipids, including the fat-soluble vitamins, across the intestinal wall.

SUMMARY OF THE INVENTION

Provided herein, in certain embodiments, are self-micellizing compositions comprising at least one omega-3 fatty acid composition (either in the triglyceride, ester, or free fatty acid form) and at least one surface active agent composition. These compositions, when combined in specific ratios, are characterized by their ability to spontaneously form a plurality of stable micelles within a range of about 1 µm to about 10 µm upon contact with an aqueous medium.

In order to determine sample size in a uniform and reproducible manner, all samples were characterized utilizing the LS™ 13 320 Aqueous Liquid Module (ALM).

The LS™ 13 320 Laser Diffraction Particle Size Analyzer uses laser diffraction and a patented polarization intensity differential scattering (PIDS) technology to rapidly determine the particle size distribution of materials with an overall sizing range of 0.04 µm to 2000 µm in a single scan with no extrapolation. This is accomplished with high resolution and excellent reproducibility.

In accordance with a standardized protocol, the sample was heated in its original container at 37° C. for one hour. After mixing well, approximately 0.25 g of sample was diluted with 5 mL of deionized water. The dilution was manually shaken to form a homogenous mixture. The preparation was allowed to equilibrate to room temperature and was subsequently dispensed to the ALM sample vessel dropwise and analyzed for the particle size distribution (PSD), which was determined using the Fraunhofer optical model. The instrument analyzed the PSD from 0.040 µm to 2,000 µm.

In certain embodiments, the at least one omega-3 fatty acid (either in the triglyceride, ester, or free fatty acid form) is selected from the group consisting of hexadecatrienoic acid, α-linolenic acid, stearidonic acid, eicosatrienoic acid, eicosapentaenoic acid, heneicosapentaenoic acid, the omega-3 isomer of docosapentaenoic acid, docosahexaenoic acid, tetracosapentaenoic acid, and tetracosahexaenoic acid. In certain embodiments, self-micellizing compositions may further contain an omega-6 fatty acid (either in the triglyceride, ester, or free fatty acid form), for example arachidonic acid (ARA), linoleic acid (LA), Gamma-linolenic acid (GLA), and omega-6 docosapentaenoic acid (omega-6 DPA).

Certain embodiments provide for at least one surface active agent, a first omega-3 fatty acid (either in the triglyceride, ester, or free fatty acid form) and a second omega-3 fatty acid (either in the triglyceride, ester, or free fatty acid form), wherein the first and second omega-3 fatty acids are different and are selected from the group consisting of hexadecatrienoic acid, α-linolenic acid, stearidonic acid, eicosatrienoic acid, eicosapentaenoic acid, heneicosapentaenoic acid, the omega-3 isomer of docosapentaenoic acid, docosahexaenoic acid, tetracosapentaenoic acid, and tetracosahexaenoic acid.

Certain embodiments provide for compositions comprising at least one surface active agent and a first omega-3 fatty acid (either in the triglyceride, ester or free fatty acid ester form) and a second omega-3 fatty acid (in either the ester, triglyceride or free fatty acid form), wherein the first and second omega-3 fatty acids are different and wherein the ratio of the amount of the first omega-3 fatty acid to the second omega-3 fatty acid is 1:X where 0<X<1. In certain other embodiments, X can be, for example, 0.001, 0.0015, 0.002, 0.0025, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.15, 0.2, 0.25, 0.55, 0.6, 0.65, 0.7, 0.75, 0.8, 0.85, 0.9, or, 0.95.

In certain embodiments, the compositions comprise at least one surface active agent and a first and second omega-3 fatty acid, wherein the first omega-3 fatty acid (in either the triglyceride, ester, or free fatty acid form) is docosahexaenoic acid (DHA) and the second omega-3 fatty acid (in either the triglyceride, ester, or free fatty acid form) is selected from the group consisting of hexadecatrienoic acid, α-linolenic acid, stearidonic acid, eicosatrienoic acid, eicosapentaenoic acid, heneicosapentaenoic acid, the omega-3 isomer of docosapentaenoic acid, tetracosapentaenoic acid, and tetracosahexaenoic acid and combinations thereof.

In certain other embodiments, the compositions comprise at least one surface active agent and a first and second omega-3 fatty acid, wherein the first omega-3 fatty acid (in either the triglyceride, ester, or free fatty acid form) is eicosapentaenoic acid (EPA) and the second omega-3 fatty acid (in either the triglyceride, ester, or free fatty acid form) is selected from the group consisting of hexadecatrienoic acid, α-linolenic acid, stearidonic acid, eicosatrienoic acid, heneicosapentaenoic acid, docosahexaenoic acid (DHA), the omega-3 isomer of docosapentaenoic acid (DPA), tetracosapentaenoic acid, and tetracosahexaenoic acid and combinations thereof.

In certain embodiments, the compositions comprise at least one surface active agent and a first and second omega-3 fatty acid, wherein the first omega-3 fatty acid (in either the triglyceride, ester, or free fatty acid form) is DHA and the second omega-3 fatty acid (in either the triglyceride, ester, or free fatty acid form) is EPA, wherein the ratio of the amount of DHA:EPA is 1:X, where 0<X<1. In certain other embodiments, X can be, for example, 0.001, 0.0015, 0.002, 0.0025, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.15, 0.2, 0.25, 0.55, 0.6, 0.65, 0.7, 0.75, or 0.8.

In certain embodiments, the compositions comprise at least one surface active agent and a first and second omega-3 fatty acid, wherein the first omega-3 fatty acid (in either the triglyceride, ester, or free fatty acid form) is EPA and the second omega-3 fatty acid (in either the triglyceride, ester, or free fatty acid form) is DHA, wherein the ratio of the amount of EPA:DHA is 1:X, where 0<X<1. In certain other embodiments, X can be, for example, 0.001, 0.0015, 0.002, 0.0025, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.15, 0.2, 0.25, 0.55, 0.6, 0.65, 0.7, 0.75, 0.8, 0.85, 0.9, or 0.95.

In certain embodiments, the compositions described herein optionally comprise a third fatty acid (either in the triglyceride, ester, or free fatty acid form), wherein the third fatty acid is different from the first and second omega-3 fatty acids. In such compositions, the ratio of the amount of the first omega-3 fatty acid to the second and third omega-3 fatty acids is 1:X, where X is the combined amount of the second and third fatty acids and where 0<X<1. For example, if the first omega-3 fatty acid is DHA and the second omega-3 fatty acid is EPA, the third omega-3 fatty acid may be selected from the group consisting of hexadecatrienoic acid, α-linolenic acid, stearidonic acid, eicosatrienoic acid, heneicosapentaenoic acid, the omega-3 isomer of docosapentaenoic acid, tetracosapentaenoic acid, and tetracosahexaenoic acid. The ratio of the amount of DHA:(EPA+third omega-3 fatty acid) is 1:X, where X is the amount of EPA plus the amount of the third omega-3 fatty acid, and where 0<X<1. In certain embodiments, X can be, for example, 0.001, 0.0015, 0.002, 0.0025, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.15, 0.2, 0.25, 0.3, 0.35, 0.4, 0.45, 0.5, 0.55, 0.6, 0.65, 0.7, 0.75, 0.8, 0.85, 0.9, or 0.95. In certain embodiments, the third fatty acid can be an omega-6 fatty acid such as arachidonic acid (ARA), linoleic acid (LA), gamma-linolenic acid (GLA) or the omega-6 isomer of DPA (either in the triglyceride, ester, or free fatty acid form).

In certain embodiments, the omega-3 fatty acids (either in the triglyceride, ester, or free fatty acid form) are substantially pure.

In certain embodiments, the omega-3 fatty acids are in the form of triglycerides.

In certain embodiments, the omega-3 fatty acids are in the form of esters.

In certain embodiments, the omega-3 fatty acid ester is the ethyl ester derivative.

In certain embodiments, the omega-3 fatty acids are in the form of free fatty acids.

In certain embodiments, the compositions comprising the at least one surface active agent and the omega-3 fatty acids in either the triglyceride or ester forms are free of free fatty acid forms.

In certain embodiments, the compositions are substantially free of active agents other than the omega-3 fatty acids (either in the triglyceride, ester, or free fatty acid form).

In certain embodiments, the omega-3 fatty acid or combinations of omega-3 fatty acids (in either the triglyceride, ester, or free fatty acid form) comprises, for example, 60%, 65%, 70%, 75%, 80%, 85%, 90% or 95% (wt/wt) of the composition.

In certain embodiments, the compositions described herein comprise DHA at, for example, from 50% to 99% (wt/wt) of the compositions. For example, in certain embodiments, the DHA is present at 50%, 55%, 60%, 65%, 70%, 75%, 80%, 85%, 90%, 95%, or 99% (wt/wt) of the compositions. In certain other embodiments, the DHA is present at least, for example, 90% (wt/wt) of the compositions described herein. In still other embodiments, the DHA is present at least, for example, 95% (wt/wt) of the compositions described herein.

In certain embodiments, the compositions described herein comprise EPA at, for example, from 0% to 50% (wt/wt) of the compositions. For example, in certain embodiments, the EPA is present at <1% (wt/wt) of said compositions. In certain other embodiments, the EPA can be present at, for example, 2%, 4%, 6%, 8%, 10%, 12%, 14%, 16%, 18%, 20%, 22%, 24%, 26%, 28%, 30%, 32%, 34%, 36%, 38%, 40%, 42%, 44%, 46%, 48% or 50% (wt/wt) of said compositions. In still other embodiments, the EPA can be present at <5% (wt/wt) of said compositions. For example, in certain embodiments, the EPA can be present at 0%, 0.1%, 0.2%, 0.3%, 0.4%, 0.5%, 0.6%, 0.7%, 0.8%, 0.9%, 1%, 1.5%, 2%, 2.5%, 3%, 3.5%, 4%, or 4.5% (wt/wt) of said compositions.

In certain embodiments, the compositions described herein comprise an omega-3 fatty acid other than DHA and EPA at, for example, from >0% to 10% (wt/wt) of said compositions. For example, said omega-3 fatty acid other than DHA and EPA can be present, in certain embodiments at 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, 5%, 5.5%, %, 6.5%, 7%, 7.5%, 8%, 8.5%, 9%, 9.5% or 10% (wt/wt) of said compositions. In such embodiments, the omega-3 fatty acid other than EPA and DHA can be selected from the group consisting of hexadecatrienoic acid, α-linolenic acid, stearidonic acid, eicosatrienoic acid, heneicosapentaenoic acid, the omega-3 isomer of docosapentaenoic acid, tetracosapentaenoic acid, and tetracosahexaenoic acid.

In certain embodiments, the compositions described herein comprise 90%, 5%, and 5% (wt/wt) of said compositions DHA, ARA, and EPA respectively.

In certain embodiments, the compositions described herein comprise 95%, 5%, and <1% (wt/wt) of said compositions DHA, ARA, and EPA respectively.

In certain embodiments, the omega-3 fatty acid compositions described herein comprise at least one surface active agent selected from the group consisting of at least one nonionic surface active agents, cationic surface active agents, anionic surface active agents, zwitterionic surface active agents, and combinations thereof.

In certain embodiments, the surface active agent is selected from the group consisting of at least one anionic surface active agent, at least one non-ionic surface active agent, and a combination thereof.

In certain embodiments comprising at least one surface active agent, the at least one surface active agent has a hydrophilic-lipophilic balance (HLB) of 8.0.

In certain embodiments comprising at least one surface active agent, the surface active agent can be a non-ionic surface active agent selected from the group consisting of at least one polysorbate, at least one poloxamer, and a combination thereof.

In certain embodiments, the at least one surface active agent comprises a polysorbate present from, for example, 15% (wt/wt) to 35% (wt/wt) of the composition.

In certain embodiments, the polysorbate is present at, for example, 31% (wt/wt) of the composition.

In certain embodiments, the polysorbate is polysorbate 80.

In certain other embodiments, the at least one surface active agent comprises a poloxamer present from, for example, 0.1% (wt/wt) to 5% (wt/wt) of the composition.

In certain embodiments, the poloxamer is present at, for example, 0.7% (wt/wt) of the composition.

In certain embodiments, the poloxamer is Poloxamer 237, also known as Pluronic® F87.

In certain embodiments, the compositions described herein comprise a combination of polysorbate 80 and the Poloxamer 237 (Pluronic® F87) [(HO(C$_2$H$_4$O)$_{64}$(C$_3$H$_6$O)$_{37}$(C$_2$H$_4$O)$_{64}$H].

In certain embodiments, the combination of polysorbate and poloxamer comprise at least, for example, 25% (wt/wt) of said composition.

In certain embodiments, the composition further comprises at least one antioxidant. In such embodiments the at least one antioxidant is selected from the group consisting of a tocopherol, a tocotrienol, and combinations thereof. In such embodiments, the tocopherol, tocotrienol and combinations thereof is present from, for example, from about 0.01% to about 5% by weight of the compositions. In certain such embodiments, the tocopherols, tocotrienols and combinations thereof can be present at, for example, 0.01%, 0.05%, 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, 5%, 5.5%, or 6% (wt/wt) of the compositions. In certain such embodiments, the tocopherols, tocotrienols, and combinations thereof can be present at, for example, 1%, 1.5%, 2%, 2.5%, 3%, 3.5%, 4%, 4.5%, 5%, 5.5%, or 6% (wt/wt) of the compositions. In certain embodiments further comprising at least one antioxidant, the antioxidant is d-gamma tocotrienol present at, for example, 3%, 3.35%, 4%, 4.35%, 5%, or 5.35% (wt/wt) of the composition. In certain embodiments further comprising at least one antioxidant, the antioxidant is α-tocopherol present at, for example, 2% (wt/wt) of the composition.

Certain embodiments provide for compositions comprising at least one terpene. Said present can be present from, for example, 0.1% (wt/wt) to 5% (wt/wt). In certain embodiments, the terpene is present at, for example, 0.01%, 0.05%, 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5% or 5% (wt/wt) of said composition. The terpene can be d-limonene.

In embodiments comprising substantially pure d-limonene, the d-limonene is from about, for example, 95% to about 98% pure. In certain embodiments, the substantially pure d-limonene is at least, for example, 95%, 96%, 97% or 98%, 99% pure.

Certain embodiments provide for compositions comprising natural orange-oil.

In certain embodiments, the bioavailability of the omega-3 fatty acids (in either the triglyceride, ester, or free fatty acid form) included in the compositions described herein is substantially the same when administered with or without food, i.e., substantially independent of food effect.

While not wishing to be bound to any particular theories, it has been observed that compositions comprising at least one omega-3 fatty acid (either in the triglyceride, ester or free fatty acid ester form) and at least one surface active agent, which are present in an amount and a combination effective to cause said compositions to self-micellize when in contact with an aqueous medium, can be characterized by their ability to spontaneously form a plurality of stable micelles having a particle size within a range of about 1 μm to about 10 μm, upon contact with the aqueous medium. The plurality of micelles produced in this manner demonstrate enhanced bioavailability of said at least one omega-3 fatty acid, while eliminating any food effect, and improving patient compliance due to the lowered dosage required to reach a similar bioavailability or AUC (e.g. 1 pill versus 6).

In at least one embodiment, a method is provided for treating AMD by administering the compositions described herein to a human in need of such administration. The human can be an adult, a child, an adolescent, or and infant, such as for example a neonate. In certain embodiments, a method is provided for treating Juvenile Macular Degeneration, which includes Stargardt's disease. Best disease, and juvenile retinoschisis by administering the compositions described herein to a human juvenile.

In certain embodiments, the compositions may comprise at least one omega-3 fatty acid, and at least one non-omega-3 fatty acid nutritional supplement agent, wherein the omega-3 fatty acid (in either the triglyceride, ester, or free fatty acid form) is docosahexaenoic acid (DHA) (in either the triglyceride, ester, or free fatty acid form) and wherein the non-omega-3 fatty acid active agent or non-omega-3 fatty acid nutritional supplement may be selected from the group consisting of vitamin C, vitamin E, beta-carotene, magnesium, zinc (including as zinc oxide), and copper (including as cupric oxide), and combinations thereof, and at least one surface active agent, in an amount and a combination effective to cause said compositions to spontaneously self-micellize when in contact with an aqueous medium, thereby forming a plurality of stable micelles having a particle size within a range of about 1 μm to about 10 μm.

In certain embodiments, the compositions comprise at least one surface active agent, at least one omega-3 fatty acid, and a non-omega-3 fatty acid active agent, wherein the omega-3 fatty acid (in either the triglyceride, ester, or free fatty acid form) is eicosapentaenoic acid (EPA) (in either the triglyceride, ester, or free fatty acid form) and wherein the non-omega-3 fatty acid active agent is selected from the group consisting of vitamin C, vitamin E, beta-carotene, magnesium, zinc (including as zinc oxide), and copper (including as cupric oxide), and combinations thereof.

In certain embodiments, the compositions comprise at least one surface active agent, a first omega-3 fatty acid, a second omega-3 fatty acid, and a non-omega-3 fatty acid active agent, wherein the first omega-3 fatty acid (in either the triglyceride, ester, or free fatty acid form) is EPA and the second omega-3 fatty acid (in either the triglyceride, ester, or free fatty acid form) is DHA, wherein the ratio of the amount of EPA:DHA is 1:X, where 0<X<1 and wherein the non-omega-3 fatty acid active agent is selected from the group consisting of vitamin C, vitamin E, beta-carotene, magnesium, zinc (including as zinc oxide), and copper (including as cupric oxide), arachidonic acid (ARA), linoleic acid (LA), gamma-linolenic acid (GLA) or the omega-6 isomer of DPA and combinations thereof.

Abnormal endothelial cell migration and proliferation can lead to adherent neovascularization. In the wet form of age-related macular degeneration (AMD), neovascularization can create severe vision problems. Current treatments include the use of known anti-angiogenesis medications. While not wishing to be bound to any particular theories, it is believed that compositions comprising omega-3 DPA can prevent angiogenesis through the vascular endothelial growth factor (VEGF) pathway.

In at least one embodiment, a method is provided for treating AMD by administering, to a patient in need thereof, a therapeutically effective amount of a composition comprising omega-3 DPA fatty acid (either in the triglyceride, ester or free fatty acid ester form) and at least one surface active agent, in an amount and a combination effective to cause said compositions to spontaneously self-micellize when in contact with an aqueous medium, thereby forming a plurality of stable micelles having a particle size within a range of about 1 μm to about 10 μm.

In at least one embodiment, a method is provided for treating fat malabsorption syndromes by administering the compositions described herein to a human in need of such administration. The human can be an adult, an adolescent, or and infant, such as for example a neonate.

In at least one embodiment, a method is provided for treating fat malabsorption syndrome by administering the compositions described herein to a human suffering from SBS or Barrett's Syndrome.

In at least one embodiment, a method is provided for treating sickle cell disease by administering the compositions described herein to a human in need of such administration. The human can be an adult, a child, an adolescent, or and infant, such as for example a neonate.

In at least one embodiment, a method is provided for treating NAFLD and/or NASH by administering the compositions described herein to a human in need of such administration. The human can be an adult, a child, an adolescent, or and infant, such as for example a neonate.

In at least one embodiment, a method is provided for treating neurodegenerative diseases, such as for example, Parkinson's Disease (PD), Alzheimer's Disease (AD), Multiple Sclerosis (MS), Epilepsy, and Amyotrophic Lateral Sclerosis (ALS), by administering the compositions described herein to a human in need of such administration. The human can be an adult, a child, an adolescent, or and infant, such as for example a neonate.

In at least one embodiment of the invention, a method is provided for preventing or treating Alzheimer's disease by administering the compositions described herein to a subject in need of such administration, wherein said compositions may include at least one fat-soluble vitamin, at least one omega-3 fatty acid (in triglyceride, ester, or free fatty acid form), one or more minerals, such as magnesium, manganese, zinc, copper, selenium, and combinations thereof, and at least one surface active agent in an amount and a combination effective to cause said compositions to spontaneously self-micellize when in contact with an aqueous medium, thereby forming a plurality of stable micelles having a particle size within a range of about 1 μm to about 10 μm.

In at least one embodiment of the invention, a method is provided for preventing or treating age-related macular degeneration by administering the compositions described herein to a subject in need of such administration, wherein said compositions may include at least one fat-soluble vitamin, an omega-3 fatty acid (in triglyceride, ester, or free fatty acid form, and one or more minerals, such as magnesium, manganese, zinc, copper, selenium, and combinations thereof, and at least one surface active agent in an amount and a combination effective to cause said compositions to spontaneously self-micellize when in contact with an aqueous medium, thereby forming a plurality of stable micelles having a particle size within a range of about 1 μm to about 10 μm.

In at least one embodiment of the invention, a method is provided for preventing or treating diseases by administering the compositions described herein to a subject in need of such administration, wherein said compositions may include at least one fat-soluble vitamin, an omega-3 fatty acid (in triglyceride, ester, or free fatty acid form), and one or more minerals, such as magnesium, manganese, zinc, copper, selenium, and combinations thereof, and at least one surface active agent in an amount and a combination effective to cause said compositions to spontaneously self-micellize when in contact with an aqueous medium, thereby forming a plurality of stable micelles having a particle size within a range of about 1 μm to about 10 μm., and wherein said diseases may include one or more of metabolic syndrome, chronic inflammation, hypovitaminosis D, zinc deficiency, Crohn's disease, diseases related to calcium deficiency, Alzheimer's disease, age-related macular degeneration, short bowel syndrome, sickle cell disease, irritable bowel syndrome, clotting disorders, hypertriglyceridemia, PSC, non-alcoholic fatty liver disease, epilepsy, age-related dementia, diabetic retinopathy, insulin resistance, diabetes, muscular dystrophy, microvillus inclusion disease (also known as Davidson's disease, congenital microvillus atrophy), intestinal epithelial dysplasia (IED), also known as tufting enteropathy, syndromic diarrhea (SD), also known as phenotypic diarrhea (PD) or tricho-hepato-enteric syndrome (THE), and cystic fibrosis.

In at least one embodiment of the invention, a method is provided for treating short bowel syndrome by administering the compositions described herein to a subject in need of such administration, wherein said compositions may include at least one fat-soluble vitamin, an omega-3 fatty acid (in triglyceride, ester, or free fatty acid form), and one or more minerals, such as magnesium, manganese, zinc, copper, selenium, and combinations thereof, and an omega-6 fatty acid (in triglyceride, ester, or free fatty acid form), for example arachidonic acid (ARA), linoleic acid (LA), gamma-linolenic acid (GLA) or the omega-6 isomer of DPA, and at least one surface active agent in an amount and a combination effective to cause said compositions to spontaneously self-micellize when in contact with an aqueous medium, thereby forming a plurality of stable micelles having a particle size within a range of about 1 µm to about 10 µm.

In certain embodiments, the compositions described herein self-micellize in an aqueous medium. In certain other embodiments, the aqueous medium is water. In certain other embodiments, the aqueous medium has an acidic pH. In certain other embodiments, the aqueous medium is 0.1N HCl.

In certain embodiments, the compositions described herein self-micellize in an aqueous medium, wherein the micelles have a diameter from about 1 µm to about 10 In certain embodiments, the compositions described herein self-micellizes in an aqueous medium having an acidic pH, wherein the micelles have a diameter from about 1 µm to about 10 In certain other embodiments, the compositions described herein self-micellizes in 0.1N HCL, wherein the micelles have a diameter from about 1 µm to about 10 In certain embodiments, the micelles may have an average diameter of about 1, 2, 3, 4, 5, 6, 7, 8, 9, or 10 µm.

In certain embodiments, the compositions described herein minimize or eliminate at least one side effect when compared to the administration of a composition comprising omega-3 fatty acids known to one of skill in the art. Non-limiting examples of the side effects include regurgitation, frequency of burping, gastroesophageal reflux disease (GERD), bloating, increased intestinal gas, fish taste, fishy breath, fish smell, nausea, diarrhea, or combinations thereof.

In certain embodiments, the compositions described herein comprise d-limonene or natural orange oil. Such compositions can minimize or eliminate at least one side effect from the administration of a composition of the present disclosure when compared to the administration of a composition comprising omega-3 fatty acids substantially free of d-limonene or natural orange oil. Non-limiting examples of the side effects include regurgitation, frequency of burping, gastroesophageal reflux disease (GERD), bloating, increased intestinal gas, fish taste, fishy breath, fish smell, nausea, diarrhea, or combinations thereof.

Certain embodiments of the compositions described herein can be administered to a human subject in need of such administration in conjunction with a non-omega-3 fatty acid nutritional supplement or a non-omega-3 fatty acid active agent for the treatment of macular degeneration. Non-limiting examples of non-omega-3 fatty acid nutritional supplements may include a combination of vitamin C, vitamin E, beta-carotene, zinc, copper, magnesium, manganese, calcium, vitamin A, vitamin D, vitamin K (includes K1 and/or K2), lutein and zeaxanthin.

Certain embodiments of the compositions described herein can be administered to a human subject in need of such administration in conjunction with a non-omega-3 fatty acid active agent for the treatment of SBS. Non-limiting examples of such non-omega-3 fatty acid active agents can include L-Glutamine (NUTRESTORE®), recombinant somatotropin (ZORBTIVE®), and teduglutide) (GATTEX®). Other such non-omega-3 fatty acid active agents may include conjugated bile acids or opium tincture.

Certain embodiments of the compositions described herein can be administered to a human subject in need of such administration, either alone, or in conjunction with a non-omega-3 fatty acid nutritional supplement or a non-omega-3 fatty acid active agent. For example, (1) in the treatment of a fat malabsorption syndrome, e.g. short bowel syndrome, a composition within the purview of the present invention will include substantially pure DHA, or a combination of substantially pure DHA and arachidonic acid in combination with a surface active agent which is a combination including about 31% of Polysorbate 80 and about 0.7% Poloxamer 237; (2) in the treatment of hypertriglyceridemia or hypocholesteremia, a composition within the purview of the present invention will include a combination of EPA and DHA, or a composition including EPA and a therapeutically effective amount of one or more statins, in combination with a surface active agent which is a combination including about 31% of Polysorbate 80 and about 0.7% Poloxamer 237; (3) in the treatment of non-alcoholic fatty liver disease (NAFLD) or non-alcoholic steatohepatitis (NASH), a composition within the purview of the present invention will include substantially pure DHA, in combination with a surface active agent which is a combination including about 31% of Polysorbate 80 and about 0.7% Poloxamer 237; (4) in the treatment of sickle cell disease (SCD), a composition within the purview of the present invention will include substantially pure DHA alone, substantially pure omega-3 DPA alone, or a combination of said DHA and DPA, in combination with a surface active agent which is a combination including about 31% of Polysorbate 80 and about 0.7% Poloxamer 237, in a therapeutically effective amount to treat sickle cell disease symptoms, such as vaso-occlusive events, sequestration crisis, avascular necrosis, stroke, and sickle cell anemia, among other known maladies, by decreasing the aggregation of platelets, red blood cells, and/or white blood cells.

Certain embodiments of the compositions described herein can be administered to a human subject in need of such administration in conjunction with a non-omega-3 fatty acid nutritional supplement or a non-omega-3 fatty acid active agent for the treatment of sickle cell disease. Non-limiting examples of non-omega-3 fatty acid active agents can include pain medications, antibiotics, a therapeutically effective amount of a non-steroidal anti-inflammatory medication, illustrated by, albeit not limited to a particular dosage of acetysalicylic acid (aspirin), hydroxyurea, and anti-inflammatory medications. Non-limiting examples of non-omega-3 fatty acid nutritional supplements may include a combination of folic acid, vitamin C, vitamin E, beta-carotene, zinc, copper, magnesium, manganese, calcium, vitamin A, vitamin D, vitamin K (includes K1 and/or K2), lutein and zeaxanthin.

Certain embodiments of the compositions described herein can be administered to a human subject in need of such administration in conjunction with a non-omega-3 fatty acid nutritional supplement or a non-omega-3 fatty acid active agent for the treatment of NAFLD and/or NASH. Non-limiting examples of non-omega-3 fatty acid active agents can include, lipid lowering or cholesterol lowering agents selected from the group consisting of cholesterol absorption inhibitors, bile acid sequestrants/resins, statins, niacin and derivatives, MTP inhibitors, fibrates and CETP inhibitors, insulin sensitizers, hypolipidemics, anti-inflammatory medications, and thiazolidinediones.

Certain embodiments of the compositions described herein can be administered to a human subject in need of such administration in conjunction with a non-omega-3 fatty acid nutritional supplement or a non-omega-3 fatty acid active agent for the treatment of PSC or Alagille Syndrome. Non-limiting examples of non-omega-3 fatty acid active agents can, upon approval by a respective regulatory agency, may include 6-alpha-ethylchenodeoxycholic acid and salts thereof, and/or (4R,5R)-1-[[4-[[4-[3,3-dibutyl-7-(dimethylamino)-2,3,4,5-tetrahydro-4-hydroxy-1,1-dioxido-1-benzothiepin-5-yl]phenoxy]methyl]phenyl]methyl]-4-aza-1-azoniabicyclo[2.2.2]octane chloride.

Certain embodiments of the compositions described herein can be administered to a human subject in need of such administration in conjunction with a non-omega-3 fatty acid nutritional supplement or a non-omega-3 fatty acid active agent for the treatment of a neurodegenerative disease. Non-limiting examples of non-omega-3 fatty acid active agents can include medications generally approved by a health regulatory body and prescribed by physicians for a particular neurodegenerative disease, such as for example, PD, AD, MS, Epilepsy, and ALS.

In certain embodiments, compositions including substantially pure DHA in combination with at least one surface active agent, as described herein, effective to spontaneously form micelles, or alternatively, pre-formed micelles produced therefrom, are effective for the treatment of neurodevelopmental psychiatric disorders, such as Attention Deficit Disorder (ADD) and Attention Deficit Hyperactivity Disorder (ADHD).

In at least one embodiment, the compositions described herein can be manufactured in an oil-filled inert, non-reactive vessel, non-limiting examples of which include glass vials and Teflon® coated vials; with or without light penetrating inhibitors, including for example amber colored vials. The composition in said oil-filled vial can be administered to an adult human, adolescent, or infant, in particular to a neonate, in need of such administration, by adding an appropriate amount of saline or other pharmaceutically acceptable solutions to said vial, thereby initiating the self-micellization process which results in the formation of the pre-formed micelles as defined herein. The homogenous solution, containing the pre-formed micelles, can then be either administered intravenously or added to infant formula for oral ingestion When administered orally, the compositions described herein may be administered in the form of a gel or liquid filled capsule.

Also provided are kits comprising compositions described herein as one or more unit dosage forms together with instructions on using the dosage forms. In certain embodiments, the dosage forms described herein can be packaged as unit doses, such as for example, glass crimp or snap top vials with instructions for using the unit dosage forms. For example, the instructions can be provided as a package insert or directly on a label attached to the vial, which can be made of clear or amber glass. The instructions can include, for example, dosing frequency recommendations, administration of the dosage forms with or without food, and the active ingredients comprising the dosage forms.

In certain embodiments kits are provided, wherein certain dosage forms comprising the compositions described herein can be packaged together with other non-omega-3 fatty acid nutritional supplements or active agents for the treatment of AMD. The kit(s) comprise one or more unit dosage forms of certain embodiments of the compositions described herein together with one or more unit dosage forms comprising the non-omega-3 fatty acid nutritional supplement or active agent for the treatment of AMD together with instructions on using the dosage forms. Non-limiting examples of non-omega-3 fatty acid nutritional supplements include, for example, a combination of vitamin C, vitamin E, beta-carotene, zinc, copper, magnesium, manganese, calcium, vitamin A, vitamin D, vitamins K1 and/or K2, lutein and zeaxanthin. Non-limiting examples of non-omega-3 fatty acid active agents include, for example, verteporfin; the antioxidant carotenoids crocin and crocetin, as found in, for example, Saffron (*Crocus sativus*) and inhibitors of angiogenesis, such as for example, BEVACIZUMAB (AVASTIN®), RANIBIZUMAB (LUCENTIS®), PEGAPTANIB (MACUGEN®) AND AFLIBERCEPT (EYLEA®).

Certain embodiments provide for a functional food(s) for treating AMD comprising the compositions described herein.

Certain embodiments provide methods of treating AMD by administering a functional food comprising the compositions described herein.

The instructions can include, for example, dosing frequency, administration of the dosage forms with or without food, the active ingredients comprising the dosage forms, and the fat malabsorption syndromes that would benefit from administration of the dosage forms.

In certain embodiments kits are provided, wherein certain dosage forms comprising the compositions described herein can be packaged together with other non-omega-3 fatty acid nutritional supplements for the treatment of a fat malabsorption syndrome. The kit(s) comprise one or more unit dosage forms of certain embodiments of the compositions described herein together with one or more unit dosage forms comprising the non-omega-3 fatty acid nutritional supplements for the treatment of a fat malabsorption syndrome together with instructions on using the dosage forms.

Certain embodiments provide for a functional food(s) for treating a fat malabsorption syndrome comprising the compositions described herein.

Certain embodiments provide methods of treating a fat malabsorption syndrome by administering a functional food comprising the compositions described herein.

In certain embodiments kits are provided, wherein certain dosage forms comprising the compositions described herein can be packaged together with other non-omega-3 fatty acid nutritional supplements or active agents for the treatment of sickle cell disease. The kit(s) comprise one or more unit dosage forms of certain embodiments of the compositions described herein together with one or more unit dosage forms comprising the non-omega-3 fatty acid nutritional supplement or active agent for the treatment of sickle cell disease together with instructions on using the dosage forms. Non-limiting examples of non-omega-3 fatty acid active agents and nutritional supplements that can be provided in the kits include pain medications, antibiotics, folic acid, hydroxyurea, and anti-inflammatory medications Certain embodiments provide for a functional food(s) for treating sickle cell disease comprising the compositions described herein.

Certain embodiments provide methods of treating sickle cell disease by administering a functional food comprising the compositions described herein.

In certain embodiments kits are provided, wherein certain dosage forms comprising the compositions described herein can be packaged together with other non-omega-3 fatty acid nutritional supplements or active agents for the treatment of NAFLD and/or NASH. The kit(s) comprise one or more unit dosage forms of certain embodiments of the compositions described herein together with one or more unit dosage forms comprising the non-omega-3 fatty acid nutritional supplement or active agent for the treatment of NAFLD and/or NASH together with instructions on using the dosage forms. Non-limiting examples of non-omega-3 fatty acid active agents that can be provided in the kits include, lipid lowering or cholesterol lowering agents selected from the group consisting of cholesterol absorption inhibitors, bile acid sequestrants/resins, statins, niacin and derivatives, MTP inhibitors, fibrates and CETP inhibitors, insulin sensitizers, hypolipidemics, anti-inflammatory medications, and thiazolidinediones.

Certain embodiments provide for a functional food(s) for treating NAFLD and/or NASH comprising the compositions described herein. Certain embodiments provide methods of treating NAFLD and/or NASH by administering a functional food comprising the compositions described herein.

In certain embodiments kits are provided, wherein certain dosage forms comprising the compositions described herein can be packaged together with other non-omega-3 fatty acid nutritional supplements or active agents for the treatment of PSC. The kit(s) comprise one or more unit dosage forms of certain embodiments of the compositions described herein together with one or more unit dosage forms comprising the non-omega-3 fatty acid nutritional supplement or active agent for the treatment of PSC together with instructions on using the dosage forms. Non-limiting examples of non-omega-3 fatty acid active agents that can, upon approval by a respective regulatory agency, be provided in the kits include 6-alpha-ethylchenodeoxycholic and/or (4R,5R)-1-[[4-[[4-[3,3-Dibutyl-7-(dimethylamino)-2,3,4,5-tetrahydro-4-hydroxy-1,1-dioxido-1-benzothiepin-5-yl]phenoxy]methyl]phenyl]methyl]-4-aza-1-azoniabicyclo[2.2.2]octane Chloride.

Certain embodiments provide for a functional food(s) for treating PSC comprising the compositions described herein.

Certain embodiments provide methods of treating PSC by administering a functional food comprising the compositions described herein.

In certain embodiments kits are provided, wherein certain dosage forms comprising the compositions described herein can be packaged together with other non-omega-3 fatty acid nutritional supplements or active agents for the treatment of neurodegenerative disease. The kit(s) comprise one or more unit dosage forms of certain embodiments of the compositions described herein together with one or more unit dosage forms comprising the non-omega-3 fatty acid nutritional supplement or active agent for the treatment of a neurodegenerative disease together with instructions on using the dosage forms. Non-limiting examples of non-omega-3 fatty acid active agents that can be provided in the kits include medications generally approved by a health regulatory body and prescribed by physicians for a particular neurodegenerative disease.

Certain embodiments provide for a functional food(s) for treating neurodegenerative diseases, such as for example, PD, AD, MS, Epilepsy, or ALS, comprising the compositions described herein.

Certain embodiments provide methods of treating neurodegenerative diseases, such as for example, PD, AD, MS, Epilepsy, or ALS, by administering a functional food comprising the compositions described herein.

DETAILED DESCRIPTION

Figure 1A:
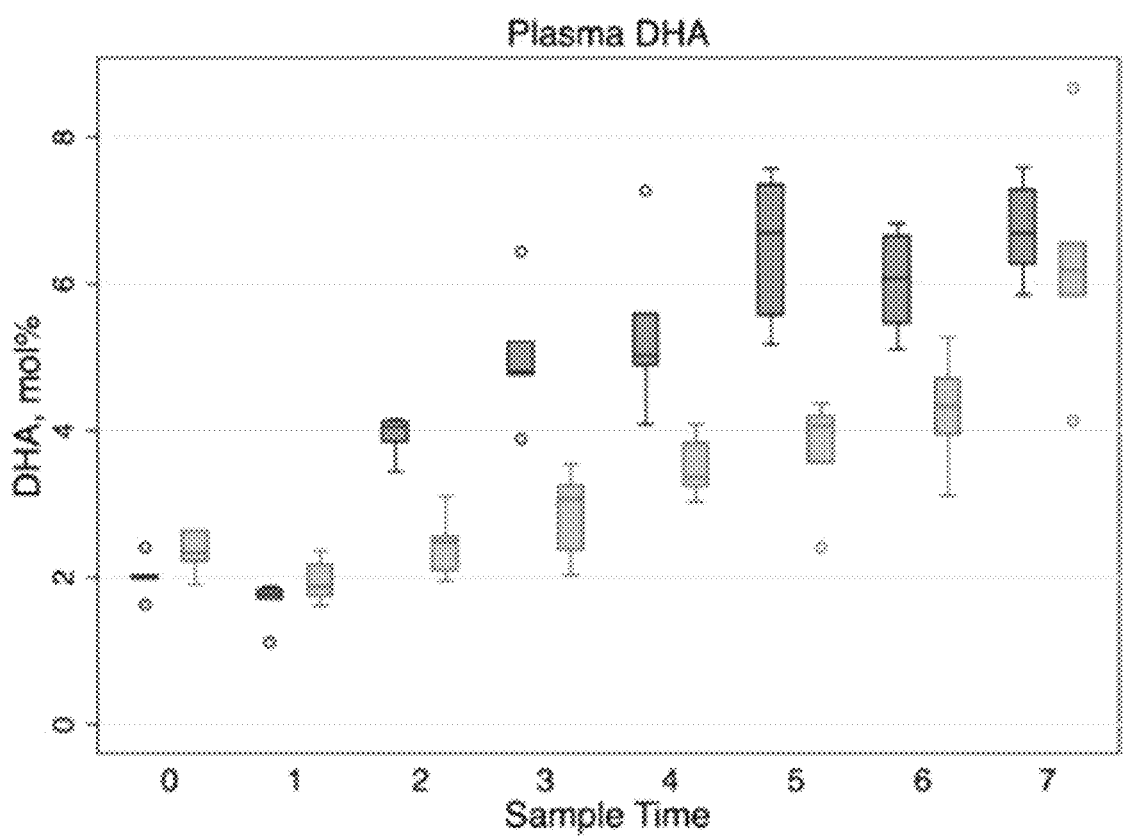
FIGS. 1A-1D illustrate plasma fatty acid profiles (mol %) in the SBS treatment group (dark gray) versus Control (light gray) groups. DHA: Docosahexaenoic acid; EPA: Eicosapentaenoic acid; AA: Arachidonic acid, LA, Linoleic acid. Sample time 0=day of surgery; 1=postoperative day (POD) 1/AM; 2=POD 1/PM; 3=POD 2/AM; 4=POD 2/PM; 5=POD 3/AM; 6=POD 3/PM; 7=POD 4/AM.
Figure 1B:
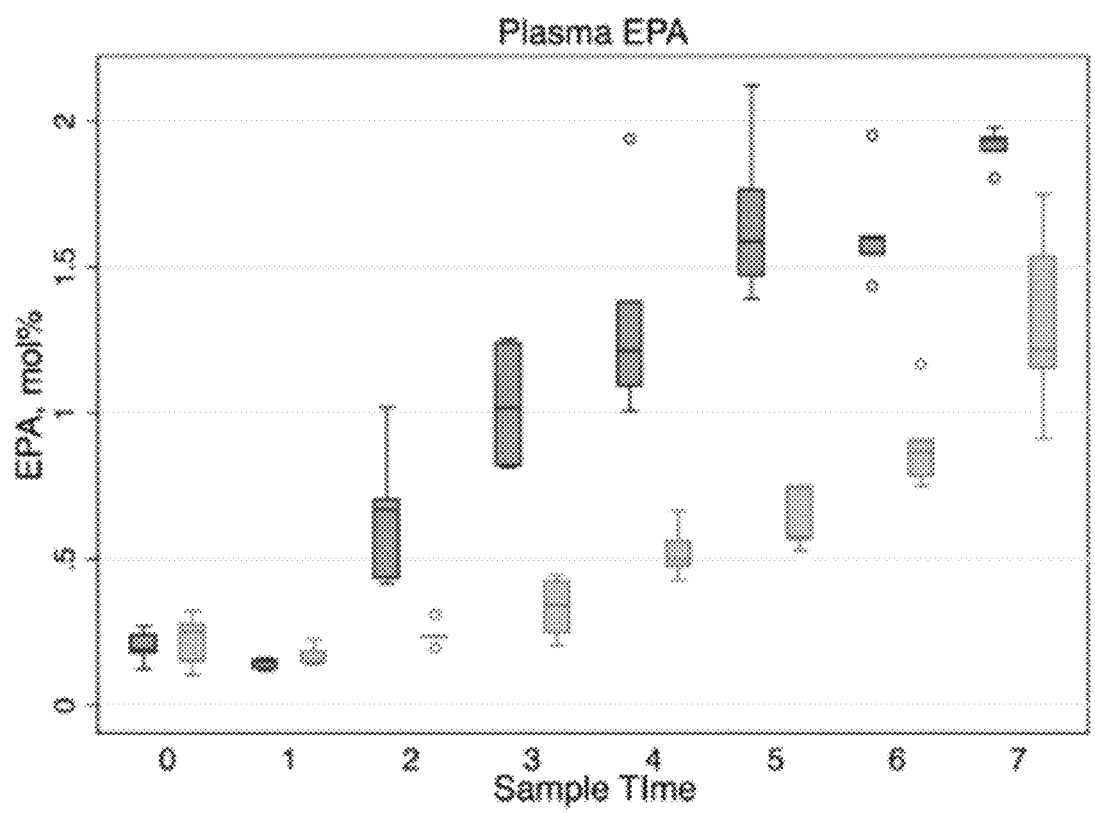
Figure 1C:
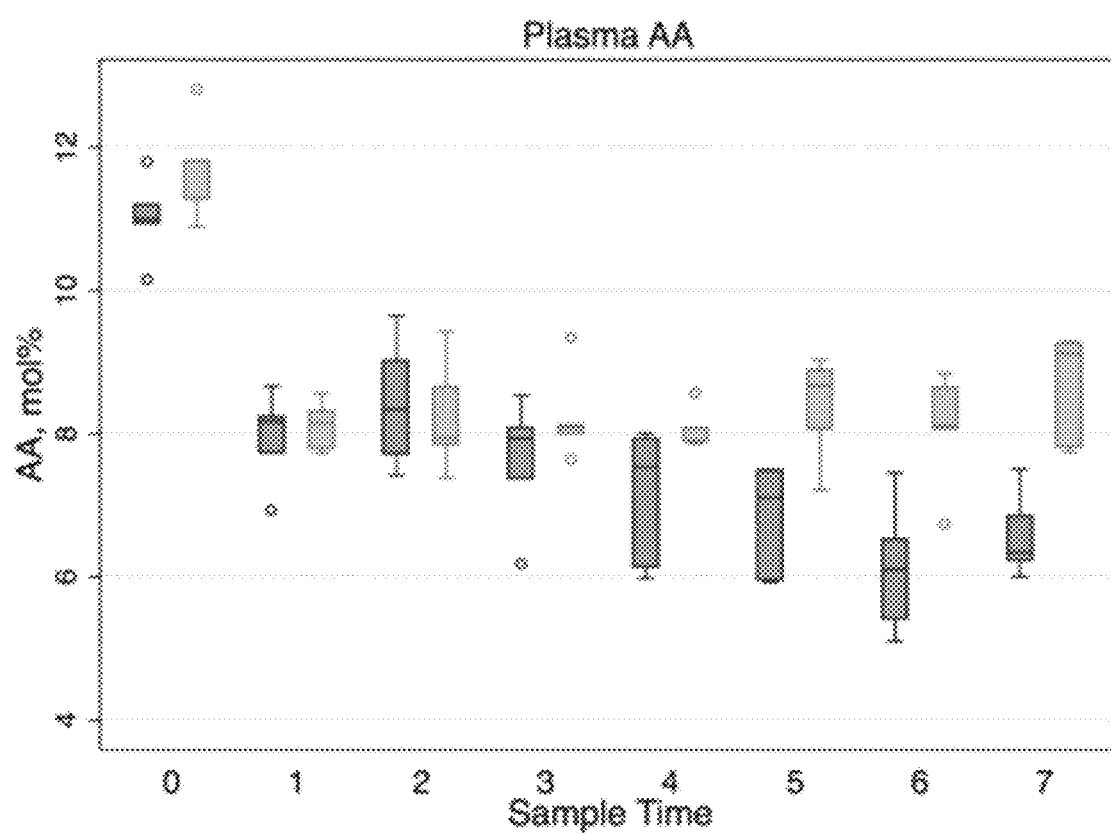
Figure 1D:
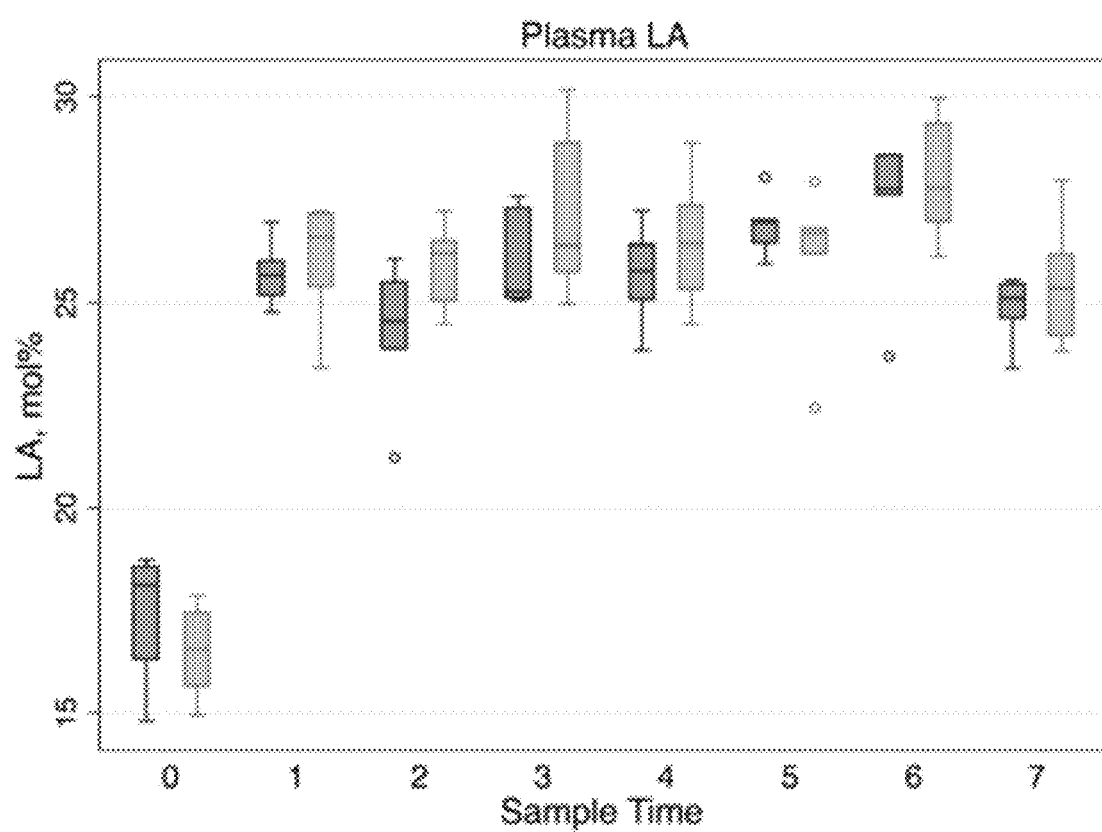
Figure 2A:
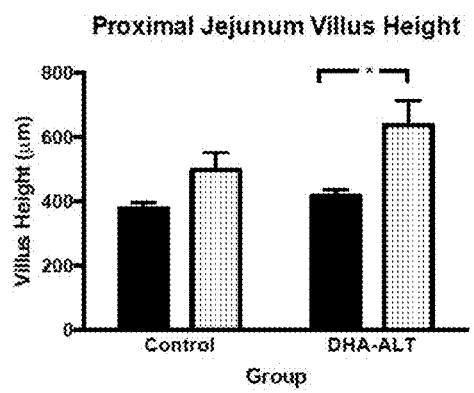
FIGS. 2A-2D illustrate intestinal morphology before and after surgical induction of SBS and DHA treatment. SBS: Short bowel syndrome; DHA: Docosahexaenoic acid; Black bars represent tissue morphometry from samples obtained at the time of surgery (Day 0); Striped bars represent tissue morphometry from samples obtained at the end of the study protocol (Final).
Figure 2B:
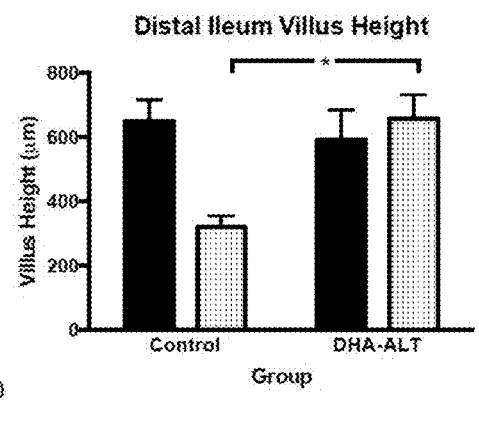
Figure 2C:
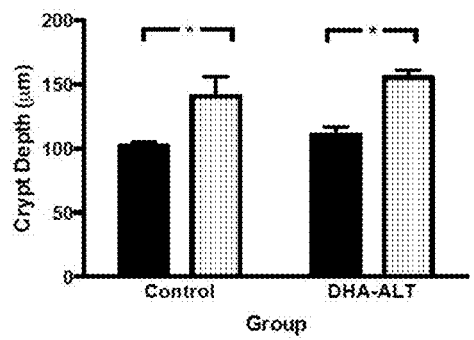
Figure 2D:
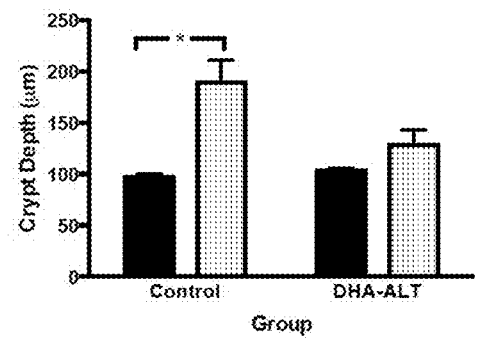

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under arty heading may be combined with embodiments illustrated under any other heading.

The various embodiments of the invention described herein may suitably comprise, consist essentially of, or consist of, at least one surface active agent, at least one omega-3 fatty acid (in either the triglyceride, ester, or free fatty acid form).

Certain embodiments of the invention may suitably comprise, consist essentially of, or consist of at least one surface active agent and a first and second omega-3 fatty acid, wherein the first omega-3 fatty acid (in either the triglyceride, ester, or free fatty acid form) is selected from the group consisting of hexadecatrienoic acid, α-linolenic acid, stearidonic acid, eicosatrienoic acid, eicosapentaenoic acid, heneicosapentaenoic acid, docosapentaenoic acid, docosahexaenoic acid, tetracosapentaenoic acid, tetracosahexaenoic acid, and combinations thereof and the second omega-3 fatty acid (in either the triglyceride, ester, or free fatty acid form) is selected from the group consisting of hexadecatrienoic acid, α-linolenic acid, stearidonic acid, eicosatrienoic acid, eicosapentaenoic acid, heneicosapentaenoic acid, docosapentaenoic acid, docosahexaenoic acid, tetracosapentaenoic acid, tetracosahexaenoic acid, and combinations thereof, wherein the first and second omega-3 fatty acids (in either the triglyceride, ester, or free fatty acid form) are different and wherein the ratio of the first omega-3 fatty acid (in either the triglyceride, ester, or free fatty acid form):the second omega-3 fatty acid (in either the triglyceride, ester, or free fatty acid form) is 1:X, where 0<X<0.3 or 0.5<X<1.

Certain embodiments of the invention may suitably comprise, consist essentially of, or consist of at least one surface active agent and a first and second omega-3 fatty acid, wherein the first omega-3 fatty acid (in either the triglyceride, ester, or free fatty acid form) is DHA and the second omega-3 fatty acid (in either the triglyceride, ester, or free fatty acid form) is selected from the group consisting of hexadecatrienoic acid, α-linolenic acid, stearidonic acid, eicosatrienoic acid, eicosapentaenoic acid, heneicosapentaenoic acid, docosapentaenoic acid, tetracosapentaenoic acid, tetracosahexaenoic acid, and combinations thereof, wherein the ratio of the amount of DHA to the second omega-3 fatty acid is 1:X, where 0<X<0.3 or 0.5<X<1.

Certain embodiments of the invention may suitably comprise, consist essentially of, or consist of at least one surface active agent and a first and second omega-3 fatty acid, wherein the first omega-3 fatty acid (in either the triglyceride, ester, or free fatty acid form) is EPA and the second omega-3 fatty acid (in either the triglyceride, ester, or free fatty acid form) is selected from the group consisting of hexadecatrienoic acid, α-linolenic acid, stearidonic acid, eicosatrienoic acid, heneicosapentaenoic acid, docosapentaenoic acid, docosahexaenoic acid, tetracosapentaenoic acid, tetracosahexaenoic acid, and combinations thereof, wherein the ratio of the amount of EPA to the second omega-3 fatty acid is 1:X, where 0<X<0.3 or 0.5<X<1.

Definitions

As used herein, the term "composition(s)" or "formulation(s)" includes therapeutic and dietary compositions including, but not limited to, a dietary supplement, nutraceutical formulation, or pharmaceutical formulation. Further, the terms composition, dietary supplement, nutraceutical formulation, and pharmaceutical formulation are used interchangeably herein.

As used herein, the term "EPA" refers inclusively to (5Z,8Z,11Z,14Z,17Z)-eicosa-5,8,11,14,17-pentaenoic acid or derivatives thereof, including alkyl esters, such as, for example, the ethyl ester.

As used herein, the term "DHA" inclusively refers to (4Z,7Z,10Z,13Z,16Z,19Z)-docosa-4,7,10,13,16,19-hexaenoic acid or derivatives thereof, including alkyl esters, such as, for example, the ethyl ester.

As used herein, the term "DPA" refers inclusively to docosapentaenoic acid (DPA), wherein "omega-3 DPA" refers to the omega-3 isomer all-cis-7,10,13,16,19-docosapentaenoic acid (clupanodonic acid) and "omega-6 DPA" refers to the omega-6 isomer all-cis-4,7,10,13,16-docosapentaenoic acid (osbond acid).

As used herein, the term "ARA" refers inclusively to (5Z,8Z,11Z,14Z)-Icosa-5,8,11,14-tetraenoic acid or derivatives thereof, including alkyl esters, such as, for example, the ethyl ester.

As used herein, the term linoleic acid "LA", refers inclusively to (9Z,12Z)-9,12-Octadecadienoic acid or derivatives thereof, including alkyl esters, such as, for example, the ethyl ester.

As used herein, the term "GLA" refers inclusively to all-cis-6,9,12-octadecatrienoic acid or derivatives thereof, including alkyl esters, such as, for example, the ethyl ester.

As used herein, the term "micelle" (plural micelles, micella, plurality of micelles, or micellae) refers to an aggregate of molecules, that have assembled into a substantially spherical core/shell architecture, and are suspended in an aqueous phase. A typical micelle in aqueous solution forms an aggregate with the hydrophilic "head" regions in contact with surrounding solvent and/or in contact with the polar region of one or more surface active agent(s), sequestering the hydrophobic regions in the micelle center. Micelles are approximately spherical in shape.

The term "self-micellizes" or "self-micellization" as used herein refers to the process in which micelles are formed in an aqueous medium without the introduction of energy, including agitation or shearing.

As used herein, the term "aqueous medium" refers to any solution or suspension, that comprises in part or in whole water, including for example, without limitation, water by itself; phosphate buffered saline at about pH 7.4, soft-drinks, illustrated by, albeit not limited to Sprite®, apple juice, G-2® fruit punch, infant formula or any equivalent mammalian mother's milk substitutes or analogues, intravenous fluid, and milk and milk products, including chocolate milk. In certain embodiments, an aqueous medium comprises at least one fluid having at least one fatty acid, carbohydrate, lipid, sugar, or combinations thereof. In certain embodiments, an aqueous medium comprises at least one fluid having an acidic pH. In certain other embodiments, an aqueous medium comprises a biological fluid such as, for example and without limitation, stomach acid. In other embodiments, the aqueous medium comprises simulated stomach acid comprising 0.1N HCl.

As used herein, the term "free fatty acid" refers to one or more polyunsaturated fatty acids that have not been modified or do not have any other groups attached.

As used herein, the term "ester" refers to the replacement of the hydrogen in the carboxylic acid group of a polyunsaturated fatty acid molecule with another substituent. Typical esters are known to those in the art, a discussion of which is provided by Higuchi, T. et al., *Pro-drugs as Novel Delivery Systems*, Vol. 14, A.C.S. Symposium Series, *Bioreversible Carriers in Drug Design*, Ed. Edward B. Roche, Amer. Pharma. Assoc., Pergamon Press (1987), and *Protective Groups in Organic Chemistry*, McOmie ed., Plenum Press, New York (1973), each of which is incorporated herein by reference in their entirety. Examples of common esters include methyl, ethyl, trichloroethyl, propyl, butyl, pentyl, tert-butyl, benzyl, nitrobenzyl, methoxybenzyl, benzhydryl, monoglyceride, diglyceride, triglyceride.

As used herein, the term "monoglyceride" refers to a fatty acid chain, such as DHA or EPA molecule, covalently bonded to a glycerol molecule through an ester linkage. As used herein, the term "diglyceride" refers to a fatty acid chain such as DHA or EPA, covalently bonded to a glycerol molecule through an ester linkage, wherein the glycerol molecule is further bonded to one additional fatty acid chain, which may or may not be DHA or EPA, through one additional ester linkage. As used herein, the term "triglyceride" refers to a fatty acid chain, such as DHA or EPA, covalently bonded to a glycerol molecule through an ester linkage, wherein the glycerol molecule is further bonded to two additional fatty acid chains, either or both of which may or may not be DHA or EPA, through two additional ester linkages.

As used herein, the term "terpene" refers to the large and diverse class of organic compounds produced by a variety of plants, particularly conifers. When terpenes are modified chemically, such as by oxidation or rearrangement of the carbon skeleton, the resulting compounds are generally referred to as "terpenoids" (e.g., carvone). Terpenes and terpenoids are the primary constituents of the essential oils of many types of plants and flowers.

As used herein, the terms "tocopherol", and "tocotrienol", and "vitamin E" refer to a set of fat-soluble vitamins with antioxidant properties. For example, the term "tocotrienol" refers to the family of tocotrienols "alpha-tocotrienol", "beta-tocotrienol", "gamma-tocotrienol" and "delta-tocotrienol". Similarly, the term "tocopherol" refers to the family of tocopherols "alpha-tocopherol", "beta-tocopherol", "gamma-tocopherol" and "delta-tocopherol".

As used herein, the term "antioxidant" refers to a molecule capable of inhibiting the oxidation of other molecules. Oxidation is a chemical reaction that transfers electrons or hydrogen from a substance to an oxidizing agent. Oxidation reactions can produce free radicals. In turn, these radicals can start chain reactions. When the chain reaction occurs in a cell, it can cause damage or death to the cell. Antioxidants terminate these chain reactions by removing free radical intermediates, and inhibit other oxidation reactions. They do this by being oxidized themselves, so antioxidants are often reducing agents such as thiols, ascorbic acid, or polyphenols. Exemplary antioxidants include rosemary oil, ascorbic acid (vitamin C), glutathione, lipoic acid, uric acid, carotenes, melatonin, ubiquinol (coenzyme Q), α-tocopherol (vitamin E), acorbyl palmitate, butylated hydroxyanisole, butylated hydroxytoluene, monothioglycerol, and potassium metabisulfite.

As used herein, a "pharmaceutically acceptable carrier" refers to any non-toxic amount of any substance suitable as a vehicle for delivering a molecule or composition to a suitable in vivo site of absorption. Examples of such carriers include, but are not limited to water, phosphate buffered saline (PBS), Ringer's solution, dextrose solution, serum-containing solutions, Hank's solution and other aqueous physiologically-balanced solutions.

As used herein, a "pharmaceutically acceptable preservative" includes but is not limited to a non-toxic amount of potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride.

As used herein, a "coloring agent" provides coloration to the composition or dosage form. Such coloring agents include, for example, food grade dyes.

As used herein, the term "subject" refers to a mammal, including but not limited to a dog, cat, horse, cow, pig, sheep, goat, chicken, rodent, primate or human. Subjects include animals such as house pets (e.g., dogs, cats, and the like), agricultural stock subjects (e.g., cows, horses, pigs, chickens, etc.), laboratory subjects (e.g., mice, rats, rabbits, etc.), but are not so limited. The human subject may be a pediatric, such as for example neonate, adult, or a geriatric subject. The human subject may be of either gender.

As used herein, an "effective amount" or "therapeutically effective amount" of a composition as described in some embodiments herein can be a quantity sufficient to achieve a desired therapeutic and/or prophylactic effect, for example, an amount which results in the prevention of, or a decrease in the symptoms associated with, a disease that is being treated. The amount of composition administered to the subject, particularly one in need of the composition, can depend on the type and severity of the disease and on the characteristics of the individual, such as general health, age, sex, body weight and tolerance to drugs. A person skilled in the art will be able to determine appropriate dosages depending on these and other factors. Typically, an effective amount of the compositions described herein can be sufficient for achieving a therapeutic or prophylactic effect.

In conjunction with the determination of a "therapeutically effective amount" of a particular modality, it is within the purview of the present invention to determine the presence of such a "therapeutically effective amount" by determining a quantity of a composition as described in some embodiments herein to modulate biomarkers related to a particular disease state. Such biomarkers may form a basis for surrogate endpoints for clinical trials, provide a basis for elucidating a better understanding of disease pathogenesis, and for quantifying the effectiveness of a therapeutic modality to down-regulate an inflammatory response, thereby quantifying disease progression.

Illustrative, albeit non-limiting biomarkers for several of the disease states effectively treated by the compositions of the present invention may include:

SCD

D-Dimer, to assess the coagulation rate, Total white blood cells and platelets, markers of inflammatory state, Lactate dehydrogenase (LDH), marker of intravascular hemolysis, Dense red blood cell fraction, marker of red blood cell sickling, Endothelin-1 (ET-1), soluble-VCAM-1 (sVCAM-1), soluble P-selectin (sP-selectin), markers of endothelial activation, interleukins (IL2, IL3, IL6, IL8 and IL10), urinary cysteinyl leucotriene E4 (28), and serum levels of prostaglandin-E2, CA 15-3, soluble CD40 ligand, HSP-70, ferritin, angiopoietin 1 and 2, stromal derived factor 1, tumor necrosis factor-α and tumor necrosis factor receptor-1.

NAFLD/NASH

CK18 M30, marker of NAFLD severity, IL-6, inflammatory state, Urine isoprostane, Oxidative stress, Livers spectroscopy, Fatty liver assessment PSC Calprotectin, Alkaline phosphatase—an elevated ALP is the most common biochemical abnormality in PSC, which often prompts clinicians to establish a diagnosis, reduction of ALP over time is associated with a favorable prognosis, Aspartate to alanine aminotransferase ratio: Aspartate aminotransferase (AST) and alanine aminotransferase (ALT) are markers of hepatocellular injury or necrosis, and elevation of AST or ALT is present in case of liver damage, Bilirubin: Bilirubin is routinely used in clinical practice as a measure of extrahepatic obstruction, Immunoglobulin G4: Measure of inflammation, inflammation results in fibrosis and deposition of connective tissue. PSC patients with elevated IgG4 have been shown to have a high prevalence of cirrhosis, and a shorter time to liver transplant, suggesting a more severe liver disease course.

It is contemplated to elucidate such biomarkers for any of the disease states treated herein, and to determine a therapeutically effective amount of a composition as it relates to its ability to modulate the pathogenesis of said disease state.

The terms "dose unit," "unit dose," and "dosage unit," as used herein, refer to a portion of a composition that contains an effective amount of an active suitable for a single administration to provide, or contribute to, a therapeutic effect. Such dosage units may be administered one to a plurality (i.e., 1 to about 10, 1 to about 8, 1 to about 6, 1 to about 4 or 1 to about 2) of times per day, or as many times as needed to elicit a therapeutic response.

The term "food effect," as used herein, refers to a relative difference in AUC (area under the curve), $C_{max}$ (maximum plasma concentration), and/or $T_{max}$ (time to maximum concentration) of an active substance, when said substance or a composition thereof, such as a tablet, a capsule or a liquid, is administered orally to a subject concomitantly with food or in a fed state as compared to the same values when the same composition is administered in a fasted state. The food effect, F, is calculated as:

$$F=(Y_{fed}-Y_{fasted})/Y_{fasted}$$

wherein $Y_{fed}$ and $Y_{fasted}$ are the found values of AUC, $C_{max}$, or $T_{max}$ in the fed and fasted state, respectively. A food effect, F, is generally established when F>1.

In general, the term "AUC" or "area under the plasma concentration-time curve" is related to the total amount of an active measurable in the systemic circulation following administration of a single dose. The AUC is a mathematical and visual representation of the aggregate amount of the active in the systemic circulation over a given period of time. Changes in the AUC need not necessarily reflect changes in the total amount of the active absorbed but can reflect modifications in the kinetics of distribution, metabolism and excretion. Accordingly, the term AUC as used herein refers to the total amount of omega-3 fatty acids (in either the triglyceride, ester, or free fatty acid form) measurable in the systemic circulation following administration of a single dose of any of the compositions described herein.

The term "$T_{max}$" or "time of peak concentration" refers to the period of time required to achieve peak plasma concentration of an active after administration of a single dose. Accordingly, the term $T_{max}$ as used herein refers to the period of time required to achieve peak plasma concentration of omega-3 fatty acid (in either the triglyceride, ester, or free fatty acid form) after administration of a single dose of any of the compositions described herein.

The term "$C_{max}$" or "peak concentration" is the highest concentration of an active achieved in the blood plasma. Accordingly, the term $C_{max}$ as used herein refers to the maximum concentration of omega-3 fatty acids (in either the triglyceride, ester, or free fatty acid form) after administration of a single dose of any of the compositions described herein.

The term "substantially independent of a food effect," or "substantially free of food effect" as used herein, refers to a significant elimination of the effect of food upon the absorption (e.g., F is about 0), following oral administration, of any of the compositions described herein. In other words, the bioavailability of the omega-3 fatty acids (in either the triglyceride, ester, or free fatty acid form), as measured by the logarithm-transformed $AUC_{0-\infty}$, is bioequivalent i.e., the 90% confidence interval should be within the acceptance range of 80% to 125% regardless of whether the compositions described herein are administered with or without food. In certain embodiments, the pharmacological effects of administration of compositions described herein are substantially independent of a food effect.

The term "reduced food effect," as used herein, refers to a substantial reduction in the effect of food upon the absorption, following oral administration, of any of the compositions described. In certain embodiments, the compositions described herein have a reduced food effect.

The term "concomitantly with food" or "administration in the fed state," as used herein, refers to administration from about 30 minutes before a meal to about 1 hour after a meal.

Various modes of treatment or prevention of medical conditions as described herein are intended to mean "substantial" or "substantially", which includes total but also less than total treatment or prevention, and wherein some biologically or medically relevant result is achieved. A subject, such as a human subject, in need of treatment refers to a subject in need of treatment of a defined disease state or in need of preventative treatment (i.e., prophylaxis) of such a disease state.

The use of numerical values in the various quantitative values specified throughout this disclosure, unless expressly indicated otherwise, are stated as approximations as though the minimum and maximum values within the stated ranges were both preceded by the word "about" unless expressly stated otherwise. In this manner, equivalent variations from a stated value can be used to achieve substantially the same results as the stated value. Also, the disclosure of ranges is intended as a continuous range including every value between the minimum and maximum values recited as well as any ranges that can be formed by such values. Also disclosed herein are any and all ratios (and ranges of any such ratios) that can be formed by dividing a recited numeric value into any other recited numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present invention.

The term "functional food" as used herein means any edible or drinkable foods or dietary components (e.g., infant formula, juices, milk, yogurt, butter, margarine, baking products) that are fortified or enhanced with any of the compositions described herein. The functional food can be, e.g., solid, liquid, semisolid, or a combination thereof. The term "functional food" also encompasses edible and drinkable nutritional supplements.

The term "hydrophilic-lipophilic balance" or "HLB," as used herein, refers to the relative affinity of a substance or composition for aqueous and oily phases. HLB values can be calculated based on methods and equations known to those of ordinary skill in the art, such as those described in U.S. Pat. No. 5,585,192. Substances or compositions generally have an average HLB of about 6 to about 20. Hydrophilic-lipophilic balance values can be determined in a variety of the formulas or experimental methods provided, for example, in U.S. Pat. No. 5,585,192.

The term "substantially pure" as used herein means at least 80% pure.

Pharmaceutical Compositions

In at least one embodiment, a composition is provided, wherein the composition comprises at least one omega-3 fatty acid and at least one surface active agent. In certain embodiments, the at least one omega-3 fatty acid is selected from the group consisting of hexadecatrienoic acid, α-linolenic acid, stearidonic acid, eicosatrienoic acid, eicosapentaenoic acid, heneicosapentaenoic acid, docosapentaenoic acid, docosahexaenoic acid, tetracosapentaenoic acid, and tetracosahexaenoic acid. Certain embodiments comprise more than one omega-3 fatty acid, which can be selected from the group consisting of hexadecatrienoic acid, α-linolenic acid, stearidonic acid, eicosatrienoic acid, eicosapentaenoic acid, heneicosapentaenoic acid, docosapentaenoic acid, docosahexaenoic acid, tetracosapentaenoic acid, and tetracosahexaenoic acid. The omega-3 fatty acid components comprising the composition are present at, for example, 60%, 65%, 70%, 75%, 80%, 85%, 90% or 95% (wt/wt) of the composition. The omega-3 fatty acids used herein are typically in the form of an oil.

In at least one embodiment, a composition is provided, wherein the composition comprises at least one isomer of docosapentaenoic acid (DPA) and at least one surface active agent, wherein the omega-3 DPA isomer is all-cis-7,10,13,16,19-docosapentaenoic acid (clupanodonic acid) or the omega-6 DPA isomer is all-cis-4,7,10,13,16-docosapentaenoic acid (osbond acid).

In certain embodiments, the compositions described herein comprise DHA at, for example, from 50% to 99% (wt/wt) of the compositions. For example, in certain embodiments, the DHA is present at 50%, 55%, 60%, 65%, 70%, 75%, 80%, 85%, 90%, 95%, or 99% (wt/wt) of the compositions. In certain other embodiments, the DHA is present at at least, for example, 90% (wt/wt) of the compositions described herein. In still other embodiments, the DHA is present at, at least, for example, 95% (wt/wt) of the compositions described herein.

In certain embodiments, the compositions described herein comprise EPA at, for example, from 0% to 50% (wt/wt) of the compositions. For example, in certain embodiments, the EPA is present at <1% (wt/wt) of said compositions. In certain other embodiments, the EPA can be present at, for example, 2%, 4%, 6%, 8%, 10%, 12%, 14%, 16%, 18%, 20%, 22%, 24%, 26%, 28%, 30%, 32%, 34%, 36%, 38%, 40%, 42%, 44%, 46%, 48% or 50% (wt/wt) of said compositions. In still other embodiments, the EPA can be present at <5% (wt/wt) of said compositions. For example, in certain embodiments, the EPA can be present at 0%, 0.1%, 0.2%, 0.3%, 0.4%, 0.5%, 0.6%, 0.7%, 0.8%, 0.9%, 1%, 1.5%, 2%, 2.5%, 3%, 3.5%, 4%, or 4.5% (wt/wt) of said compositions.

In certain embodiments, the compositions described herein comprise an omega-3 fatty acid other than DHA and EPA at, for example, from >0% to 10% (wt/wt) of said compositions. For example, said omega-3 fatty acid other than DHA and EPA can be present, in certain embodiments at 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, 5%, 5.5%, 6.5%, 7%, 7.5%, 8%, 8.5%, 9%, 9.5% or 10% (wt/wt) of said compositions. In such embodiments, the omega-3 fatty acid other than EPA and DHA can be selected from the group consisting of hexadecatrienoic acid, α-linolenic acid, stearidonic acid, eicosatrienoic acid, heneicosapentaenoic acid, docosapentaenoic acid, tetracosapentaenoic acid, and tetracosahexaenoic acid. In certain such embodiments, the third fatty acid other than DHA and EPA may be an omega-6 fatty acid, for example arachidonic acid (ARA), linoleic acid (LA), gamma-linolenic acid (GLA) or the omega-6 isomer of DPA.

In certain embodiments, the compositions described herein comprise 90%, 5%, and 5% (wt/wt) of said compositions DHA, ARA, and EPA respectively.

In certain embodiments, the compositions described herein comprise 95%, 5%, and <1% (wt/wt) of said compositions DHA, ARA, and EPA respectively.

The omega-3 fatty acid oils used in the manufacture of the compositions described herein are substantially pure. In some embodiments, the omega-3 fatty acid oils are at least, for example, 90% pure; and the remainder of the omega-3 fatty acids in the oil can comprise a mixture of other omega-3 fatty acids of which one omega-3 fatty acid may predominate the mixture. For example, if a composition comprises DHA oil, the DHA oil can be at least 90% DHA; and the remainder can comprise a mixture of omega-3 fatty acids, of which EPA can be the predominant omega-3 fatty acid and can be present at 5% of said composition. Accordingly, in omega-3 fatty acid oils, the ratio of the amount of the substantially pure omega-3 fatty acid, the first omega-3 fatty acid, to the predominant omega-3 fatty acid in the remaining fraction of the oil, the second omega-3 fatty acid, is 1:X, where 0<X<0.3 or 0.5<X<1. Thus, in certain embodiments, X can be, for example, 0.001, 0.0015, 0.002, 0.0025, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.15, 0.2, 0.25, 0.3, 0.55, 0.6, 0.65, 0.7, 0.75, or 0.8.

Thus, in at least one embodiment, the composition described herein comprises at least one surface active agent and a first and second omega-3 fatty acid, wherein the first omega-3 fatty acid is DHA and the second omega-3 fatty acid EPA, wherein the ratio of the amount of DHA:EPA is 1:X, where 0<X<0.3 or 0.5<X<1. In certain other embodiments, X can be, for example, 0.001, 0.0015, 0.002, 0.0025, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.15, 0.2, 0.25, 0.55, 0.6, 0.65, 0.7, 0.75, or 0.8.

In other embodiments, the compositions described herein comprise at least one surface active agent and a first and second omega-3 fatty acid, wherein the first omega-3 fatty acid is EPA and the second omega-3 fatty acid is DHA, wherein the ratio of the amount of EPA:DHA is 1:X, where 0<X<0.3 or 0.5<X<1. In certain other embodiments, X can be, for example, 0.001, 0.0015, 0.002, 0.0025, 0.0055, 0.006, 0.0065, 0.007, 0.0075, 0.008, 0.0085, 0.009, 0.0095, 0.01, 0.015, 0.02, 0.025, 0.03, 0.055, 0.06, 0.065, 0.07, 0.075, 0.08, 0.085, 0.09, 0.095, 0.1, 0.15, 0.2, 0.25, 0.55, 0.6, 0.65, 0.7, 0.75, or 0.8.

In certain embodiments, the compositions described herein can optionally comprise a third omega fatty acid (either in the triglyceride, ester, or free fatty acid form), wherein the third omega fatty acid is different from the first and second omega fatty acids. In such compositions, the ratio of the amount of the first omega fatty acid to the second and third omega fatty acids is 1:X, where X is the combined amount of the second and third omega fatty acids and X is 0<X<1. For example, if a composition comprises DHA oil, the DHA oil can be at least, for example, 90% DHA (the first omega fatty acid); and the remaining 10% can comprise a mixture of omega fatty acids, of which EPA can be the predominant omega fatty acid (second omega fatty acid) and can be present at 5% of said composition. The third omega fatty acid is selected from the group consisting of hexadecatrienoic acid, α-linolenic acid, stearidonic acid, eicosatrienoic acid, heneicosapentaenoic acid, docosapentaenoic acid, tetracosapentaenoic acid, and tetracosahexaenoic acid. In certain embodiments the third omega acid may be an omega-6 fatty acid. Accordingly, in such embodiments, if the first omega fatty acid is DHA and the second omega fatty acid is EPA, The ratio of the amount of DHA:(EPA+third omega fatty acid) is 1:X, where X is the amount of EPA and the amount of the third omega fatty acid, and where 0<X<1. In certain embodiments, X can be, for example, 0.001, 0.0015, 0.002, 0.0025, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.15, 0.2, 0.25, 0.3, 0.35, 0.4, 0.45, 0.5, 0.55, 0.6, 0.65, 0.7, 0.75, 0.8, 0.85, 0.9, or 0.95. In certain embodiments, the third fatty acid can be arachidonic acid (ARA) (either in the triglyceride, ester, or free fatty acid form). In certain embodiments, the ARA is in the ethyl ester form.

In some embodiments, the omega-3 or omega-6 fatty acid compositions described herein are in either the triglyceride, ester, or free fatty acid form. Typically, but not necessarily, the omega-3 or omega-6 fatty acid is in the ester form, particularly in the ethyl ester form.

In certain embodiments, the compositions comprise at least one surface active agent and a first and second omega-3 fatty acid, wherein the first omega-3 fatty acid (in either the triglyceride, ester, or free fatty acid form) is omega-3 docosapentaenoic acid (omega-3 DPA) and the second omega-3 fatty acid (in either the triglyceride, ester, or free fatty acid form) is selected from the group consisting of docosahexaenoic acid (DHA), eicosapentaenoic acid (EPA), hexadecatrienoic acid, α-linolenic acid, stearidonic acid, eicosatrienoic acid, eicosapentaenoic acid, heneicosapentaenoic acid, docosapentaenoic acid, tetracosapentaenoic acid, and tetracosahexaenoic acid and combinations thereof.

In certain embodiments, the compositions comprise at least one surface active agent, an omega-6 fatty acid, and an omega-3 fatty acid, wherein the omega-6 fatty acid (in either the triglyceride, ester, or free fatty acid form) is for example arachidonic acid (ARA), linoleic acid (LA), gamma-linolenic acid (GLA) or the omega-6 isomer of DPA, and the second omega-3 fatty acid (in either the triglyceride, ester, or free fatty acid form) is selected from the group consisting of omega-3 docosapentaenoic acid (omega-3 DPA), docosahexaenoic acid (DHA), eicosapentaenoic acid (EPA), hexadecatrienoic acid, α-linolenic acid, stearidonic acid, eicosatrienoic acid, eicosapentaenoic acid, heneicosapentaenoic acid, docosapentaenoic acid, tetracosapentaenoic acid, and tetracosahexaenoic acid and combinations thereof.

In certain embodiments the omega-3 fatty acid (in either the triglyceride, ester, or free fatty acid form) may be DHA, for example substantially pure DHA, in combination with arachidonic acid in a ratio of DHA to arachidonic acid of 1:1 to 20:1. In certain embodiments, α-linolenic acid may be included for its anti-inflammatory properties.

In certain embodiments, the compositions described herein are free of free fatty acids.

In certain embodiments, the compositions described herein are free of a second medicament.

In certain embodiments, the at least one surface active agent is selected from the group consisting of nonionic surface active agents, cationic surface active agents, anionic surface active agents, zwitterionic surface active agents, or combinations thereof.

In some embodiments, the compositions include one or more non-ionic surface active agents. Non-ionic surface active agents generally have a hydrophobic group and a reactive hydrogen atom, for example aliphatic alcohols, acids, amides and alkyl phenols, with alkylene oxides, especially ethylene oxide either alone or in combination with propylene oxide. Examples of nonionic surfactant compounds include, but are not limited to, polyoxyethylene glycol sorbitan alkyl esters, block copolymers of polyethylene glycol and polypropylene glycol, ethylene glycol fatty acid esters, poly(ethylene glycol) fatty acid esters, propylene glycol fatty acid esters, polypropylene glycol) fatty acid esters, glycol fatty acid esters, trimethylolpropane fatty acid esters, pentaerythritol fatty acid esters, glucoside derivatives, glycerin alkyl ether fatty acid esters, trimethylolpropane oxyethylene alkyl ethers, fatty acid amides, alkylolamides, alkylamine oxides, lanolin and its derivatives, castor oil derivatives, hardened castor oil derivatives, sterols and its derivatives, polyoxyethylene alkyl ethers, polyoxyethylene alkyl allyl ethers, polyoxyethylene alkylamine, polyoxyethylene fatty acid amides, polyoxyethylene alkylolamides, polyoxyethylene diethanolamine fatty acid esters, polyoxyethylene trimethylolpropane fatty acid esters, polyoxyethylene alkyl ether fatty acid esters, polyoxyethylene polyoxypropylene glycols, polyoxyethylene polyoxypropylene alkyl ethers, polyoxyethylene polyoxypropylene polyhydric alcohol ethers, glycerin fatty acid esters, polyglycerin fatty acid esters, polyoxyethylene glycerin fatty acid esters, sorbitan fatty acid esters, polyoxyethylene sorbitan fatty acid esters, sucrose fatty acid esters, or combinations thereof.

In certain embodiments, the surface active agents comprise polyoxyethylene glycol sorbitan alkyl esters, block copolymers of polyethylene glycol and polypropylene glycol, or combinations thereof.

Examples of polyoxyethylene glycol sorbitan alkyl esters are typically the polysorbates. Polysorbates are a class of oily liquids derived from PEG-ylated sorbitan (a derivative of sorbitol) esterified with fatty acids. Common brand names for polysorbates include Tween®. Tween®-20, Tween®-40, Tween®-60 and Tween®-80, for example, are available from AkzoNobel (Strawinskylaan 2555 1077 ZZ, Amsterdam, the Netherlands). Exemplary polysorbates include polysorbate 20 (polyoxyethylene (20) sorbitan monolaurate), polysorbate 40 (polyoxyethylene (20) sorbitan monopalmitate), polysorbate 60 (polyoxyethylene (20) sorbitan monostearate), and polysorbate 80 (polyoxyethylene (20) sorbitan monooleate).

Examples of block copolymers of polyethylene glycol and polypropylene glycol include the poloxamers. Poloxamers are nonionic triblock copolymers composed of a central hydrophobic chain of polyoxypropylene (poly(propylene oxide)) flanked by two hydrophilic chains of polyoxyethylene (poly(ethylene oxide)). Certain poloxamers, such as those listed herein, are also known by the trade names Pluronic® available from suppliers such as BASF AG (Ludwigshafen, Germany). Because the lengths of the polymer blocks can be customized, many different poloxamers exist that have slightly different properties. Further exemplary Pluronic® poloxamers include, but are not limited to Pluronic® 10R5, Pluronic® 17R2, Pluronic® 17R4, Pluronic® 25R2, Pluronic® 25R4, Pluronic® 31R1, Pluronic® F 108 Cast Solid Surfacta, Pluronic® F 108 NF, Pluronic® F 108 Pastille, Pluronic® F 108 Prill, Pluronic® F 108NF Prill Poloxamer 338, Pluronic® F 127, Pluronic® F 127 Prill, Pluronic® F 127 NF, Pluronic® F 127 NF 500 BHT Prill, Pluronic® F 127 NF Prill Poloxamer 407, Pluronic® F 38, Pluronic® F 38 Pastille, Pluronic® F 68, Pluronic® F 68 Pastille, Pluronic® F 68 LF Pastille, Pluronic® F 68 NF, Pluronic® F 68 NF Prill Poloxamer 188, Pluronic® F 68 Prill, Pluronic® F 68 Prill, Pluronic® F 77, Pluronic® F 77 Micropastille, Pluronic® F 87, Pluronic® F 87 NF, Pluronic® F 87 NF Prill Poloxamer 237, Pluronic® F 87 Prill, Pluronic® F 88, Pluronic® F 88 Pastille, Pluronic® F 88 Prill, Pluronic® F 98, Pluronic® F 88 Prill, Pluronic® F 98, Pluronic® F 98 Prill, Pluronic® L 10, Pluronic® L 101, Pluronic® L 121, Pluronic® L 31, Pluronic® L 35, Pluronic® L 43, Pluronic® L 44, Pluronic® L 61, Pluronic® L 62, Pluronic® L 62 LF, Pluronic® L 62D, Pluronic® L 64, Pluronic® L 81, Pluronic® L 92, Pluronic® L44 NF INH surfactant Poloxamer 124, Pluronic® N 3, Pluronic® P 103, Pluronic® P 104, Pluronic® P 105, Pluronic® P 123 Surfactant, Pluronic® P 65, Pluronic® P 84, Pluronic® P 85, or combinations thereof.

In certain embodiments, the at least one surface active agent comprises a polysorbate present from, for example, 15% (wt/wt) to 35% (wt/wt) of the composition.

In certain embodiments, the polysorbate is present at, for example, 15%, 16%, 17%, 18%, 19%, 20%, 21%, 22%, 23%, 24%, 25%, 26%, 27%, 28%, 29%, 30%, 31%, 32%, 33%, 34%, or 35% (wt/wt) of said composition.

In certain embodiments, the polysorbate is present at, for example, 31% (wt/wt) of the composition.

In certain embodiments, the polysorbate is polysorbate 20, polysorbate 60, polysorbate 80 or a combination thereof. Typically, but not necessarily, the polysorbate is polysorbate 80.

In certain other embodiments, the at least one surface active agent comprises a poloxamer present from, for example, 0.1% (wt/wt) to 5% (wt/wt) of the composition.

In certain embodiments, the poloxamer is present at, for example, 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, or 5% (wt/wt) of said composition.

In certain embodiments, the poloxamer is present at, for example, 0.7% (wt/wt) of the composition.

In certain embodiments, the poloxamer is Pluronic® F87 [$(HO(C_2H_4O)_{64}(C_3H_6O)_{37}(C_2H_4O)_{64}H$], which is poloxamer 237.

In certain embodiments, the compositions described herein comprise a combination of polysorbate 80 and the poloxamer Pluronic® F87 [$(HO(C_2H_4O)_{64}(C_3H_6O)_{37}(C_2H_4O)_{64}H$], which is poloxamer 237.

In certain embodiments, the at least one surface active agent comprises a combination of nonionic surfactants. For example, the combination of nonionic surfactants can comprise a combination of a polysorbate and a poloxamer totaling at least, for example, 30% (wt/wt) of said composition. In certain embodiments, the polysorbate is polysorbate 80 and the poloxamer is poloxamer 237 (Pluronic® F87). In certain embodiments, the polysorbate 80 is present at, about 31% (wt/wt) and the poloxamer 237 is present at, about 0.7% (wt/wt) of said composition.

In some embodiments, the compositions include one or more anionic surface active agents. Exemplary "anionic surface active agents" include, but are not limited to, N-acyl-L-glutamic acid diethanolamine, N-acyl-L-glutamic acid triethanolamine, sodium N-acyl-L-glutamate, sodium alkanesulfonate, ammonium alkyl (C12, C14, C16) sulfate, alkyl (C11, C13, C15) sulfuric acid triethanolamine, alkyl (C11, C13, C15) sulfuric acid triethanolamine, alkyl (C12 to C14) sulfuric acid triethanolamine, liquid alkylsulfuric acid triethanolamine, sodium alkyl (C12, C13) sulfate, liquid sodium alkylsulfate, sodium isoethionate, sodium lacto-isostearate, disodium undecylenoylamido ethyl sulfosuccinate, triethanolamine sulfooleate, sodium sulfooleate, disodium oleamide sulfosuccinate, potassium oleate, sodium oleate, morpholine oleate, oleoyl sarcosine, oleoyl methyltaurine sodium salt, potassium-containing soap base, liquid base for potassium soap, potassium soap, carboxylated polyoxyethylene tridodecyl ether, sodium salt (3 ethyle oxide "E.O.") of carboxylated polyoxyethylene tridodecyl ether, triethanolamine N-hydrogenated tallow fatty-acyl-L-glutamate, sodium N-hydrogenated tallow fatty-acyl-L-glutamate, sodium hydrogenated coconut fatty acid glyceryl sulfate, sodium diundecylenoylamido ethyl sulfosuccinate, sodium stearyl sulfate, potassium stearate, triethanolamine stearate, sodium stearate, sodium N-stearoyl-L-glutamate, disodium stearoyl-L-glutamate, stearoyl methyltaurine sodium salt, sodium dioctyl sulfosuccinate, liquid sodium dioctyl sulfosuccinate, liquid disodium polyoxyethylene monooleylamido sulfosuccinate (2 E.O.), disodium polyoxyethylene lauroyl ethanolamide sulfosuccinate (5 E.O.), disodium lauryl sulfosuccinate, diethanolamide cetyl sulfate, sodium cetyl sulfate, soap base, sodium cetostearyl sulfate, triethanolamine tridecyl sulfate, potassium palmitate, sodium palmitate, palmitoyl methyltaurine sodium salt, liquid castor oil fatty acid sodium salt (30%), ammonium polyoxyethylene alkyl ether sulfate (3 E.O.), liquid diethanolamine polyoxyethylene alkyl (C12, C13) ether sulfate, liquid triethanolamine polyoxyethylene alkyl ether sulfate (3 E.O.), triethanolamine polyoxyethylene alkyl (C11, C13, C15) ether sulfate (1 E.O.), triethanolamine polyoxyethylene alkyl (C12, C13) ether sulfate (3 E.O.), liquid sodium polyoxyethylene alkyl ether sulfate (3 E.O.), sodium polyoxyethylene alkyl (C11, C13, C15) ether sulfate (1 E.O.), sodium polyoxyethylene alkyl (C11 to C15) ether sulfate (3 E.O.), sodium polyoxyethylene alkyl (C12, C13) ether sulfate (3 E.O.), sodium polyoxyethylene alkyl (C12 to C14) ether sulfate (3 E.O.), sodium polyoxyethylene alkyl (C12 to C15) ether sulfate (3 E.O.), disodium polyoxyethylene alkyl (C12 to C14) sulfosuccinate (7 E.O.), sodium polyoxyethylene undecyl ether sulfate, liquid sodium polyoxyethylene octyl phenyl ether sulfate, ammonium polyoxyethylene oleyl ether sulfate, disodium polyoxyethylene lauryl sulfosuccinate, sodium polyoxyethylene nonyl phenyl ether sulfate, sodium polyoxyethylene pentadecyl ether sulfate, triethanolamine polyoxyethylene myristyl ether sulfate, sodium polyoxyethylene myristyl ether sulfate, sodium polyoxyethylene myristyl ether sulfate (3 E.O.), liquid sodium polyoxyethylene lauryl ether acetate (16 E.O.), ammonium polyoxyethylene lauryl ether sulfate (2 E.O.), triethanolamine polyoxyethylene lauryl ether sulfate, sodium polyoxyethylene lauryl ether sulfate, diethanolamine myristyl sulfate, sodium myristyl sulfate, potassium myristyl sulfate, sodium N-myristoyl-L-glutamate, sodium myristoylmethylaminoacetate, liquid myristoyl methyl-alanine sodium salt, myristoyl methyltaurine sodium salt, medicinal soaps, triethanolamine/magnesium coco alkyl sulfate, triethanolamine N-coconut oil fatty-acyl-L-glutamate, sodium N-coconut oil fatty-acyl-L-glutamate, sodium coconut oil fatty acid ethyl ester sulfonate, coconut oil fatty acid potassium salt, liquid coconut oil fatty acid potassium salt, sodium N-coconut oil fatty/hydrogenated fatty-acyl-L-glutamate, coconut oil fatty acid sarcosine, coconut oil fatty acid sarcosine triethanolamine salt, coconut oil fatty acid sarcosine sodium salt, coconut oil fatty acid triethanolamine salt, liquid triethanolamine salt of coconut oil fatty acid, coconut oil fatty acid sodium salt, coconut oil fatty acid methyl alanine sodium salt, liquid coconut oil fatty acid methyl alanine sodium salt, coconut oil fatty acid methyltaurine potassium salt, coconut oil fatty acid methyltaurine sodium salt, sodium laurylamino dipropionate, liquid sodium laurylamino dipropionate (30%), sodium lauryl sulfoacetate; sodium lauryl benzenesulfonate, lauryl sulfate, ammonium lauryl sulate, potassium lauryl sulfate, diethanolamine lauryl sulfate, triethanolamine lauryl sulfate, sodium lauryl sulfate, magnesium lauryl sulfate, monoethanolainine lauryl sulfate, potassium laurate, lauric acid triethanolamine, liquid lauric acid triethanolamine, sodium laurate, lauric acid/myristic acid triethanolamine, lauroyl-L-glutamic acid triethanolamine, sodium N-lauroyl-L-glutamate, lauroyl sarcosine, lauroyl sarcosine potassium, liquid lauroyl sarcosine triethanolamine salt, lauroyl sarcosine sodium, liquid lauroyl methyl-.beta.-alanine sodium salt, lauroyl methyltaurine sodium salt, liquid lauroyl methyltaurine sodium salt, or combinations thereof.

In certain embodiments, said anionic surfactant(s) comprise from, for example, about 0.05% (wt/wt) to about 25% (wt/wt) of said composition. In certain embodiments, said anionic surfactant(s) comprise from, for example, about 0.05% (wt/wt) to about 15% (wt/wt) of said composition. In certain embodiments, said anionic surfactant(s) comprise, for example, 0.05% (wt/wt) to 5% (wt/wt) of said composition. In certain embodiments, said anionic surfactant(s) comprise, for example, 0.5% (wt/wt) to 3% (wt/wt) of said composition. In certain embodiments, said anionic surfactant(s) comprise, for example, 0.7% (wt/wt) of said composition. In certain embodiments, said anionic surfactant(s) comprise sodium lauryl sulfate.

In some embodiments, the compositions include additional surface active agents such as the zwitterionic and cationic surface active agents. Examples of such surface active agents include, but are not limited to the bile acids (e.g., cholic acid, chenodeoxycholic acid, glycocholic acid, glycodeoxycholic acid, taurocholic acid, taurochenodeoxycholic acid, taurolithocholic acid, deoxycholic acid, lithocholic acid, and ursodeoxycholic acid and salts thereof, e.g., sodium, potassium, lithium), natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methyl cellulose), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyllaurate, sodium lauryl sulfate, cetrimonium bromide, cetylpyridinium chloride, benzalkonium chloride, docusate sodium or combinations thereof.

Without being bound to any particular theory, it is believed that the compositions described herein will increase fatty acid absorption in patients with fat malabsorption syndromes and other disease states as described herein. This is because the compositions described herein comprising the omega-3 fatty acid(s) and the at least one surface active agent self-micellize in a manner similar to that in the body. When mammals eat, micelles are naturally formed around the fats ingested. These natural micelles form in the presence of bile regardless of the pH in the stomach or intestines. Natural micelles form around fats and digestive enzymes, entrapping both. Within the micelles, the enzymes quickly cleave the triglycerides or fatty acid esters into free fatty acids and monoglycerides. Natural micelles fuse with the cell membrane when they come in contact with the brush barrier of the intestinal wall, delivering their cargo of free fatty acids and monoglycerides, among other components and compounds, into the cells lining the intestine and are absorbed. Natural micelles that form around omega-3 fatty acids have two characteristics that limit their effectiveness. Firstly, given the formation of natural micelles require the food-dependent release of bile salts, natural micelles form only when food is present. Secondly, since natural micelles require fats from the consumed food in order to form the outer shell of the micelle, the amount of lipids transported into the intestinal wall is directly correlated with the amount of fat co-consumption. As a result, unless a lipophilic compound is co-administered with food, very few natural micelles form and, unless that food contains a sufficient amount of fat, very few natural micelles form. It then follows that the lower the natural micelle formation, the less efficient the natural process is at delivering said lipophilic compound, among other components and compounds, in micellar form, to the intestinal lumen.

In contrast to natural micelles, the formation of artificial micelles has hitherto been very sensitive to the pH of the liquid in which they are being created and to the presence of other substances in that liquid. In addition, artificial micelles are in general either fragile and break easily or are too rigid and never release their cargo, making it difficult for them to deliver adequate amounts of free fatty acids and monoglycerides to the intestinal lining. The micelles formed by the compositions described herein, however, overcome the deficiencies of both artificial and natural human micelles in the delivery of omega-3 fatty acids, while at the same time mimicking some of the characteristics of natural human micelles.

"Emulsion" is a very broad term describing particles that may be amorphous, liquid-crystalline, bilayer, monolayer or any mixture of these structures. An emulsion is a more general term that describes a dispersed phase in a continuous phase that is commonly seen as oil in water (o/w), water in oil (w/o) or even more complex mixtures such as water in oil in water (w/o/w). Emulsion particle sizes can vary widely from 10 nanometers to 100 micrometers.

Solutions in lipid vehicles containing surfactants, which constitute self-emulsifying drug delivery systems (SEDDS), and which effect spontaneous emulsification upon contact of the lipid with fluids in the gastrointestinal tract (GI tract), are known in the art, and are classified as "self-emulsified", "self-micro", and "self-nano", drug delivery systems (herein referred to as "SEDDS," "SMEDDS," and "SNEDDS," respectively). The SEDDS, SMEDDS, and SNEDDS are emulsions. These emulsions have the sole purpose of dispersing lipids, such as oils, into small droplets in order to increase the surface area available to interact with the body's natural bile salts, pancreatic lipases, co-lipase, and phospholipase A2.

SEDDS are formulated with mixtures of lipid vehicles, non-ionic surfactants and a drug in the absence of water, and are assumed to exist as transparent isotropic solutions. These systems have a unique property—they are able to self-emulsify rapidly in the gastrointestinal fluids, forming fine oil-in-water emulsions (droplet size diameter <300 nm) under gentle agitation provided by gastrointestinal motion. SEDDS are commonly suitable for oral delivery in soft and hard gelatin or hard hydroxypropyl methylcellulose (HPMC) capsules.

SMEDDS are defined as isotropic mixtures of an oil, surfactant, co-surfactant (or solubilizer) and a drug. Such systems form fine oil-in-water microemulsions under gentle agitation provided by digestive motility of the stomach and intestine following dilution by the aqueous phase in vivo. SMEDDS are distinguished from SEDDS by smaller emulsion droplets produced on dilution, resulting in a transparent or translucent stable dispersion. Mean droplet size after dilution is <100 nm in the case of SMEDDS or <300 nm in the case of SEDDS. SMEDDS generally contain relatively high concentrations of surfactant (typically 30 to 60%, m/m), and optionally also hydrophilic co-solvents (e.g., propylene glycol, polyethylene glycols). They are often described as microemulsion pre-concentrates because the microemulsion is formed on dilution in aqueous media.

SNEDDS are defined as self-nanoemulsifying drug delivery systems that spontaneously form transparent to opalescent oil-in-water dispersions of approximately 200 nm in size upon dilution with water under gentle stirring.

As these various emulsions move through the GI tract various processes occur. First the components are dispersed to form lipid droplets, or emulsion droplets. This is followed by lipolysis and solubilization of the digestion products by bile acids, which may then form colloidal mixed micelles. It is believed that the drug then partitions from the emulsion oil droplets and bile salt mixed micelles to be absorbed by the mucosal cells of the intestinal wall.

Thus, because SEDDS, SMEDDS, and SNEDDS leverage the body's natural process to be efficient, they also necessarily rely on the natural processes to be effective. This is particularly important because in order to form micelles, SEDDS, SMEDDS, and SNEDDS require the presence of bile salts. Since bile salts are emitted into the GI tract in mammals as a response to food consumption, then it follows that SEDDS SMEDDS, and SNEDDS are not able to use bile salts to form micelles in the GI tract unless food intake has induced the introduction of bile salts into the GI tract.

On the contrary, the present invention is directed toward a Self-Micellizing Drug Delivery System (SMDDS). This system is differentiated from the SEDDS, SMEDDS and SNEDDS as described above, in that the particularly described combination of surface active agent (polysorbate and poloxamer 237) in the relative amounts and overall concentrations as herein described, are unique in their ability to directly and spontaneously form stable micelles in a size range of about 1 to about 10 micron without relying on the presence of bile salts. This represents a distinct and unique advantage of the present invention, in that, unlike SEDDS, SMEDDS, and SNEDDS, the present invention is able to deliver lipids through the intestinal wall by way of a plurality of spontaneously formed stable micelles. Unlike SEDDS, SMEDDS, and SNEDDS, which function to disperse lipids to increase surface area, the present invention encapsulates the lipids with surface active agents, thus bringing the lipids together, whereby predictable and repeatable enhancements in bioavailability are realized, absent any food effect.

As opposed to an emulsion, a micelle is a particle of colloidal dimensions that exists in equilibrium with molecules or ions in a solution from which it is formed. Micelles are a particular type of particle (oil particle in water) which form a structure wherein the hydrophilic component is external and the hydrophobic component is internal. More specifically, micelles are usually formed from single chain lipids and surfactants, and a micelle is always a monolayer particle with the hydrophilic head facing the aqueous phase and the hydrophobic tail facing the oil phase.

One method of determining a human's normal weight range is to assess the subject's Basal Metabolic Rate (BMR), which takes into account a subject's height, weight, age and gender. BMR determinations are well known in the art. Accordingly, it is believed, without being bound to any particular theory, that the compositions or a plurality of micelles pre-formed therefrom described herein will lower a human's weight, if the human is overweight, to within the normal range as determined by the human's BMR. Conversely, it is believed, without being bound to any particular theory, that the compositions or a plurality of micelles pre-formed therefrom described herein will increase a human's weight, if the human is underweight, malnourished, or is suffering from a malabsorption syndrome, to within the normal range as determined by the human's BMR.

It is known in the art that food intake in a subject having a normal weight stimulates adipose tissue to increase leptin levels. Leptin is a hormone that tells the brain it is full and increases metabolism. Thus, in starvation mode there is a decrease in leptin, telling the brain it is hungry, which in turn stimulates food intake and decreases energy expenditure. In an obese subject, however, the brain is resistant to leptin signaling despite leptin levels being high, thus, the subject believes it is not satiated and continues eating and gaining weight.

Omega-3 fatty acids are known to decrease circulating leptin levels. Accordingly, without being bound to any particular theory, it is believed that the enhanced absorption of omega-3 fatty acids provided by the compositions or a plurality of micelles pre-formed therefrom described herein will regulate leptin levels and signal a subject's brain accordingly to either decrease leptin levels if the subject is overweight or increase leptin levels if the subject is underweight, malnourished, or is suffering from a malabsorption syndrome. This increase or decrease in metabolism, as the case may be, is reflected by an increase or decrease in circulating free fatty acids when compared to circulating free fatty acid levels at the start of the dosing regimen.

Without being bound to any particular theory, it is believed that the self-micellizing compositions described herein will regulate metabolism in a subject administered said compositions to facilitate returning the subject's weight to within a normal range for that particular subject.

Accordingly, in at least one embodiment of the present invention, a method is disclosed for administering self-micellizing compositions described herein to facilitate a subject's weight gain, loss, or return to normal weight, or combinations thereof over time.

In at least one embodiment of the present invention, a composition is disclosed which can be used to increase the weight of a mammal, such as livestock.

Also disclosed herein in at least one embodiment of the invention is a method for administering a composition as provided herein to increase the weight of a mammal, such as livestock.

In at least one embodiment, the compositions described herein comprising the omega-3 fatty acid(s) and the at least one surface active agent, for example the combination of polysorbate 80 and poloxamer 237, spontaneously form micelles when encountering aqueous liquids. These micelles form regardless of the pH or the nature and concentration of other suspended materials in the liquid, do not require bile to form, and form micelles that remain stable almost indefinitely. The micelles form whether or not food is present or whether food that is present is high or low in fat. Like human micelles, the micelles formed by the compositions described herein form around omega-3 fatty acids and entrap both fats and enzymes, allowing rapid digestion and the formation of free fatty acids and monoglycerides. Without being held to any one theory, it is believed that the micelles formed by the compositions described herein are similar in size to human micelles and share the ability to rupture at the intestinal brush barrier. Without being held to any one theory, it is believed that either by friction or a chemical reaction, the micelle ruptures and spills its contents onto the lining of the intestines and the intestines absorb the omega-3 fatty acids.

Accordingly, it is believed that compositions described herein can overcome one of the primary challenges of malabsorption syndromes, such as SBS i.e., the delivery of adequate amount of free fatty acids to the bloodstream of patients suffering from the hepatic complications of SBS without exacerbating liver dysfunction, as does TPN treatment, or triggering fat malabsorption or dumping. This would also allow for more consistent dosing and thus produce more reliable results.

In certain embodiments, the compositions described herein self-micellize in an aqueous medium. The aqueous medium can include, for example, 0.1N HCl. It is well accepted that 0.1N HCl (simulated gastric fluid) serves as a proxy for the acidity of stomach contents. Accordingly, and without being bound by theory, it is believed that the compositions described herein can self-micellize in situ in the stomach or small intestine. In certain embodiments, the compositions described herein more efficiently and effectively deliver omega-3 fatty acid esters through the intestinal tract when administered with or without food.

In addition to forming micelles in situ, in other embodiments, compositions comprising micelles are provided, wherein the micelles are formed by the addition of an aqueous medium to a composition of any one of the embodiments provided herein prior to administration of said composition to a subject in need of treatment. Alternatively, micelles can also be formed when the compositions are added to an aqueous medium. In certain embodiments, the micelles have a diameter of up to 10 µm. In other embodiments, substantially all of the micelles have an average diameter of from 1 µm to 10 µm. In certain embodiments, the micelles have an average diameter of, for example, 1, 2, 3, 4, 5, 6, 7, 8, 9 or 10 µm. In certain embodiments, said micelles are stable at ambient temperature and in certain other embodiments, said micelles are stable at about normal mammalian body temperatures.

The surface active agents comprising the compositions suitable for self-micellization as described herein generally have an HLB from, for example, 12 to 18. In certain embodiments, said surface active agents have an HLB from, for example, 12.0 to 14.0. In certain embodiments, said surface active agents have an HLB from, for example, 13.0 to 14.0. In certain embodiments, said surface active agents have an HLB from, for example, 13.5 to 13.8. The total HLB of all the surface active agents or surfactants used in the composition is generally from, for example, 12 to 18. In some embodiments, the total HLB of all surface active agents used in the composition is generally from, for example, 12 to 15. In some embodiments, the total HLB of all surface active agents or surfactants used in the composition is generally from, for example, 13 to 15.

In certain embodiments, the at least one surface active agent or surfactant has an HLB of at least, for example, 8.0. In some embodiments, said surface active agent(s) or surfactant(s) have a combined HLB in the range of from, for example, 13 to 15. As the HLB value of the surface active agent(s) or surfactant(s) increases, the amount of surface active agent or surfactant needs to be decreased.

The compositions described herein can further comprise at least one antioxidant. The antioxidant(s) suitable for use in the instant omega-3 fatty acid compositions, include, but are not limited to tocopherols and/or tocotrienols and can be present from, for example, 0.01% to 5% (wt/wt) of the composition. In certain such embodiments, the tocopherols and/or tocotrienols can be present at, for example, 0.01%, 0.05%, 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5% or 5% by weight of the compositions. In certain such embodiments, the antioxidant is α-tocopherol present at, for example, 2% by weight of the composition.

In certain embodiments, the composition further comprises a terpene. In certain embodiments, the terpene is d-limonene. In one embodiment, the terpene is a cyclic terpene. In one embodiment, the terpene is d-limonene ((+)-limonene), which is the (R)-enantiomer. In one embodiment, the terpene is L-limonene, which is the (S)-enantiomer. In one embodiment, the terpene is racemic limonene, known as dipentene. In another embodiment, the terpene is a terpenoid. In another embodiment, the terpene or terpenes are derived from a natural oil (e.g., a citrus oil such as orange oil). Other terpenes are contemplated, such as monoterpenes (e.g., terpinenes, terpinolenes, phellandrenes, or menthol), having structures that are similar to d-limonene. In certain embodiments, the compositions further comprise substantially pure d-limonene from, for example, 0.1% to 5% by weight of the composition. In certain other embodiments, the compositions further comprise natural orange oil from, for example, 0.1% to 5% by weight of the composition. Compositions comprising d-limonene or orange oil can aid in the elimination and/or minimization of side effects from the oral administration of the instant omega-3 fatty acid compositions. Such side effects include regurgitation, frequency of belching, gastroesophageal reflux disease (GERD), bloating, increased intestinal gas, fish taste, fishy breath, fish smell, nausea, diarrhea, or combinations thereof.

Methods for Treating Age-Related Macular Degeneration

Methods are provided of treating AMD in a subject in need of treatment, which method comprises administering to said subject a therapeutically effective amount of a composition of any one of the embodiments provided herein, or a pre-formed micelles according to the respective embodiments described herein. The compositions described herein can be administered in conjunction with other medications and/or nutritional supplements prescribed for treating AMD. In certain embodiments, non-limiting examples of non-omega-3 fatty acid nutritional supplements include, for example, a combination of vitamin C, vitamin E, beta-carotene, zinc, copper, magnesium, manganese, calcium, vitamin A, vitamin D, vitamin K2, lutein and zeaxanthin. Non-limiting examples of non-omega-3 fatty acid active agents include, for example, verteporfin (VISUDYNE); the antioxidant carotenoids crocin and crocetin, as found in, for example, Saffron (*Crocus sativus*) and inhibitors of angiogenesis, such as for example, BEVACIZUMAB (AVASTIN®), RANIBIZUMAB (LUCENTIS®), PEGAPTANIB (MACUGEN®) AND AFLIBERCEPT (EYLEA®).

The compositions described herein can also be administered for treating Juvenile Macular Degeneration, which includes Stargardt's disease, Best disease, and juvenile retinoschisis by administering the compositions described herein to a human juvenile.

In certain embodiments, the amount of the non-omega-3 fatty acid active agents administered in conjunction with the compositions described herein can be reduced to avoid or minimize any side effects resulting from the non-omega-3 fatty acid active agents when such agents are administered alone at higher concentrations.

In at least one embodiment, a method is provided for treating AMD by administering, to a patient in need thereof, a therapeutically effective amount of a composition comprising omega-3 DPA fatty acid (either in the triglyceride, ester or free fatty acid ester form) and at least one surface active agent in an amount and a combination effective to cause said compositions to spontaneously self-micellize when in contact with an aqueous medium, thereby forming a plurality of stable micelles having a particle size within a range of about 1 μm to about 10 μm.

Methods for Treating Fat Malabsorption Syndromes or Disorders

Methods are provided for treating one or more fat malabsorption syndrome or disorder in a subject in need of treatment, which method comprises administering to said subject a therapeutically effective amount of a composition of any one of the embodiments provided herein, or a pre-formed micelle mixture of any one of the embodiments provided herein.

Accordingly, in certain embodiments, the fat malabsorption syndrome can be the result of a disorder in the intestinal processes of digestion and/or transport of nutrients across the intestinal mucosa into the systemic circulation. The fat malabsorption syndrome can be either a congenital abnormality in the digestive or absorptive processes or a secondarily acquired disorder resulting from a disorder of the intestinal processes of digestion and/or transport of nutrients across the intestinal mucosa into the systemic circulation.

Exocrine pancreatic insufficiency can also result in a fat malabsorption syndrome or disorder. Exocrine pancreatic insufficiency can be the result of pancreatitis, pancreatic cancer, pancreatic resection, cystic fibrosis, Shwachman-Diamond syndrome, Johnson-Blizzard syndrome, and Pearson syndrome. Accordingly, in certain embodiments, the compositions described herein can be used for the treatment of fat malabsorption syndrome resulting from exocrine pancreatic insufficiency.

Obstructive biliary or cholestatic liver disease or extensive intestinal mucosal disease, such as that which occurs in celiac disease can result in fat malabsorption syndromes. Thus, in certain embodiments, the compositions described herein can be administered to a human in need of such administration for the treatment of fat malabsorption resulting from obstructive biliary or cholestatic liver disease or extensive intestinal mucosal disease.

Fat malabsorption syndromes can be the result of functional or anatomic loss of extensive segments of small intestine leading to a severe decrease in intestinal absorptive capacity, often referred to as Short-Bowel Syndrome (SBS), which may be congenital or acquired as a result of surgery due to Crohn's Disease or necrotizing enterocolitis in infants or neonates. In certain embodiments, the administration of the compositions described herein to a human, particularly a neonate, in need of such administration, can treat fat malabsorption syndromes resulting from SBS or Crohn's Disease.

In order to increase the absorption of dietary fats, including docosahexaenoic acid, through enteral administration, a combination of fatty acids and surface active agents, specifically poloxamers and polysorbates, can be combined to form self-micellizing micelles. Attempts to create artificial micelles have generally resulted in artificial micelles that are fragile and break easily, making it difficult for the particles to deliver adequate amounts of free fatty acids and monoglycerides to the intestinal lining for absorption. For this reason, creating micelles mimicking necessary characteristics of natural human micelles is important, especially having a size of about five microns in diameter to carry its cargo of dietary fats (or other lipophilic materials) to and through the intestinal cell wall is a novel means of creating bioavailable dietary fats for the treatment of malabsorption.

In one exemplary embodiment of the present invention, a novel formulation was utilized containing docosahexaenoic acid in combination with a blend of surface active agents including polysorbates and poloxamers, and a study was carried out in a porcine model of SBS. The methodology and results of this experiment are set forth in Example 3.

It was concluded that enteral administration of a novel DHA preparation that forms micelles independent of bile salts results in increased fatty acid absorption, weight gain and improved intestinal morphologic adaptation in a neonatal porcine model of SBS.

In certain embodiments, administration of the compositions described herein can be administered in conjunction with a non-omega-3 fatty acid active agent for the treatment of SBS. Non-limiting examples of such non-omega-3 fatty acid active agents can include L-GLUTAMINE (NUTRESTORE®), RECOMBINANT SOMATOTROPIN (ZORBTIVE®), AND TEDUGLUTIDE (GATTEX®). Other such non-omega-3 fatty acid active agents may include conjugated bile acids or opium tincture. In certain embodiments, the amount of the non-omega-3 fatty acid active agent(s) administered in conjunction with the compositions described herein can be reduced to avoid or minimize any side effects resulting from the non-omega-3 fatty acid active agents when such agents are administered alone at higher concentrations.

Methods for Treating NAFLD and/or NASH

Methods are provided of treating NAFLD and/or NASH in a subject in need of treatment, which method comprises administering to said subject a therapeutically effective amount of a composition of any one of the embodiments provided herein, or pre-formed micelles according to the respective embodiments described herein.

The compositions described herein can be administered concomitantly with other non-omega-3 fatty acid medications prescribed for treating NAFLD and/or NASH. Non-limiting examples of such non-omega-3 fatty medications can include, lipid lowering or cholesterol lowering agents selected from the group consisting of cholesterol absorption inhibitors, bile acid sequestrants/resins, statins, niacin and derivatives, MTP inhibitors, fibrates and CETP inhibitors, insulin sensitizers, hypolipidemics, anti-inflammatory medications, and thiazolidinediones. In certain embodiments, the amount of the non-omega-3 fatty acid active agent(s) administered in conjunction with the compositions described herein can be reduced to avoid or minimize any side effects resulting from the non-omega-3 fatty acid active agents when such agents are administered alone at higher concentrations.

In certain embodiments, the compositions, or a plurality of micelles pre-formed therefrom, described herein, provide for a method of treating a Non-Alcoholic Fatty acid Liver Disease (NAFLD) comprising the step of administering to a subject in need of such administration the compositions or a plurality of micelles pre-formed therefrom described herein.

In certain embodiments, the compositions, or a plurality of micelles pre-formed therefrom, described herein, provide for a method of treating Non-Alcoholic Steatohepatitis (NASH) comprising the step of administering to a subject in need of such administration the compositions or a plurality of micelles pre-formed therefrom described herein.

In certain embodiments, the compositions, or a plurality of micelles pre-formed therefrom, described herein, provide for a reduction in body weight (or weight loss) in a subject diagnosed with NAFLD and/or NASH.

In certain embodiments, the compositions, or a plurality of micelles pre-formed therefrom, described herein, provide for a method of reducing liver weight in a subject diagnosed with NASH.

In certain embodiments, the compositions, or a plurality of micelles pre-formed therefrom, described herein, provide for a method of reducing whole blood glucose in a subject diagnosed with NASH.

In certain embodiments, the compositions, or a plurality of micelles pre-formed therefrom, described herein, provide for a method of reducing liver triglyceride levels in a subject diagnosed with NAFLD and/or NASH.

In certain embodiments, the compositions, or a plurality of micelles pre-formed therefrom, described herein, provide for a method of reducing development of liver fibrosis in a subject diagnosed with NAFLD and/or NASH.

A nine-week preclinical study of certain embodiments of the present invention was conducted using a mouse model which progresses from NAFLD to NASH between 5 to 9 weeks of age. Within the disease progression of this animal model, the liver triglycerides reach a point around week 6 where the inflammation has progressed substantially over week 5. The study contained three groups, a control group given a placebo from age five to nine weeks, and two trial groups, a first trial group administered a composition disclosed herein for 4 weeks, from five to nine weeks of age, and a second trial group administered the same said composition disclosed herein for 3 weeks, from six to nine weeks of age.

Figure 3:
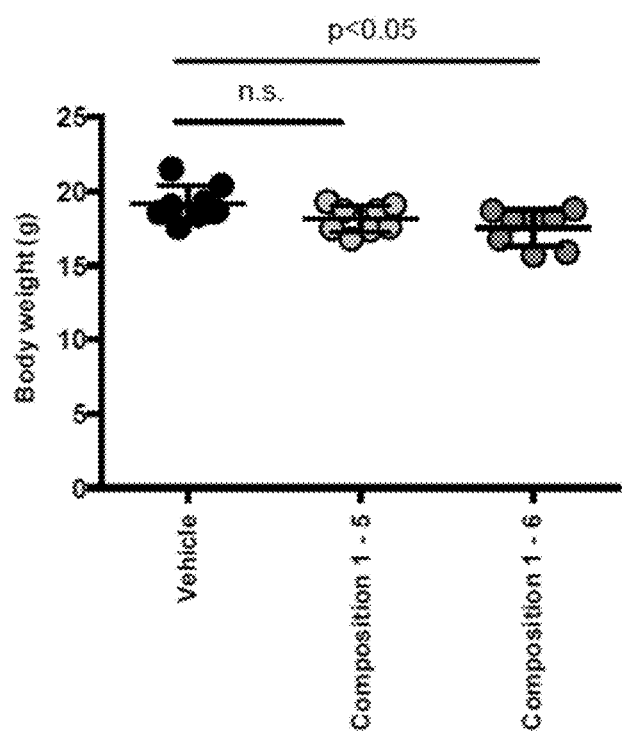
FIG. 3 shows the mean body weight on the day of sacrifice of the mice between each of the Control, Second Treatment Group and Third Treatment Group.

The study showed that animals for which treatment was started later, the 3 week treatment group, had significantly reduced liver triglyceride contents compared with the control group. Although the liver triglycerides tended to decrease in both treatment groups, the 4 week treated group (from five to nine weeks) showed a non-significant change (at 0.05) and the group treated for 3 weeks (from six to nine weeks) showed a statistically significant decrease, as illustrated in FIG. 3. This 3 week treatment group also showed a tendency for reduced whole blood glucose levels compared with the control group. The significant decrease in the liver triglycerides in the more progressed group demonstrate that certain embodiments of the present invention can improve lipid and glucose metabolism in the liver. These results also demonstrate that omega-3 fatty acids can improve lipid and glucose metabolism in the liver.

The effect of the treatment was not merely through an induction of weight loss by the animals. In fact, the study found that body weight gradually increased during the treatment period in all groups and that there was no difference in mean body weight between groups. Although the end liver weight of the subjects in the treatment groups was lower than that of the subjects in the control group, the difference was not statistically significant. In addition, both treatment groups trended to reduce alpha-SMA (a marker of myofibroblast associated with the development of liver fibrosis) mRNA expressions in the liver, a key indicator of the treatment's demonstrated ability to delay the progression to NASH. Without being held to any one theory, we believe the study demonstrates the ability of at least one composition disclosed herein to deliver polyunsaturated EPA and DHA fatty acids to mammals with NAFLD for incorporation into the cell membrane of erythrocytes, wherein said delivery can reduce the triglyceride level in the liver and thereby slow the disease's progression to NASH. The study may also indicate that administration of compositions disclosed herein might provide a larger medicinal response when provided later in the disease progression from NAFLD to NASH.

Methods for Treating Neurodegenerative Diseases

Methods are provided of treating neurodegenerative disease in a subject in need of treatment, which method comprises administering to said subject a therapeutically effective amount of a composition of any one of the embodiments provided herein, or pre-formed micelles according to the respective embodiments described herein. Non-limiting examples of neurodegenerative diseases that can be treated by the compositions described herein include PD, AD, MS, Epilepsy, and ALS.

The compositions described herein can be administered concomitantly with other non-omega-3 fatty acid medications prescribed for treating neurodegenerative diseases. Non-limiting examples of medications can include medications generally approved by a health regulatory body and prescribed by physicians for a particular neurodegenerative disease. In certain embodiments, the amount of the non-omega-3 fatty acid active agent(s) administered in conjunction with the compositions described herein can be reduced to avoid or minimize any side effects resulting from the non-omega-3 fatty acid active agents when such agents are administered alone at higher concentrations.

Methods for Treating Primary Sclerosing Cholangitis

Methods are provided of treating PSC and or NSC in a subject in need of treatment, which method comprises administering to said subject, typically a human adult, infant, child or adolescent, a therapeutically effective amount of a composition of any one of the embodiments provided herein, or pre-formed micelles according to the respective embodiments described herein.

PSC, which is a chronic cholestatic liver disease, can result in fat malabsorption syndromes. Thus, in certain embodiments, the compositions described herein can be administered to a human in need of such administration for the treatment of fat malabsorption resulting from PSC.

In certain embodiments, the compositions described herein can be administered in conjunction with non-omega-3 fatty acid active agents. Examples of such active agents can, upon approval by a respective regulatory agency, include 6-alpha-ethylchenodeoxycholic and/or (4R,5R)-1-[[4-[[4-[3,3-Dibutyl-7-(dimethylamino)-2,3,4,5-tetrahydro-4-hydroxy-1,1-dioxido-1-benzothiepin-5-yl]phenoxy]methyl]phenyl]methyl]-4-aza-1-azoniabicyclo[2.2.2]octane chloride.

In certain embodiments, the amount of the non-omega-3 fatty acid active agents administered in conjunction with the compositions described herein can be reduced to avoid or minimize any side effects resulting from the non-omega-3 fatty acid active agents when such agents are administered alone at higher concentrations.

Methods for Treating Sickle Cell Disease

Methods are provided of treating sickle cell disease in a subject in need of treatment, which method comprises administering to said subject a therapeutically effective amount of a composition of any one of the embodiments provided herein, or pre-formed micelles according to the respective embodiments described herein.

The compositions described herein can be administered concomitantly with other non-omega-3 fatty acid active agents and non-omega-3 nutritional supplements prescribed for treating sickle cell disease. Non-limiting examples of non-omega-3 active agents can include pain medications, antibiotics, hydroxyurea, anti-inflammatory medications, and aspirin, particularly a low-dose (70-81 mg) aspirin dosage form; while non-omega-3 nutritional supplements may include one or more of folic acid, magnesium, manganese, zinc, calcium, vitamin A, vitamin E, vitamin D, and vitamin K2. In certain embodiments, the amount of the non-omega-3 fatty acid active agent(s) administered in conjunction with the compositions described herein can be reduced to avoid or minimize any side effects resulting from the non-omega-3 fatty acid active agents when such agents are administered alone at higher concentrations.

While not wishing to be bound to any particular theories, it is believed that compositions comprising omega-3 DPA fatty acid (either in the triglyceride, ester or free fatty acid ester form) and at least one surface active agent in an amount and a combination effective to cause said compositions to self-micellize when in contact with an aqueous medium can be used to treat sickle cell disease symptoms, such as vaso-occlusive events, sequestration crisis, avascular necrosis, stroke, and sickle cell anemia, among other known maladies, by decreasing the aggregation of platelets, red blood cells, and/or white blood cells.

Nutritional Factors Associated with SCD Pathophysiological and Clinical Outcomes (A) Long Chain Polyunsaturated Fatty Acids (LCPUFA)

Until recently, cell membrane lipids (fatty acids) were regarded as biologically inert compounds that provide a permeability barrier between interior and exterior compartments within and between cells. It is now recognized that lipids, independently and in concert with proteins, are central to the regulation of cell and sub-cellular functions including signaling and gene expression. A third of all proteins are in membranes. These proteins, which are responsible for signaling, transport and oxidative protection and other vital cellular processes, are dependent on membrane lipids for their optimal function. Experimental and human studies demonstrate that abnormal composition, perturbation or deviation from normality of lipids leads to cell dysfunction.

Studies have shown that variation in dietary composition of saturated and monosaturated fatty acids cause very little change in percent saturation of membrane lipids. In contrast, membrane lipids are very responsive to variation to dietary composition of LCPUFA. The greatest sensitivity to changes in dietary fatty acids was for n-3 PUFA and n-6/n-3 fatty acids ratio. A 300% increase in red blood DHA and EPA composition has been observed in subjects supplemented with 1296 mg EPA and 864 mg DHA. Similarly, a 10 fold increase in EPA concentration of mononuclear cell membrane phospholipids has been observed four weeks after supplementation. Studies using multiple doses of fish oil show that the incorporation of these fatty acids in immune cells occurs in a manner that is highly correlated with the amount of the fatty acid consumed. Typically the increase in content of n-3 PUFAs occurs at the expense of n-6 PUFAs, especially arachidonic acid.

Unlike n-6 fatty acids, n-3 fatty acids do not occur in large amounts in plants food and western human diet. Moreover, the alpha-linolenic acid (ALA) conversion process to EPA and DHA in humans is not efficient as only 5-10% are converted to EPA, and a mere 2-5% to DHA. N-3 fatty acids are abundantly present in fish and shellfish. In fact, fish-oil supplements typically contain 30-50% of n-3 FAs. The current adequate intake (AI) for ALA issued by the Institute of Medicine of the National Academies, USA is 1.6 g/day for men 19-47 years and 1.1 g/day for women 19-47 years. The acceptable macronutrient distribution range (AMDR) for ALA is 0.6-1.2% of energy. The lower boundary of the range meets the AI for ALA. Approximately 10% of the AMDR for ALA can be consumed as EPA and/or DHA. The dietary guidelines (2005) also note that consumption of approximately two servings of fish per week (approximately 224 g total) may reduce the risk of mortality from coronary heart disease. However, since the physiological potency of EPA and DHA is greater than ALA and there has been a substantive increase in the evidence base about the health benefits of long chain omega-3 fatty acids.

Perturbation of cell membrane fatty acids composition has been observed on red blood cells, platelets and mononuclear cells of patients with SCD. The abnormality is characterized by high omega-6, low omega-3 and an imbalance between the two fatty acid families. The n-3 and n-6 LCPUFA are vital structural and functional components of cell and sub-cellular components. Studies have shown that the balance between these two fatty acid families influences blood cell adhesion, aggregation, blood coagulation, cell deformability and inflammatory response. Hence, it has been postulated that an imbalance in membrane n-6/n-3 LCPUFA is the antecedent of the loss of membrane asymmetry, blood cell adhesion and aggregation and vaso-occlusion in SCD. Interestingly, experimental and clinical studies have shown that supplementing SCD patients with omega-3 fatty acids corrects cell membranes abnormalities and confer protection against vaso-occlusive pain episodes, severe anaemia and oxidative stress, and improves red blood cells flexibility in mice, modulates the eicosanoids and resolvin production, expression of adhesive molecules, and the overall inflammatory state. The retroconversion of DHA to satisfy the omega-3 deficiencies at this cellular level results in a normalization of the cell membrane and alleviation of symptoms of the disease state. The displacement of ARA during this process decreases systemic inflammation.

(B) Antioxidants

Patients with sickle cell disease are under oxidative overload caused by accelerated auto-oxidation and iron de-compartmentalization. Among the factors thought to participate in systemic high oxidative stress (OS) associated with SCD is the increased intravascular haemolysis and excessive levels of cell-free haemoglobin with its catalytic action on oxidative reaction. In addition, a chronic pro-inflammatory state is a characteristic of SCD patients even in steady state, and reactive oxygen species (ROS) production is a main feature of and plays an important role in inflammation. It has also been demonstrated that hypoxia-reoxygenation cycles in SCD are associated with increased OS and severe reperfusion injury. On the other hand, it has been found that the anti-oxidant capacity in RBCs of SCD patients is highly impaired. Thus, the chronic OS state associated with SCD is an outcome of imbalance between enhanced generation of reactive oxygen species (ROS) and disrupted antioxidant system. It has been postulated that the impaired antioxidant capacities could be due to an accelerated utilization of antioxidant nutrients. There is evidence to indicate that patients with SCD have a reduced levels of vitamin A, C, E and beta carotene and zinc.

(C) Protein

Sickle cell disease is associated with hyper-metabolism and a consequent shortage of substrates for normal growth and healthy immune response. Insufficient nutrition in general is associated with poor immune function and is consequently regarded as the most common cause of immunodeficiency worldwide. The protein: energy ratio is a major determinant of dietary adequacy.

Experimental studies have demonstrated that high protein intake results in lower circulating inflammatory markers, fewer infarcts in spleen, liver, and kidney, and lower histopathologic scores for chronic tissue injury in liver and spleen. In addition, high-protein fed sickle mice had less vascular leakage in the heart, lungs, and brain and a better acute immune response and survival rate than matched normal-protein sickle mice. These experimental studies suggest that that the difference in nutritional intake might be a major contributory factor that explains partially the wide spectrum of SCD clinical manifestation and severity. However, to the best of our knowledge, no study has investigated the long-term effect of low or high protein and energy intake on SCD acute and chronic complications.

Based on the previous studies on nutritional modifiers of sickle cell disease and the FDA approved Daily Reference Values (DRVs) and Reference Daily Intakes (RDIs) for adults and children four or more years of age, the following dietary formula to prevent acute and chronic complications associated with SCD:
Protein: 50 g
Vitamin A: 5,000 International Units (IU)
Vitamin C: 60 mg
Vitamin E: 30 IU
Beta carotene:
Folate: 400 µg
Zinc: 15 mg
Manganese: 2 mg
Copper: 2 mg
Selenium: 70 µg
Omega-3 fatty acids (DHA AND EPA): 500 mg Kits Packaged pharmaceutical kits comprising the compositions described herein are contemplated. The kits comprise the compositions described herein as unit dosage forms in a container made of an inert material, such as for example, a glass vial, which can be clear or colored. The glass vial can be a crimp or snap top glass vial. Included in the kits are instructions for using the dosage form to treat a subject having a disease or disorder responsive to treatment by administration of the dosage forms comprising the compositions described herein.

The packaged pharmaceutical kits provide prescribing information, over the counter medical use information, and/or nutritional information for the dosage form including, for example and without limitation, to a subject or health care provider, or as a label in a packaged pharmaceutical kit. Information included in the kit may include, for example and without limitation, efficacy, dosage and administration, contraindication and adverse reaction information pertaining to the omega-3 fatty acid compositions described herein. The dosage and administration information, for example, can include dosing frequency recommendations as well as administration of the compositions with or without food.

In certain embodiments the dosage forms comprising the compositions provided herein are in the form of a liquid filled or gel filled capsules for oral administration, which are provided either as blister packages or in bottles together with over the counter or prescription medical use information and/or nutritional information.

The packaged pharmaceutical kits can comprise one or more of the omega-3 fatty acids comprising the compositions described herein as the only active ingredient. In other embodiments, one or more of the compositions described herein can be packaged in combination with one or more active agents other than a non-Omega 3 fatty acid, such as for example and without limitation, one or more other lipid lowering or cholesterol lowering agents selected from the group consisting of cholesterol absorption inhibitors, bile acid sequestrants/resins, statins, niacin and derivatives, MTP inhibitors, fibrates and CETP inhibitors, 6-alpha-ethylchenodeoxycholic and/or (4R,5R)-1-[[4-[[4-[3,3-Dibutyl-7-(dimethylamino)-2,3,4,5-tetrahydro-4-hydroxy-1,1-dioxido-1-benzothiepin-5-yl]phenoxy]methyl]phenyl]methyl]-4-aza-1-azoniabicyclo[2.2.2]octane chloride, insulin sensitizers, hypolipidemics, anti-inflammatory medications, and thiazolidinediones, pain medications, antibiotics, folic acid, hydroxyurea, and anti-inflammatory medications.

In certain embodiments such active agents can include medications generally approved by a health regulatory body and prescribed by physicians for a particular neurodegenerative disease.

In other embodiments, one or more of the compositions described herein can be packaged in combination with one or more nutritional supplements. Non-limiting examples of supplements include various minerals, such as calcium, magnesium, iron, and vitamins, particularly fat-soluble vitamins, as well protein supplements well known in the art.

Dosage Forms

Any of the omega fatty acid containing compositions provided herein can be provided as a pharmaceutical composition to be administered orally or parenterally, as a nutraceutical formulation, or a dietary supplement.

In certain embodiments of the invention, compositions comprise at least one surface active agent, at least one fat-soluble vitamin, such as vitamin A, vitamin D, vitamin K, vitamin K2, among others, and an omega-3 fatty acid (in triglyceride, ester, or free fatty acid form). In certain embodiments of the invention, at least one surface active agent is combined with at least one fat-soluble vitamin and an omega-3 fatty acid (in triglyceride, ester, or free fatty acid form) in relative concentrations sufficient to form micelles when added to an aqueous medium. In certain other embodiments of the invention, at least one surface active agent is combined with at least one fat-soluble vitamin, an omega-3 fatty acid (in triglyceride, ester, or free fatty acid form), and one or more minerals, such as magnesium, manganese, zinc, copper, selenium, and combinations thereof.

In certain embodiments of the invention, at least one surface active agent is combined with at least one fat-soluble vitamin, an omega-3 fatty acid (in triglyceride, ester, or free fatty acid form), and one or more minerals, such as magnesium, manganese, zinc, copper, selenium, and combinations thereof, such that when added to an aqueous medium, the composition forms micelles and wherein said micelles range in size from 1 um to 10 um in diameter.

The pharmaceutical compositions described herein may further include one or more pharmaceutically acceptable excipients. Pharmaceutically acceptable excipients include, but are not limited to, carriers, preservatives, and/or coloring agents. General considerations in the composition and/or manufacture of pharmaceutical compositions may be found, for example, in Remington The Science and Practice of Pharmacy 21st ed., Lippincott Williams & Wilkins, 2005.

In certain embodiments, the compositions described herein can be formulated as a liquid for oral administration. Liquid compositions include solutions, suspensions and emulsions. Examples of liquid pharmaceutical preparations include propylene glycol solutions and solutions containing sweeteners for oral solutions, suspensions and emulsions. When the liquid composition comes into contact with an aqueous medium, such as for example an aqueous medium having an acidic environment, the composition forms micelles.

In certain embodiments, the dosage form comprises micelles which may be pre-formed prior to administration to a subject in need of such administration, and wherein said micelles range in size from 1 um to 10 um in diameter. Such pre-formed micelles are stable at room temperature.

In other embodiments, the compositions described herein can be formulated as a fill material for capsules, including for example, a soft gelatin capsule. Likewise, when the contents of the soft gelatin capsule comes into contact with an aqueous medium, the composition forms micelles upon disintegration of the capsule.

A capsule may be prepared, e.g., by placing the compositions described above inside a capsule shell. A capsule is a dosage form administered in a special container or enclosure containing an active agent. In some embodiments the compositions described herein can be filled into soft capsules. A capsule shell may be made of methylcellulose, hydroxypropylmethyl cellulose, polyvinyl alcohols, or denatured gelatins or starch or other material. Hard shell capsules are typically made of blends of relatively high gel strength bone and pork skin gelatins. In some embodiments the unit dosage form is a gel capsule. In some embodiments the capsule shell is a glycerin capsule shell, for example product no. GSU0051 manufactured by SwissCaps and which meets USP 25 requirements (SwissCaps, USA 14193 SW 119th Ave., Miami/Fla., U.S. 33186). In other embodiments the capsule is a bovine gelatin shell, for example SwissCaps product no. GSU0708. Other suitable capsule shell materials include polyethylene, polypropylene, poly(methylmethacrylate), polyvinylchloride, polystyrene, polyurethanes, polytetrafluoroethylene, nylons, polyformaldehydes, polyesters, cellulose acetate, and nitrocellulose. The capsule shell itself may contain small amounts of dyes, opaquing agents, plasticizers, and preservatives. Conventional methods for preparing other solid dosage forms, for example, capsules, suppositories, and the like are also well known. Gelatin capsule shells may be made also be made of tapioca, grass, vegetable derived or fish derived gelatin. For example K-CAPS (Capsuline, Inc. Pompano Beach, Fla.) is a certified Kosher soft capsule shell of vegetable origin. Other vegetarian derived gelatin capsules may, be made of vegetable derived hydroxypropylmethyl cellulose (HPMC). Capsules shells may also contain Modified Maize Starch, Glycerol, and Carrageenan as a gelling agent.

In other embodiments the capsule has a shell comprising the material of the rate-limiting membrane, including coating materials, and filled with the compositions described herein. Capsule shells may be made of a porous or a pH-sensitive polymer made by a thermal forming process. In certain embodiments the capsule shell in the form of an asymmetric membrane; i.e., a membrane that has a thin skin on one surface and most of whose thickness is constituted of a highly permeable porous material.

Yet another useful capsule, a "swelling plug device", can be used. The compositions described herein can be incorporated into a non-dissolving capsule-half of the device which is sealed at one end by a hydrogel plug. This hydrogel plug swells in an aqueous environment, and, after swelling for a predetermined time, exits the capsule thus opening a port through which the active agent can leave the capsule and be delivered to the aqueous environment. Preferred hydrogel-plugged capsules are those which exhibit substantially no release of active agent from the dosage form until the dosage form has exited the stomach and has resided in the small intestine for about 15 minutes or more, preferably about 30 minutes or more, thus assuring that minimal omega-3 fatty acid (either in the triglyceride, ester, or free fatty acid form) is released in the stomach or the small intestine. Hydrogel-plugged capsules of this type have been described in patent application WO90/19168.

The dosage forms may contain a plasticizer, such as for example, in a capsule shell. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose, triacetin, glycerin, sorbitol, sorbitan or combinations thereof.

In additional embodiments, the compositions can be formulated as a liquid for parenteral administration, particularly for intravenous administration, added to infant formula, or injected into an intravenous bag comprising a saline or other pharmaceutically acceptable solution or a nutritional supplement.

The compositions described herein can be formulated as one or more dosage units. In some embodiments, it can be advantageous to formulate oral compositions in dosage unit form for ease of administration and uniformity of dosage. Dosage unit forms described in some embodiments can refer to physically discrete units suited as unitary dosages for the subject to be treated; each unit containing a predetermined quantity of active composition calculated to produce the desired therapeutic effect in association with the suitable pharmaceutical carrier.

In certain embodiments, the dosage form may optionally contain a flavorant such as orange oil, substantially pure d-limonene, and an antioxidant such as tocopherol, tocotrienol, ascorbyl palmitate or a combination of antioxidants.

Functional Foods

Certain embodiments of the present invention provide for functional foods comprising compositions which contain at least one surface active agent and at least one omega-3 fatty acid (in triglyceride, ester, or free fatty acid form) in relative concentrations sufficient to form micelles when added to an aqueous medium, and wherein said micelles range in size from 1 um to 10 um in diameter. These functional foods may further contain one or more of (1) at least one fat-soluble vitamin, such as vitamin A, vitamin E, vitamin D, vitamin K, vitamin K2, among others, (2) one or more minerals, such as magnesium, manganese, zinc, copper, selenium, and combinations thereof, and (3) an omega-6, for example arachidonic acid (ARA), linoleic acid (LA), gamma-linolenic acid (GLA) or the omega-6 isomer of DPA.

In certain embodiments, the compositions described herein comprise micelles pre-formed prior to administration to a subject in need of such administration. Such pre-formed micelles are stable at room temperature. Accordingly, either such pre-formed micelles or said pre-micellized compositions in combination with a foodstuff, are provided, and can then be consumed as part of a healthy diet for enriching a subject's omega-3 fatty acid levels or as a dietary treatment in addition to the oral/parenteral administration of the compositions described herein as prescribed by a health professional.

In certain embodiments, the functional food is in the form of edible or drinkable compositions, e.g., foodstuffs such as chewable or edible bars, confectionary products (e.g., chocolate bars), cookies, juice drinks, baked or simulated baked goods (e.g., brownies), biscuits, lozenges or chewing gum. Examples of chewable or edible bars include chocolate bars or energy bars. Such functional foods can be particularly useful to people participating in sports or other forms of exercise.

In certain embodiments, the functional foods may also be in the form of, for example, butter, margarine, bread, cake, milk shakes, ice cream, yogurt and other fermented milk product.

In certain embodiments, the functional food can also be in the form of a liquid to be sprayed on meats, salads or other foods.

Other forms of the functional foods can be baby food, breakfast cereals, such as for example, grain flakes, muesli, bran, oatmeal.

When the functional food product is in a drinkable form, the compositions described herein can be added directly to the drink, such as for example plain milk, flavored milk, fermented milk products or juices, or infant formula. The compositions will form micelles comprising the omega-3 fatty acids in the drinkable product.

When the functional food is in the form of a solid edible product, the compositions described herein can be first added directly to a functional food or to an aqueous medium, wherein the composition will form micelles as described herein. The aqueous medium comprising the micelles can subsequently be either sprayed onto the solid edible product or mixed into the ingredients when manufacturing the edible product.

In certain embodiments particularly for the treatment of sickle cell disease, at least one surface active agent and one or more omega-3 fatty acids (in triglyceride, ester, or free fatty acid form, e.g. DHA alone or DHA and EPA: 500 mg), are further combined with Protein: 50 g, Vitamin A: 5,000 International Units (IU); Vitamin C: 60 mg, Vitamin E: 30 IU, Beta carotene, Folate: 400 µg, Zinc: 15 mg, Manganese: 2 mg, Copper: 2 mg, and Selenium: 70 µg.

In certain embodiments of the invention, at least one surface active agent is combined with at least one fat-soluble vitamin and an omega-3 fatty acid (in triglyceride, ester, or free fatty acid form) in relative concentrations sufficient to form micelles when added to an aqueous medium. In certain other embodiments of the invention, at least one surface active agent is combined with at least one fat-soluble vitamin, an omega-3 fatty acid (in triglyceride, ester, or free fatty acid form), and one or more minerals, such as magnesium, manganese, zinc, copper, selenium, and combinations thereof.

EXAMPLES

Macular Degeneration

Example 1

The amounts and percentages of the ingredients comprising one embodiment of the compositions described herein are shown in Table 1:

TABLE 1

| COMPOSITION | | |
|---|---|---|
| INGREDIENT | Amount (mg) | % (wt/wt) |
| DHA Omega-3 fatty acid Ethyl Ester*† | 754.3 | 68.57 |
| Polysorbate 80 | 337.9 | 30.72 |
| Poloxamer 237 (Pluronic ® F87) | 7.8 | 0.71 |
| TOTAL | 1100 | 100 |

*The omega-3 oil may contain ~2% α-tocopherol as an antioxidant.
†DHA comprises at least 90% of the DHA oil (678.9 mg). The majority of the remaining no more than 10% is EPA (~5%, or up to 37.7 mg)

Example 2

The amounts and percentages of the ingredients comprising one embodiment of the compositions described herein are shown in Table 2:

TABLE 2

| COMPOSITION | | |
|---|---|---|
| INGREDIENT | Amount (mg) | % (wt/wt) |
| EPA/DHA Omega-3 fatty acid Ethyl Ester*† | 754.3 | 65.59 |
| Gamma-tocotrienol | 50.0 | 4.35 |
| Polysorbate 80 | 337.9 | 29.38 |
| Poloxamer 237 (Pluronic ® F87) | 7.8 | 0.68 |
| TOTAL | 1150 | 100 |

*The Omega-3 oil may contain ~2% α-tocopherol as an antioxidant.
†EPA comprises 383 mg and 170 mg DHA.

Malabsorption Syndrome

Example 3

A study was conducted to evaluate, in an established porcine model of SBS, the systemic absorption and intestinal adaptation capacity of an ethyl ester form of DHA in combination with a surface active agent composition effective to spontaneously form micelles with said fatty acids upon contact with an aqueous media. In certain embodiments, the self-micellizing compositions may further contain at least one additional omega-3 fatty acid (either in the triglyceride, ester, or free fatty acid form), for example EPA or other known omega-3 fatty acids as disclosed herein. In certain embodiments, the self-micellizing compositions may further contain an anti-oxidant, such as tocopherol. In certain embodiments, the self-micellizing compositions may further contain an omega-6 fatty acid (either in the triglyceride, ester, or free fatty acid form), for example arachidonic acid (ARA), linoleic acid (LA), gamma-linolenic acid (GLA) or the omega-6 isomer of DPA, also known as osbond acid. This composition allows for micelle formation independent of the presence of bile salts as compared to a standard triglyceride form of DHA without a surface active agent (Control).

Materials and Methods
Animals and Surgical Induction of Short Bowel Syndrome

Newborn, crossbred (Hampshire×Landrace×Durocx Yorkshire) piglets (n=10), were weighed, placed in cages in a heated room (~30° C.), and were fed with a commonly available sow milk replacement formula. After an overnight fast, piglets underwent surgery for the placement of jugular and intragastric catheters for postoperative parenteral and enteral nutrition, respectively, and small bowel resection surgery. Following a 4-cm midline incision an 80% mid-jejunoileal resection was performed. The total amount of bowel resection was approximated using the following equation: total intestinal length=280 cm×body weight^0.60. A 20% remnant (~60 cm total per kg BW) remained and was represented equally between proximal jejunum and ileum, representing ~30 cm each remnant segment per kg bodyweight. ~45 cm of jejunum distal to the ligament of Treitz and ~45 cm of ileum proximal to the ileocecal junction were measured using sterile silk ribbon placed along the antimesentric border of the gently stretched small intestine. Intestine not included in the measurement was removed via cauterization. Bowel continuity was restored using an end-to-end jejunoileal anastomosis.

Postoperative Nutrition
Parenteral nutrition formula which does not contain DHA was provided proportionately to body weight to all piglets within 3 h after the operation. Continuous enteral feeding with a commonly available sow milk replacer formula, also lacking DHA, was slowly introduced 24 h after intestinal resection at 3 mL/kg*h via the intragastric catheter. The volume of enteral feedings was then advanced every 24 h by 1 ml/kg*h until a final enteral volume of 5 mL/kg*h was achieved on postoperative day 3 which represents approximately 50% of full enteral feeding volume and nutrient intake.

Provision of Oral Treatment & Control Groups

After the surgical procedure, piglets were randomly allocated into two groups (N=5 per group), control and SBS-treatment group. The control group received a standard DHA ethyl ester preparation of substantially pure DHA ethyl ester (>90% DHA ethyl ester). The SBS-treatment group received an equivalent amount of DHA as the control group, based on animal weight as described herein, of a preferred embodiment of the present invention comprising, about 683.9 mg/g of substantially pure DHA ethyl esters (>90% DHA ethyl ester), 2.7 mg/g of alpha-tocopherol, 306.3 g/mg of polysorbate 80, and 7.1 mg/g of poloxamer 237.

SBS-treatment: The control and SBS-treatment formulations, respectively, mixed in the enteral feeding at the respective dose and infused via the intragastric catheter at a dose of 1 g/kg*day for a period of 4 days after which time the animals were sacrificed.

Growth Data and Sample Collection

Growth

Piglets were weighed every other day. In addition to calculating a change in weight by subtracting the starting weight at the time of randomization from the final weight, percent weight change and growth velocity (g/kg*d) were also calculated. Percent weight change was calculated by: [((final weight-starting weight)/starting weight)×100]. Growth velocity was calculated by: [(weight change/starting weight)/4 days of treatment].

TABLE 3

Cohort characteristics and weight parameters (median ± IQR)

|  | Control (n = 5) | Treated (n = 5) | p |
| --- | --- | --- | --- |
| Male, n (%) | 4(80) | 3(60) | 0.51 |
| Weight at start, g | 2490 ± 114 | 2474 ± 325 | 0.75 |
| Weight at finish, g | 2594 ± 170 | 3170 ± 800 | 0.35 |
| Change in weight, g | 132 ± 278 | 696 ± 475 | 0.08 |
| Growth velocity, g/kg/d | 13.5 ± 30.1 | 69.9 ± 41.5 | 0.08 |
| Weight change, % | 5.4 ± 12.1 | 28.0 ± 16.6 | 0.08 |

Longitudinal Plasma Fatty Acid Levels

Blood samples for systemic fatty acid profiles were obtained on the day of surgery and then twice daily until sacrifice on fourth postoperative day. Plasma fatty acids were isolated and measured.

Intestinal Samples and Morphometry Measurements

Samples of intestinal tissue resected at the time of surgery and remnants at sacrifice were collected from proximal jejunum (proximal to anastomosis) and distal ileum (distal to anastomosis) and morphological measurements of the crypts and villi were measured. Only intact villi and crypts were measured. All measurements were made by the same, single, blinded observer.

Statistical Analysis

The primary outcome measure was a change in plasma DHA level in the SBS-treated group versus control group. Given the small number of piglets per group, appropriate small group statistical methods were used to evaluate differences in outcome variables. Variable summary statistics are expressed as median±interquartile range (IQR). The Wilcoxon Rank-Sum test, which is appropriate to compare two non-normal distributions as is common in small sample size, was used to compare outcome measures between groups; while the Wilcoxon signed-rank test, which is appropriate for repeated measurements within the same animal, was used to compare paired, before and after surgery outcome measures within groups. Differences in growth measurements and fatty acid levels over time between groups were evaluated using generalized linear mixed models (GLMM) to account for repeated measures and non-Gaussian, non-normal data.

Results

Piglet Characteristics and Weight Trends

Four of the 5 piglets were male in the control group while 3 of the 5 were male in the SBS-treatment group (Table 1). The median starting weight was similar in both groups. At the end of the protocol, the median difference in final weight from starting weight was 696±425 g in the SBS-treatment group compared to 132±278 g in the control group. In concordance with the weight difference the percent weight change and growth velocity was greater in the SBS-treatment group compared to the control group. However, due to the short duration of this model as well as the sample size, these differences in growth parameters did not reach statistical significance.

Small Bowel Resection and Final Organ Weights

There were no differences in the total length or weight of resected bowel per kg weight of the piglet (Table 4). A median total of 138±34 cm per kg of small bowel was removed from piglets in the SBS-treatment group compared to 119±7 cm per kg in the control group. Similarly, there were no differences in the final length or weight of the jejunum and ileum segments of the small bowel per kg weight. Finally, the liver and brain weights per kg at sacrifice were comparable between the two groups.

TABLE 4

Small intestine resection and final organ weights (median ± IQR)

|  | Control | SBS-Treatment | p |
| --- | --- | --- | --- |
| Resected SI, g/kg | 29.5 ± 2.2 | 28.7 ± 4.9 | 0.92 |
| Resected SI, cm/kg | 119 ± 7.0 | 138 ± 3.4 | 0.17 |
| Jejunum, g/kg | 5.2 ± 1.4 | 5.1 ± 0.5 | 0.92 |
| Jejunum, cm/kg | 21.2 ± 6.7 | 16.5 ± 3.8 | 0.60 |
| Ileum, g/kg | 5.3 ± 1.2 | 7 ± 1.4 | 0.05 |
| Ileum, cm/kg | 17.5 ± 4.7 | 19.2 ± 4.4 | 0.33 |
| Liver, g/kg | 36.3 ± 2.5 | 37.0 ± 4.2 | 0.71 |
| Brain, g/kg | 14.0 ± 1.6 | 11.6 ± 2.3 | 0.09 |

IQR: Interquartile range; SI: Small Intestine; SBS-treatment

Plasma Fatty Acid Levels

Initial plasma fatty acid levels in mol % (Time 0) of DHA, Eicosapentaenoic acid (EPA), ARA, and Linoleic acid (LA) obtained at the time of surgery were similar between groups (2.0±0.04 vs 2.3±0.4; 0.2±0.06 vs 0.3±0.1; 11.0±0.3 vs 11.8±0.5; 18.1±2.3 vs 16.6±1.8, respectively) (FIG. 1). Within 12 hours (after the first enteral dose of DHA), the DHA and EPA levels were significantly greater in the SBS-treatment group versus control group (4.1±0.3 vs 2.5 vs 0.5, p=0.009; 0.7±0.3 vs 0.2±0.005, p=0.009, respectively). For DHA these differences persisted until the final measurement; while the EPA plasma level differences persisted throughout the remaining duration of the protocol. On the third postoperative day, plasma ARA levels began to diverge between the groups, with lower values in the SBS-treatment group versus the control group (7.1±1.5 vs 8.7±0.8, p=0.03). The difference persisted throughout the remaining duration of the protocol. There were no differences throughout the study protocol in plasma LA levels.

Small Bowel Morphometry

At the time of surgery (Day 0), villus height measurements of the proximal jejunum and distal ileum were similar in both groups (FIG. 2). In the control group, the villus height of the proximal jejunum at the end of the experiment (Final) was not significantly different to the values obtained at the time of surgery; whereas in the distal ileum villus height was reduced, but not significantly different (p=0.07). In contrast, in the SBS-treatment group, the final villus height was increased from the starting value in the proximal jejunum (p=04). In the distal ileum, the SBS-treatment group demonstrated maintenance of overall villus height and compared to the control group, a significant increase in the final villus height (p=0.01).

Crypt depth was increased at the end of the experiment compared to baseline values in the proximal jejunum within both control and SBS-treatment groups (p<0.05). There were no differences between groups in the baseline or final crypt depth measurements. Similar to the proximal jejunum, the crypt depth of the distal ileum was increased from baseline in the distal ileum within the control group (p<0.05). In contrast, there were no changes in the baseline to final crypt depth in the distal ileum for the piglets in the SBS-treatment group. The final crypt depths in the distal ileum were not significantly different between the two groups.

Discussion

Piglets with surgically induced SBS who were given dietary supplementation in the SBS-treatment group demonstrated improved absorption of DHA, greater ileal adaptation, and a trend towards improved growth compared to piglets given a standard preparation of DHA. Within 12 hours, the plasma levels of both DHA and EPA in the SBS-treatment group began to significantly diverge from the control group. While not wishing to be bound to any particular theory, an increase of EPA is believed to be a result of retro-conversion of DHA to EPA as neither DHA formulation contained an EPA supplement. The observed reduction in ARA with increasing DHA levels in the SBS-treatment group is a known phenomenon. However, while not wishing to be bound to any particular theory, as DHA levels increase with DHA-only dietary supplementation, ARA levels decline as a result of the competition for enzyme activity, the sn-2 position of phospholipids in membranes, as well as the body's ability within the plasma compartment to maintain a constant number of double bonds. This is not a generalized phenomenon as Linoleic Acid levels were unchanged throughout the experimental time period.

An increase in villus height and crypt depth is a known observation in intestinal adaptation after significant bowel resection in both animal models and in humans. This was observed for both groups in the proximal jejunum and distal ileum reinforcing the validity of this model in studying intestinal changes in short bowel syndrome. In the proximal jejunum the SBS-treatment group demonstrated a greater attainment in villus height compared to baseline. In the distal ileum, the SBS-treatment group maintained villus height while the control group lost villus height suggesting a greater intestinal adaptive response for the piglets receiving the SBS-treatment preparation. The piglets in the SBS-treatment group appeared to have an accelerated adaptive response compared to the control group possibly due to the efficient bioavailability and intestinal absorption of DHA. This may be a clinically relevant observation during the critical, immediate postoperative period. Although increased jejunal crypt depth was seen in both groups after 4 days, the lack of change in the ileum selectively in the SBS-treatment group suggests that increased bioavailability of DHA is exerting an intestinal trophic effect. While not wishing to be bound to any particular theory, it is possible that DHA is modulating intestinal cell growth and differentiation through PPAR or other growth factors.

The example described herein provides data necessary to support the clinical utility of a novel preparation of DHA that allows for bile acid independent formation of micelles enhancing absorption and biological effectiveness of DHA early in the postoperative period.

Example 4

The amounts and percentages of the ingredients comprising one embodiment of the compositions described herein are shown in Table 5:

TABLE 5

| COMPOSITION | | |
|---|---|---|
| INGREDIENT | Amount (mg) | % (wt/wt) |
| DHA Omega-3 fatty acid Ethyl Ester*† | 685.7 | 68.57 |
| Polysorbate 80 | 307.2 | 30.72 |
| Poloxamer 237 (Pluronic ® F87) | 7.1 | 0.71 |
| TOTAL | 1000 | 100 |

*The omega-3 oil may contain ~2% α-tocopherol as an antioxidant.
†DHA comprises at least 90% of the DHA oil (617.3 mg). The majority of the remaining no more than 10% is EPA (~5%, or up to 34.3 mg)

During administration, sterile saline solution is added to the vial and mixed to homogeneity to form a milky solution, which can then be administered intravenously directly into a human in need of such administration, such as for example a neonate, added to infant formula, into an IV infusion bag, via a stomach feeding tube, or through a duodenal feeding tube.

Example 5

The amounts and percentages of the ingredients comprising one embodiment of the compositions described herein are shown in Table 6:

TABLE 6

| COMPOSITION | | |
|---|---|---|
| INGREDIENT | Amount (mg) | % (wt/wt) |
| DHA Omega-3 fatty acid Ethyl Ester*† | 651.4 | 65.14 |
| Arachidonic Omega-6 Ethyl Ester*° | 34.3 | 3.43 |
| Polysorbate 80 | 307.2 | 30.72 |
| Poloxamer 237 (Pluronic ® F87) | 7.1 | 0.71 |
| TOTAL | 1000 | 100 |

*The omega-3 oils may contain ~2% α-tocopherol as an antioxidant.
†DHA comprises at least 90% of the DHA oil (586.3 mg). The majority of the remaining no more than 10% is EPA (~5%, or up to 32.6 mg)
°The ARA Ethyl Ester is at 80% pure.

NAFLD/NASH Examples

Example 6

The amounts and percentages of the ingredients comprising one embodiment of the compositions described herein are shown in Table 7:

TABLE 7

| COMPOSITION | | |
| --- | --- | --- |
| INGREDIENT | Amount (mg) | % (wt/wt) |
| DHA Omega-3 fatty acid Ethyl Ester*† | 754.3 | 68.57 |
| Polysorbate 80 | 337.9 | 30.72 |
| Poloxamer 237 (Pluronic ® F87) | 7.8 | 0.71 |
| TOTAL | 1100 | 100 |

*The omega-3 oil may contain ~2% α-tocopherol as an antioxidant.
†DHA comprises at least 90% of the DHA oil (678.9 mg). The majority of the remaining no more than 10% is EPA (~5%, or up to 37.7 mg)

Example 7

The amounts and percentages of the ingredients comprising one embodiment of the compositions described herein are shown in Table 8:

TABLE 8

| COMPOSITION | | |
| --- | --- | --- |
| INGREDIENT | Amount (mg) | % (wt/wt) |
| EPA/DHA Omega-3 fatty acid Ethyl Ester*† | 754.3 | 65.59 |
| Gamma-tocotrienol | 50.0 | 4.35 |
| Polysorbate 80 | 337.9 | 29.38 |
| Poloxamer 237 (Pluronic ® F87) | 7.8 | 0.68 |
| TOTAL | 1150 | 100 |

*The omega-3 oil may contain ~2% α-tocopherol as an antioxidant.
†EPA comprises 383 mg and 170 mg DHA.

Example 8

An embodiment of the present invention, referred to as SC410 herein, is a composition consisting of about: 68.39% docosahexaenoic acid ethyl esters (DHA), 0.27% alpha-tocopherol, 30.63% polysorbate 80, and 0.71% poloxamer 237. As disclosed herein, SC410 is preferably administered enterally to a mammal, such as a human, and delivered within a soft gelatin capsule although the routes of administration and delivery include other known routes. A nine-week preclinical study of certain embodiments of the present invention was conducted on 24 male mice using a mouse model ("NASH mice") which progresses from NAFLD to NASH between 5 to 6 weeks of age. Within the disease progression of this animal model, the animals reach NASH around week 6. Eight NASH mice were orally administered an olive oil vehicle in a volume of 2.5 mL/kg once daily from 5 to 9 weeks of age (Control Group). A second group, the "Second Treatment Group," also interchangeably referred to herein as NAFLD Group, composition 1-5 group, or composition 1-5 treatment, consisted of eight NASH mice which were orally administered said olive oil vehicle supplemented with SC410 once daily from 5 to 9 weeks of age. A third group, the "Third Treatment Group," also interchangeably referred to herein as NASH Group, composition 1-6 group or composition 1-6 treatment, consisted of eight NASH mice, which were orally administered said olive oil vehicle supplemented with SC410 once daily from 6 to 9 weeks of age. Non-fasting blood glucose was measured in whole blood and ALT levels were measured from plasma. Liver total lipid-extracts were obtained from right lobes by Folch's method.

FIG. 3 shows the mean body weight on the day of sacrifice of the mice between each of the Control, Second Treatment Group and Third Treatment Group.

Figure 4:
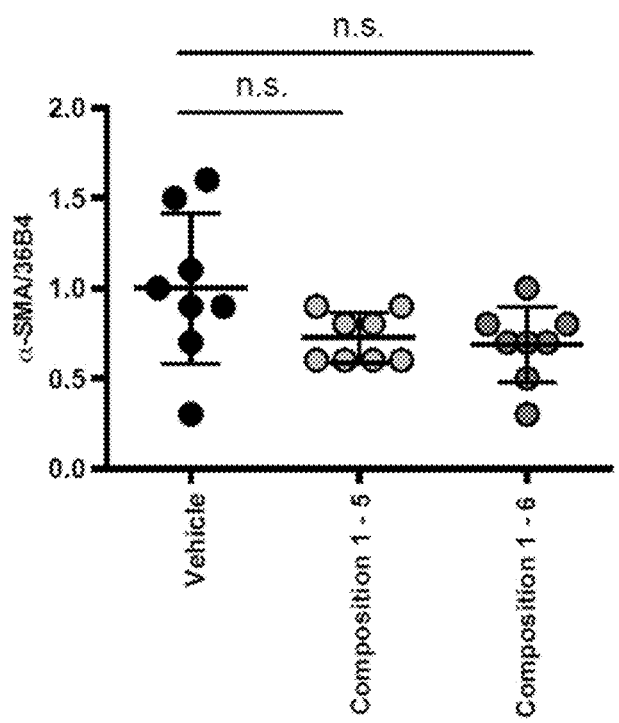
FIG. 4 shows α-SMA mRNA gene expression in mice in each of the control, NAFLD and NASH groups treated with either Vehicle or Composition 1 at the end of the treatment period.

FIG. 4 shows α-SMA mRNA gene expression in mice in each of the control, NAFLD and NASH groups treated with either Vehicle or Composition 1 at the end of the treatment period.

Figure 5:
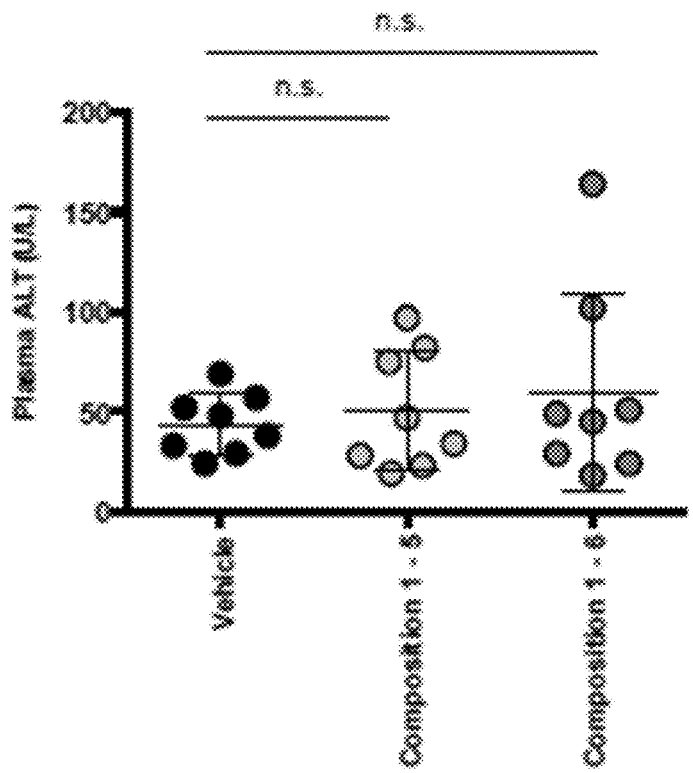
FIG. 5 shows plasma alanine transaminase (ALT) levels in mice between each of the control, NAFLD and NASH group treated with either Vehicle or Composition at the end of the treatment period.

FIG. 5 shows plasma alanine transaminase (ALT) levels in mice between each of the control, NAFLD and NASH group treated with either Vehicle or Composition at the end of the treatment period.

Figure 6:
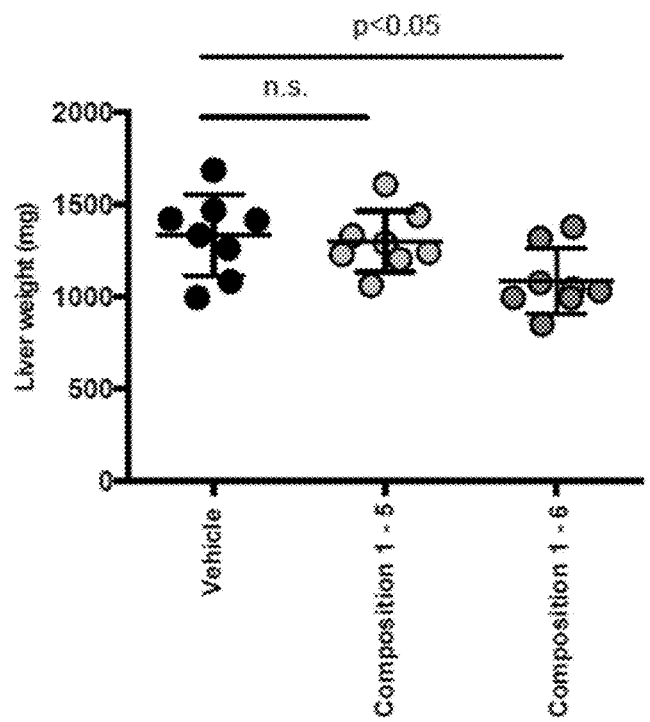
FIG. 6 shows the mean liver weight on the day of sacrifice of the mice between each of the treatment groups and the control.

FIG. 6 shows the mean liver weight on the day of sacrifice of the mice between each of the treatment groups and the control.

Figure 7:
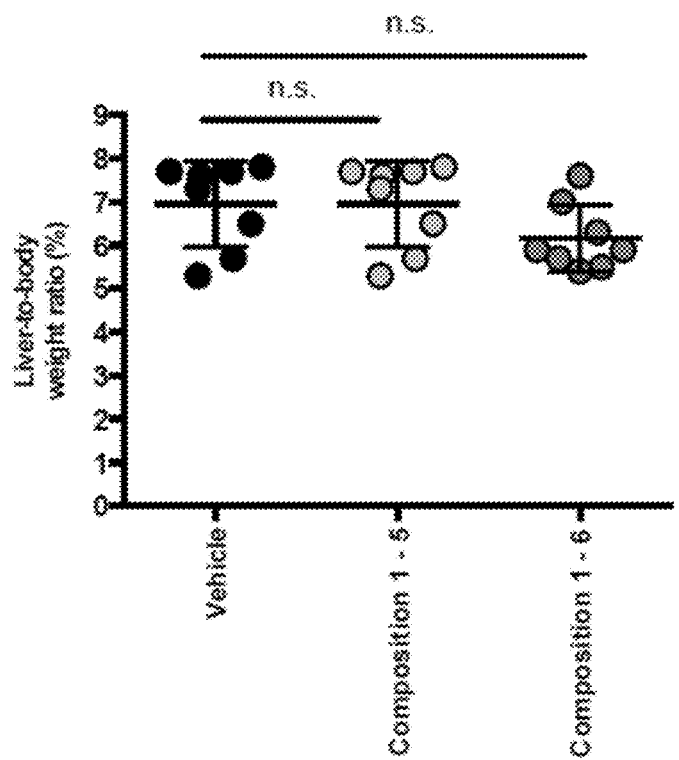
FIG. 7 shows the mean liver to body weight ratio on the day of sacrifice of the mice between each of the treatment groups and the control.

FIG. 7 shows the mean liver to body weight ratio on the day of sacrifice of the mice between each of the treatment groups and the control.

Figure 8:
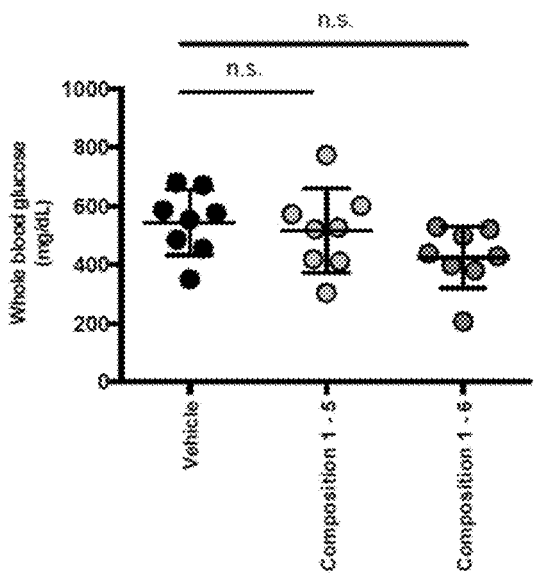
FIG. 8 shows whole blood glucose in mice between each of the control, NAFLD and NASH group treated with either Vehicle or Composition at the end of the treatment period.

FIG. 8 shows whole blood glucose in mice between each of the control, NAFLD and NASH group treated with either Vehicle or Composition at the end of the treatment period.

Figure 9:
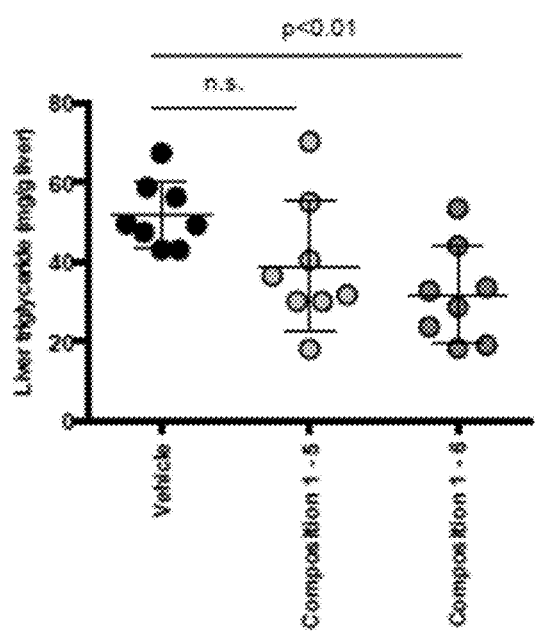
FIG. 9 shows liver triglyceride levels in mice between each of the control, NAFLD and NASH.

FIG. 9 shows liver triglyceride levels in mice between each of the control, NAFLD and NASH.

Figure 10A:
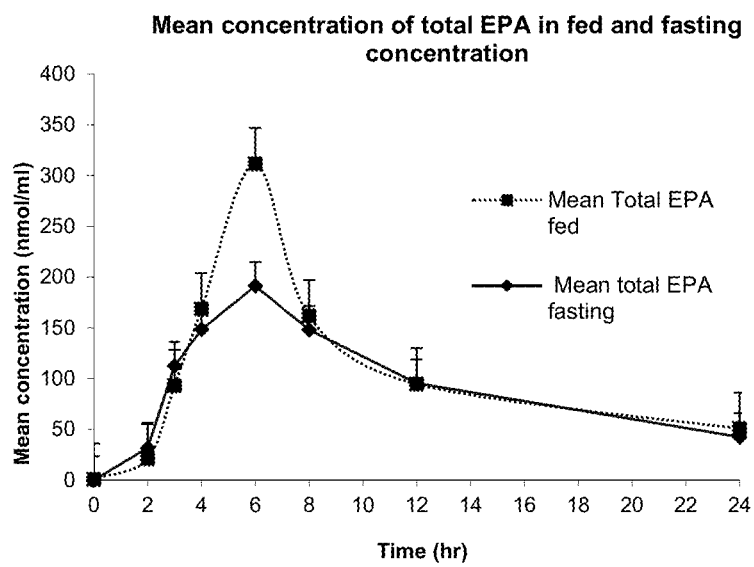
FIGS. 10 A and 10B show the mean individual EPA (A) and DHA (B) total lipid concentration-time profiles (baseline-adjusted change) after a single dose of SC401 during fed and fasting conditions.
Figure 10B:
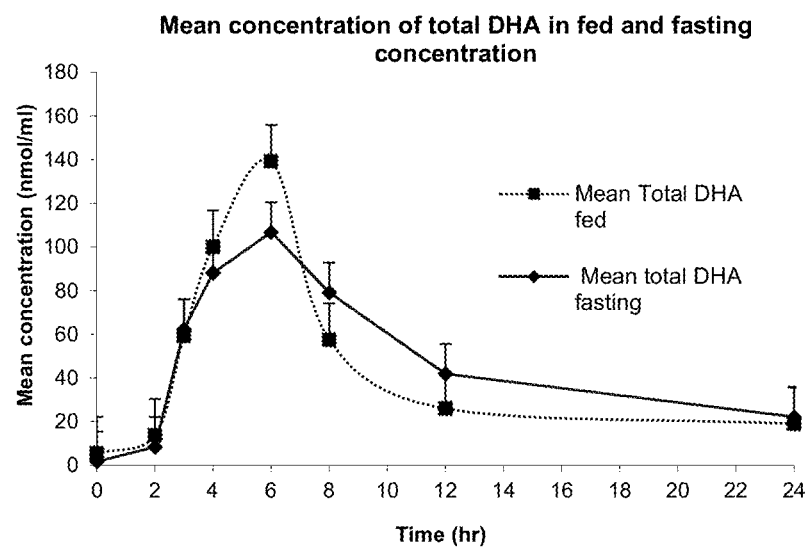

FIGS. 10A and 10B show the mean individual EPA (A) and DHA (B) total lipid concentration-time profiles (baseline-adjusted change) after a single dose of SC401 during fed and fasting conditions.

Figure 11A:
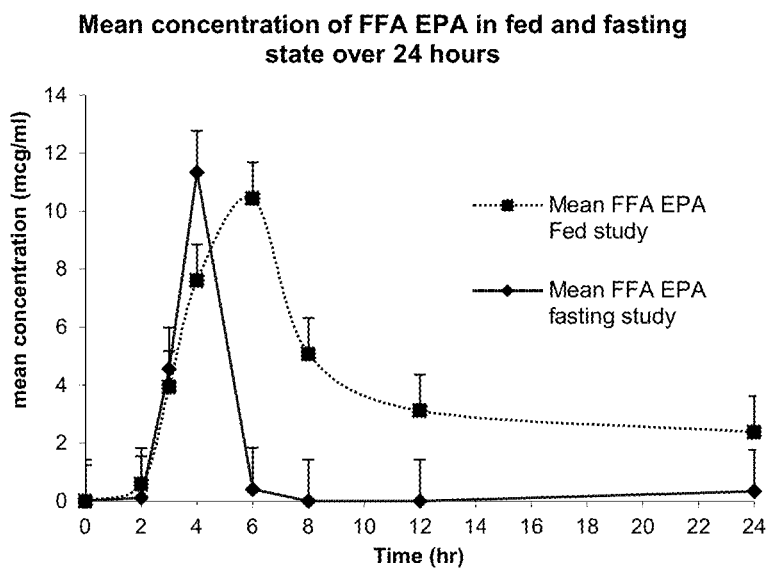
FIGS. 11A and 11B show the mean individual EPA (A) and DHA (B) free fatty acid concentration-time profiles (baseline-adjusted change) after a single dose of SC401 during fed and fasting conditions.
Figure 11B:
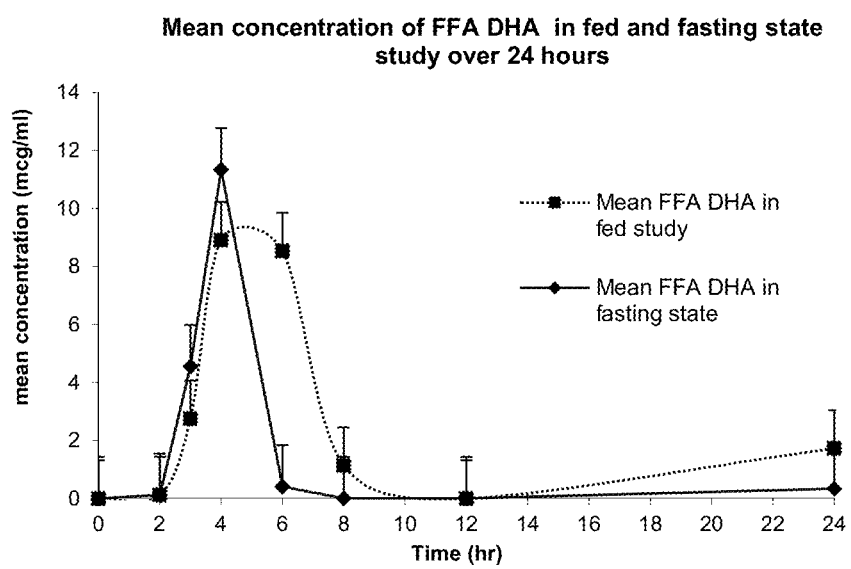

FIGS. 11A and 11B show the mean individual EPA (A) and DHA (B) free fatty acid concentration-time profiles (baseline-adjusted change) after a single dose of SC401 during fed and fasting conditions.

Figure 12:
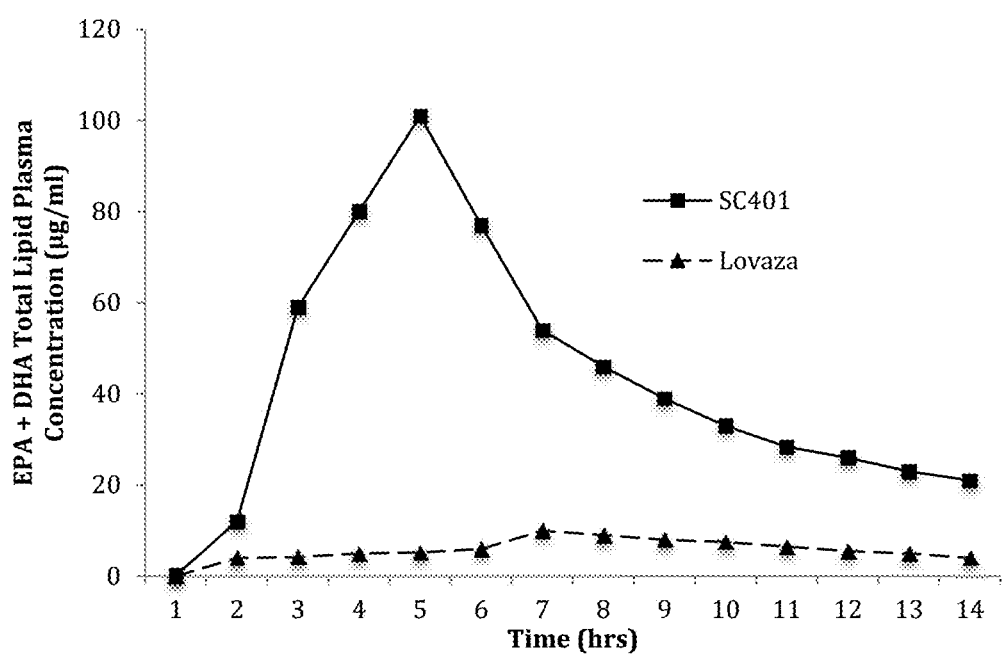
FIG. 12 shows mean EPA and DHA total lipid plasma concentration profiles (μg/ml) (baseline-adjusted) after administration of a single dose (dose adjusted) of SC401 and Lovaza® in fasted conditions.

FIG. 12 shows mean EPA and DHA total lipid plasma concentration profiles (μg/ml) (baseline-adjusted) after administration of a single dose (dose adjusted) of SC401 and Lovaza® in fasted conditions.

Note—N.S. In the Figures Stands for Non-Significant.

Body Weight

At the end of the experiment, it was determined that body weight gradually increased during the treatment period in all groups as would be expected in growing mice. There was no significant difference in mean body weight between the Control Group and the First Treatment Group during the treatment period although mean body weight on the day of sacrifice of the First Treatment Group tended to be decreased compared with the Control Group. However, the mean body weight of the Second Treatment Group was significantly lower than that of the Control Group at day 28.

α-SMA

α-SMA, a marker of myofibroblast associated with the development of liver fibrosis, mRNA expression levels tended non-significantly to decrease in both treatment groups as compared with the Control Group.

ALT Measurements

Although changes in ALT were not statistically significant between the groups, some animals within the treatment groups exhibited a marked increase in plasma ALT levels as compared to the control group. Since omega-3 administration has been shown in previous studies to elevate ALT, this result would be expected and may be an indicator of the efficacy of delivery of the omega-3 to the liver.

Liver Weight

Additionally, there was no significant difference in mean liver weight between the Control Group and the First Treatment Group, whereas the mean liver weight of the Second Treatment Group was lower than that of the Control group. When liver and body weight are compared collectively as a ratio, the Second Treatment Group non-significantly trends lower than the Control or First Treatment Group.

Blood Glucose

There was no significant difference in whole blood glucose between the Control Group and the First Treatment Group whereas whole blood glucose level tended to decrease in the Second Treatment Group compared with the Control Group.

Liver Triglycerides

Liver triglyceride contents tended to decrease in the First Treatment Group and significantly decreased in the Second Treatment Group compared with the Control Group.

CONCLUSIONS

The study showed that animals for which treatment was started later, the Second Treatment Group, had significantly reduced the liver triglyceride contents compared with the control group. Although the liver triglycerides tended to decrease in both treatment groups, the First Treatment Group showed a non-significant change (at 0.05) and the Second Treatment Group showed a statistically significant decrease. This Second Treatment Group also showed a decreasing tendency of whole blood glucose levels compared with the Control Group. The significant decrease in the liver triglycerides in the more progressed group demonstrate that certain embodiments of the present invention can improve lipid and glucose metabolism in the liver. These results also demonstrate that omega-3 fatty acids can improve lipid and glucose metabolism in the liver.

The effect of the treatment was not merely through an induction of weight loss by the animals. In fact, the study found that body weight gradually increased during the treatment period in all groups and that there was no difference in mean body weight between groups. Although the end liver weight of the subjects in the treatment groups was lower than that of the subjects in the Control Group, the difference was not statistically significant. In addition, both treatment groups trended to reduce alpha-SMA (a marker of myofibroblast associated with the development of liver fibrosis) mRNA expression in the liver, a key indicator of the treatment's demonstrated ability to delay the progression to NASH. There were no significant differences in fibrosis area between the Control Group and either group, data not shown.

Without being held to any one theory, we believe the study demonstrates the ability of at least one composition disclosed herein to deliver polyunsaturated EPA and DHA fatty acids to mammals with NAFLD for incorporation into the cell membrane of erythrocytes, wherein said delivery can reduce the triglyceride level in the liver and thereby slow the disease's progression to NASH. The study may also indicate that administration of compositions disclosed herein might provide a larger medicinal response when provided later in the disease progression from NAFLD to NASH.

Neurodegenerative Diseases Prophetic Non-Limiting Working Examples

Example 9

The amounts and percentages of the ingredients comprising one embodiment of the compositions described herein are shown in Table 9:

TABLE 9

| COMPOSITION | | |
|---|---|---|
| INGREDIENT | Amount (mg) | % (wt/wt) |
| DHA Omega-3 fatty acid Ethyl Ester*† | 754.3 | 68.57 |
| Polysorbate 80 | 337.9 | 30.72 |
| Poloxamer 237 (Pluronic ® F87) | 7.8 | 0.71 |
| TOTAL | 1100 | 100 |

*The omega-3 oil may contain ~2% α-tocopherol as an antioxidant.
†DHA comprises at least 90% of the DHA oil (678.9 mg). The majority of the remaining no more than 10% is EPA (~5%, or up to 37.7 mg)

Example 10

The amounts and percentages of the ingredients comprising one embodiment of the compositions described herein are shown in Table 10:

TABLE 10

| COMPOSITION | | |
|---|---|---|
| INGREDIENT | Amount (mg) | % (wt/wt) |
| EPA/DHA Omega-3 fatty acid Ethyl Ester*† | 754.3 | 65.59 |
| Gamma-tocotrienol | 50.0 | 4.35 |
| Polysorbate 80 | 337.9 | 29.38 |
| Poloxamer 237 (Pluronic ® F87) | 7.8 | 0.68 |
| TOTAL | 1150 | 100 |

*The omega-3 oil may contain ~2% α-tocopherol as an antioxidant.
†EPA comprises 383 mg and 170 mg DHA.

Primary Sclerosing Cholangitis Prophetic Non-Limiting Working Examples

Example 11

The amounts and percentages of the ingredients comprising one embodiment of the compositions described herein are shown in Table 11:

TABLE 11

| COMPOSITION | | |
|---|---|---|
| INGREDIENT | Amount (mg) | % (wt/wt) |
| DHA Omega-3 fatty acid Ethyl Ester*† | 754.3 | 68.57 |
| Polysorbate 80 | 337.9 | 30.72 |
| Poloxamer 237 (Pluronic ® F87) | 7.8 | 0.71 |
| TOTAL | 1100 | 100 |

*The omega-3 oil may contain ~2% α-tocopherol as an antioxidant.
†DHA comprises at least 90% of the DHA oil (678.9 mg). The majority of the remaining no more than 10% is EPA (~5%, or up to 37.7 mg)

Example 12

The amounts and percentages of the ingredients comprising one embodiment of the compositions described herein are shown in Table 12:

TABLE 12

COMPOSITION

| INGREDIENT | Amount (mg) | % (wt/wt) |
|---|---|---|
| EPA/DHA Omega-3 fatty acid Ethyl Ester*† | 754.3 | 65.59 |
| Gamma-tocotrienol | 50.0 | 4.35 |
| Polysorbate 80 | 337.9 | 29.38 |
| Poloxamer 237 (Pluronic ® F87) | 7.8 | 0.68 |
| TOTAL | 1150 | 100 |

*The omega-3 oil may contain ~2% α-tocopherol as an antioxidant.
†EPA comprises 383 mg and 170 mg DHA.

Example 13

The study described below will assess the effect of compositions described herein in a murine model of Primary Sclerosing Cholangitis (PSC). It is believed that treatment with the compositions described herein will be more effective in preventing and/or reversing bile duct injury in a mouse model of PSC.

The study will utilize a mouse model of PSC induced by DSS & DDC. The well established mouse model of PSC where exon 10 CFTR$^{+/-}$ knockout mice (heterozygotes) will be exposed to oral Dextran Sodium Sulfate (DSS) followed by up to 28 days of the xenobiotic DDC dissolved in peptamen (Martin C R, Zaman M M, Ketwaroo G A, Bhutta A Q, Coronel E, Popov Y, Schuppan D, Freedman S D. CFTR dysfunction predisposes to fibrotic liver disease in a murine model. Am J Physiol Gastrointest Liver Physiol 303: G474-G481, 2012).

The Cftr$^{+/-}$ mouse model of PSC consists of two phases: (1) induction of colitis with DSS for 10 days or until overt blood per rectum; and, (2) induction of liver inflammation and fibrosis with DDC for 28 days. The following protocol will begin using Cftr$^{+/-}$ mice at ~age 35 days, or week 5.

Induction of Colitis with DSS for 10 Days 85 mg of DSS dissolved in 12 ml of Peptamen by continuous vortexing.

The mice will be fed using a liquid feeder (Dyets Inc., Bethlehem, Pa.).

The mice will be monitored daily for onset of colitis by overt bleeding per rectum.

Once overt bleeding is noted (typically day 8-10 of DSS), DSS will be discontinued and the mice will be fed peptamen alone for one day.

Induction of Liver Inflammation and Fibrosis with Oral DDC for 28 Days

After overt colitis and one day of peptamen feeding alone, the mice will be treated for 28 days with 1.5 mg DDC in 12 ml of Peptamen per day Volume consumed will be recorded.

Treatment Groups 3 treatment groups will be used:

1) High DHA (40 mg/day)
2) High DHA (40 mg/day) with high bioavailability
3) No treatment All treatments will begin 3 days prior to the administration of DSS and thus will examine prevention of injury.

Sample Collection and Outcomes Measures a) Mice will be sacrificed by exposure to $CO_2$ for 2 min.
b) Body weight will be measured at the start of the protocol, every 3$^{rd}$ day, then at the end of the protocol. Percent weight change will be calculated as follows:

$$i.=((\text{Starting weight}-\text{End weight})/\text{Starting weight})*100$$

c) Liver and blood samples will be collected at sacrifice and stored as described below in Table 13 below.
d) Fatty acid levels will be determined in plasma and liver.

TABLE 13

Sample collection and processing

| Outcome Measure | Sample | Sample preparation/ storage | Sample analysis |
|---|---|---|---|
| Tissue | | | |
| Weight | Liver | Liver removed and weighed pre-fixation | BIDMC |
| Histology | Liver | Liver fixed in 10% buffered formalin for 2 hours followed by two PBS washes and stored in PBS at 4° C. H&E staining, Sirius red staining | BIDMC for blind scoring |
| Fatty Acids | Liver | Fatty acid extraction | BIDMC GC-MS |

Serum
Blood will be collected by cardiac puncture using a 1 ml syringe equipped with a 25 G needle. Blood will be placed on ice for 15 minutes. The sample will be centrifuged at 5500Xg and serum collected. On average, 150 – 200 uL of serum will be collected per mouse. The serum will be pre-aliquoted into separate vials for the following distribution. All aliquoted samples will be stored at –80° C.

| Fatty Acids | Serum | Fatty acid extraction | BIDMC GC-MS |
|---|---|---|---|

The following will be collected and stored for possible subsequent analyses depending on histology results.

| LOXL-2, α-SMA, or other markers TBD | Liver | Immunohistochemistry Two separate pieces of liver tissue will be provided for each animal. Tissue will be snap/flash frozen in tissue biopsy cassettes using liquid nitrogen and will be store at –80° C. | BIDMC |
| Inflammatory/ Fibrosis markers: procollagen-1, LOXL-2 TGF-β1, TGF-β2, TIMP-1, TIMP-2, MMP-2, MMP-9, TNF-α, α-SMA | Liver | Snap freeze, store at –80° C. | RT PCR at BIDMC |

| Liver Function Tests: | Sample | Amount | Destination |
|---|---|---|---|
| Alkaline Phosphatase, ALT, AST, Bilirubin | Serum | 50 uL | BIDMC |
| Luminex Cytokine Panel | Serum | 70 uL | BIDMC |

Tissue Histological Slide Scoring a) Slides will prepared from the left lateral and bifurcated medial lobes of the liver; each liver will have one slide stained with H&E and one with Sirius Red respectively.
b) Liver injury will be scored based on four criteria: (1) epithelial injury, intraepithelial inflammation, and mononuclear cell infiltration; (2) bile duct proliferation; (3) bile duct angulation; and (4) fibrosis. Each criterion receives a score between 0 and 3.

A scoring rubric is defined in the box below. Scoring as previously described in our AJP article, will be performed by two individuals blinded to the conditions

| SCORING RUBRIC | |
|---|---|
| 0 | Absent |
| 1 | Mild |
| 2 | Moderate |
| 3 | Severe | i. Epithelial injury, intraepithelial inflammation, and mononuclear cell infiltration will be scored on slides at 20× magnification stained with H&E.

ii. Bile duct proliferation will be scored at 5× magnification on slides stained with H&E.

iii. Bile duct angulation will be scored at 20× magnification on slides stained with H&E.

iv. Fibrosis will be scored on slides at 5× magnification stained with Sirius Red. All tissues will be held and processed at the same time for Sirius Red staining.

Fibrosis will be quantified on Sirius Red slides using ImageJ

Sickle Cell Disease Prophetic Non-Limiting Working Examples

Example 14

The amounts and percentages of the ingredients comprising one embodiment of the compositions described herein are shown in Table 14:

TABLE 14

| COMPOSITION | | |
|---|---|---|
| INGREDIENT | Amount (mg) | % (wt/wt) |
| DHA Omega-3 fatty acid Ethyl Ester*† | 754.3 | 68.57 |
| Polysorbate 80 | 337.9 | 30.72 |
| Poloxamer 237 (Pluronic ® F87) | 7.8 | 0.71 |
| TOTAL | 1100 | 100 |

*The omega-3 oil may contain ~2% α-tocopherol as an antioxidant.
†DHA comprises at least 90% of the DHA oil (678.9 mg). The majority of the remaining no more than 10% is EPA (~5%, or up to 37.7 mg).

Example 15

The amounts and percentages of the ingredients comprising one embodiment of the compositions described herein are shown in Table 15:

TABLE 15

| COMPOSITION | | |
|---|---|---|
| INGREDIENT | Amount (mg) | % (wt/wt) |
| EPA/DHA Omega-3 fatty acid Ethyl Ester*† | 754.3 | 65.59 |

TABLE 15-continued

| COMPOSITION | | |
|---|---|---|
| INGREDIENT | Amount (mg) | % (wt/wt) |
| Gamma-tocotrienol | 50.0 | 4.35 |
| Polysorbate 80 | 337.9 | 29.38 |
| Poloxamer 237 (Pluronic ® F87) | 7.8 | 0.68 |
| TOTAL | 1150 | 100 |

*The omega-3 oil may contain ~2% α-tocopherol as an antioxidant.
†EPA comprises 383 mg and 170 mg DHA.

Example 16

A Randomized, double blind, placebo-controlled study will be conducted to investigate the therapeutic potential of the compositions described herein for patients with homozygous sickle cell disease.

Objective:
1. To evaluate efficacy of the compositions described herein in treatment of sickle cell anemia.
2. To study change in number of sickle cell vaso-occlusive crises.
3. To monitor the safety of one or more of the compositions described herein in the treatment of sickle cell anemia Sample size: 60

Study medication (n=sample in each group):
1. Test (T): One or more of the compositions described herein (n=30)
2. Reference (R): Standard of Care (n=30)

Duration of Treatment: 6 Months

Inclusion Criteria:
1. Patients aged 2-24 y with HbSS, who are undergoing regular follow-up as an outpatient with Sickle Cell Disease.
2. The patients who will be in a steady state, defined as no evidence of fever, infection, or crisis for 4 wk before the start of the study.
3. Phenotypic characteristic was confirmed with the use of cellulose acetate electrophoresis at pH 8.5.
4. Can continue standard of care treatment.
5. Already on fish oil compounds will require wash out of 15 days.

Exclusion Criteria:
1. Presence of other chronic diseases.
2. Blood transfusion in the previous 4 mo.
3. A history of overt stroke.
4. Pregnancy.

Medication permitted: All of the patients receiving regular folate supplementation, and those, 5 y receiving standard oral prophylactic penicillin.

Investigation Parameters: Blood count, inflammatory markers (C-RP)

The primary end point will be rates of clinical vaso-occlusive crisis and secondary end points will include number of hospitalizations, haemolytic events, blood transfusion rate, school attendance, and blood count—will be analysed by intention-to-treat analysis and quality of life assessment.

Statistics: N=30. The vaso-occlusive crises will be summarized on the basis of the annualized crisis rate by dividing the total number of crises experienced by the number of follow-up months and multiplying by 12.

Example 17

The amounts and percentages of the ingredients comprising one embodiment of the composition, also referred to as SC401, are shown in Table 17:

TABLE 17

COMPOSITION (FILL MASS)/dosage form

| INGREDIENT | Amount (mg) | % (wt/wt) |
|---|---|---|
| Total Omega-3 fatty acid Ethyl Esters | 754.3 | 68.57 |
| EPA Ethyl Esters | 392.2 | 35.65 |
| DHA Ethyl Esters | 165.9 | 15.08 |
| Polysorbate 80 | 337.9 | 30.72 |
| Poloxamer 237 (Pluronic ® F87) | 7.8 | 0.71 |

GEL MASS/dosage form

| INGREDIENT | Amount (gm) | % (wt/wt) |
|---|---|---|
| Gelatin | 270 | 40 |
| Glycerin | 135 | 20 |
| Purified water | 270 | 40 |

The pharmacokinetic (PK) profiles and bioavailability of EPA and DHA comprising the SC401 formulation is graphically represented in FIGS. 10A, 10B, 11A AND 11B.

FIG. 10 shows mean EPA and DHA total lipid plasma concentration profiles (μg/ml) (baseline-adjusted) after administration of a single dose (dose adjusted) of SC401 and Lovaza® in fasted conditions.

The invention claimed is:

1. A pharmaceutical composition comprising:
   artificially formed micelles formed upon contact with an aqueous solution, the micelles comprising at least one omega-3 fatty acid and at least one surface active agent, and providing for absorption of omega-3 fatty acid esters substantially free of any food effect;
   wherein said at least one surface active agent comprises a combination of at least one polysorbate and at least one poloxamer,
   wherein said at least one polysorbate comprises from about 30.0% wt/wt to about 32.0% wt/wt of said composition,
   wherein said at least one poloxamer comprises from about 0.60% wt/wt to about 0.80% wt/wt of said composition,
   wherein said at least one polysorbate is polyoxyethylene (20) sorbitan monooleate (polysorbate 80), and
   wherein said at least one poloxamer is a block copolymer of polyethylene glycol and polypropylene glycol having the formula $[(HO(C_2H_4O)_{64}(C_3H_6O)_{37}(C_2H_4O)_{64}H]$ (Poloxamer 237).

2. The pharmaceutical composition according to claim 1, wherein said at least one omega-3 fatty acid comprises at least about 40.0% (wt/wt) of the composition.

3. The pharmaceutical composition according to claim 1, wherein said at least one polysorbate comprises about 31.0% (wt/wt) of the composition.

4. The pharmaceutical composition according to claim 1, wherein said at least one poloxamer comprises about 0.70% (wt/wt) of the composition.

5. The pharmaceutical composition according to claim 1, wherein said at least one omega-3 fatty acid is a triglyceride, an ester or a free fatty acid.

6. The pharmaceutical composition according to claim 1, wherein said at least one omega-3 fatty acid is docosahexaenoic acid (DHA), eicosapentaenoic acid (EPA), or a combination of both DHA and EPA.

7. The pharmaceutical composition according to claim 1, wherein said composition further comprises a non-omega-3 fatty acid active agent.

8. The pharmaceutical composition according to claim 7, wherein said non-omega-3 fatty acid active agent is arachidonic acid (AA), a nutritional supplement, a statin, an antioxidant, or any combination thereof.

9. The pharmaceutical composition according to claim 8, wherein said non-omega-3 fatty acid nutritional supplement is folic acid, vitamin C, vitamin E, betacarotene, magnesium, manganese, calcium, vitamin A, vitamin D, vitamin K1, vitamin K2, lutein, zeaxanthin, a zinc, a copper, or any combination thereof.

10. The pharmaceutical composition according to claim 1, wherein the antioxidant comprises tocopherol, tocotrienol, or a combination of both.

11. The pharmaceutical composition according to claim 1, wherein said micelles are from about 1.0 to 10.0 microns in size.

12. The pharmaceutical composition according to claim 1, wherein said omega 3 fatty acid is EPA,
   wherein said at least one polysorbate comprises about 31.0% (wt/wt) of the composition, and
   wherein said at least one poloxamer comprises about 0.70% (wt/wt) of the composition.

13. The pharmaceutical composition according to claim 1, wherein said EPA comprises at least about 40% (wt/wt) of the composition.

14. The pharmaceutical composition according to claim 1, wherein said omega 3 fatty acid is DPA, wherein said at least one polysorbate comprises about 31.0% (wt/wt) of the composition, and wherein said at least one poloxamer comprises about 0.70% (wt/wt) of the composition.

15. The pharmaceutical composition according to claim 1, wherein the pharmaceutical composition has a therapeutic bioavailability of the omega-3 fatty acid that is substantially equivalent when administered with or without food.

16. The pharmaceutical composition according to claim 1, wherein said micelles are spontaneously formed in aqueous solution without agitation.

17. The pharmaceutical composition according to claim 1 for use in treating or preventing a malabsorption syndrome.

18. The pharmaceutical composition according claim 1 for use in treating or preventing sickle cell disease or disease symptoms.

19. A pharmaceutical composition comprising:
   at least 90% pure docosahexaenoic acid (DHA); and
   at least one surface active agent comprising a combination of:
      polyoxyethylene (20) sorbitan monooleate (polysorbate 80) present from about 30.0% wt/wt to about 32.0% wt/wt of the composition, and
      a block copolymer of polyethylene glycol and polypropylene glycol having the formula $[(HO(C_2H_4O)_{64}(C_3H_6O)_{37}(C_2H_4O)_{64}H]$ (Poloxamer 237) present from about 0.60% wt/wt to about 0.80% wt/wt of said composition,
   wherein the composition artificially forms micelles upon contact with an aqueous solution, and the artificially formed micelles provide for absorption of the DHA substantially free of any food effect.

20. A micelle formed from a composition according to claim 1.

* * * * *